(12) United States Patent
Koradin et al.

(10) Patent No.: US 8,173,675 B2
(45) Date of Patent: May 8, 2012

(54) SUBSTITUTED AMINO-THIOUREA COMPOUNDS FOR COMBATING ANIMAL PESTS

(75) Inventors: Christopher Koradin, Ludwigshafen (DE); Markus Kordes, Bobenheim-Roxheim (DE); Ernst Baumann, Dudenhofen (DE); Ronan Le Vezouet, Mannheim (DE); Deborah L. Culbertson, Fuquay Varina, NC (US)

(73) Assignee: BASF SE, Ludwigshafen (DE)

( * ) Notice: Subject to any disclaimer, the term of this patent is extended or adjusted under 35 U.S.C. 154(b) by 356 days.

(21) Appl. No.: 12/601,017

(22) PCT Filed: May 13, 2008

(86) PCT No.: PCT/EP2008/055851
§ 371 (c)(1),
(2), (4) Date: Nov. 20, 2009

(87) PCT Pub. No.: WO2008/141980
PCT Pub. Date: Nov. 27, 2008

(65) Prior Publication Data
US 2010/0167927 A1    Jul. 1, 2010

Related U.S. Application Data

(60) Provisional application No. 60/939,931, filed on May 24, 2007.

(51) Int. Cl.
*A61K 31/47* (2006.01)
*C07D 215/14* (2006.01)
(52) U.S. Cl. ........................ 514/311; 546/165
(58) Field of Classification Search .................. 514/311; 546/165
See application file for complete search history.

(56) References Cited

FOREIGN PATENT DOCUMENTS

| | | |
|---|---|---|
| WO | WO 2006/125745 | 11/2006 |
| WO | WO 2007/020377 | 2/2007 |
| WO | WO 2007/060120 | 5/2007 |
| WO | WO 2008/009881 | 1/2008 |

OTHER PUBLICATIONS

International Search Report for International Application No. PCT/EP2008/055851; International Filing Date: May 13, 2008; Date of Completion: Aug. 8, 2009; Date of Mailing: Aug. 19, 2008.
International Preliminary Report on Patentability for International Application No. PCT/EP2008/055851; International Filing Date: May 13, 2008; Date of Issuance: Nov. 24, 2009.

*Primary Examiner* — Taofiq A Solola
(74) *Attorney, Agent, or Firm* — Brink Hofer Gilson & Lione

(57) ABSTRACT

The invention relates to substituted amino-thiourea compounds of formula (I), to the enantiomers, diastereomers and salts thereof and to compositions comprising such compounds. The invention also relates to the use of the substituted amino-thiourea compounds, of their salts or of compositions comprising them for combating animal pests. Furthermore the invention relates also to methods of applying such compounds. The substituted amino-thiourea compounds are defined by the following formula (I): wherein A, B, $R^1$, $R^2$, $R^3$, $R^4$, $R^{5.1}$, $R^{5.2}$ and $R^6$ are defined as in the description.

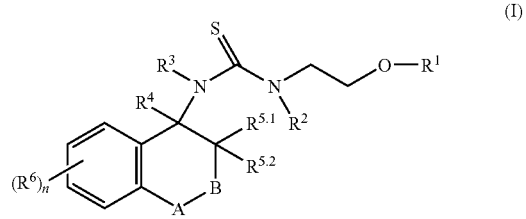

37 Claims, No Drawings

SUBSTITUTED AMINO-THIOUREA COMPOUNDS FOR COMBATING ANIMAL PESTS

This application is a National Stage application of International Application No. PCT/EP2008/055851 filed May 13, 2008, which claims the benefit of U.S. Provisional Application No. 60/939,931, filed May 24, 2007, the entire contents of which is hereby incorporated herein by reference.

The present invention relates to substituted amino-thiourea compounds, to the enantiomers, diastereomers and salts thereof and to compositions comprising such compounds. The invention also relates to the use of the substituted amino-thiourea compounds, of their salts or of compositions comprising them for combating animal pests. Furthermore the invention relates also to methods of applying such compounds.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

It is therefore an object of the present invention to provide compounds having a good pesticidal activity, especially against difficult to control insects and acaridae.

It has been found that these objects are solved by substituted amino-thiourea derivatives of the general formula I:

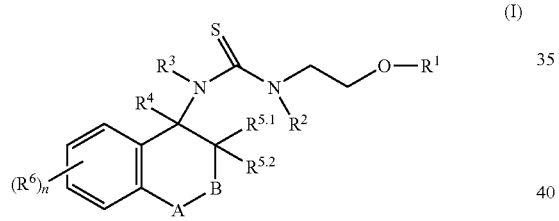

(I)

wherein
n is 0, 1, 2, 3 or 4.
A is $CR^{4.1}R^{4.2}$, oxygen, $NR^{4.3}$, sulfur, $S(O)$ or $S(O)_2$, wherein
  $R^{4.1}$, $R^{4.2}$ are independently of each other selected from the group consisting of hydrogen, halogen, cyano, nitro, hydroxy, mercapto, amino, $C_1$-$C_6$-alkyl, $C_1$-$C_6$-haloalkyl, $C_1$-$C_6$-alkoxy, $C_1$-$C_6$-alkylamino, di-($C_1$-$C_6$-alkyl)amino, wherein the carbon atoms in the last 5 mentioned radicals may be unsubstituted or may carry any combination of 1, 2 or 3 radicals $R^a$,
  $C_3$-$C_8$-cycloalkyl, phenyl or benzyl, each of the last three mentioned radicals may be unsubstituted or may carry any combination of 1, 2, 3, 4 or 5 radicals $R^b$; or
  $R^{4.1}$ together with $R^{4.2}$ may also be =O, =$NR^c$ or =$CR^dR^e$;
  $R^{4.3}$ is selected from the group consisting of hydrogen, formyl, CN, $C_1$-$C_6$-alkyl, $C_2$-$C_6$-alkenyl, $C_2$-$C_6$-alkynyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, ($C_1$-$C_6$-alkyl)thiocarbonyl, ($C_1$-$C_6$-alkoxy)thiocarbonyl, wherein the carbon atoms in the aliphatic radicals of the aforementioned groups may carry any combination of 1, 2 or 3 radicals $R^a$,
  $C(O)NR^fR^g$, $C(S)NR^fR^g$, $(SO_2)NR^fR^g$,
  phenyl, benzyl, phenoxycarbonyl, 5 or 6 membered hetarylmethyl, 5 or 6 membered hetarylcarbonyl and benzoyl each of the last six mentioned radicals may be unsubstituted or may carry any combination of 1, 2, 3, 4 or 5 radicals $R^b$, and wherein the 5 or 6 membered heteroaromatic ring in hetarylmethyl and hetarylcarbonyl contains 1, 2, 3 or 4 heteroatoms selected from oxygen, sulfur and nitrogen as ring members;
B is a chemical bond or $CH_2$;
$R^1$ is hydrogen, C(=O)$R^h$ or C(=S)$R^h$;
$R^2$, $R^3$ are selected independently from each other from the group consisting of hydrogen, cyano, nitro, formyl, C(=O)$R^i$, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkoxy)methylen, $C_1$-$C_6$-alkylsulfinyl, $C_1$-$C_6$-alkylsulfenyl or $C_1$-$C_6$-alkylsulfonyl wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, $C(O)NR^fR^g$, $(SO_2)NR^fR^g$, phenyl, phenyloxy or benzyl, each of the last three mentioned radicals may be unsubstituted or substituted with 1, 2, 3, 4 or 5 radicals $R^b$; or or
$R^2$ together with $R^1$ may be $C_1$-$C_3$-alkandiyl, $C_1$-$C_2$-alkandiylcarbonyl, $C_1$-$C_2$-alkandiylthiocarbonyl or a bridging C=O or C=S group.
$R^4$ is selected from the group consisting of hydrogen, formyl, cyano, $C_1$-$C_6$-alkyl, $C_1$-$C_6$-haloalkyl, $C_2$-$C_6$-alkenyl, $C_2$-$C_6$-alkynyl, $C_1$-$C_6$-alkoxycarbonyl, $C_1$-$C_6$-alkylcarbonyl, $C_2$-$C_6$-alkenylcarbonyl, $C_2$-$C_6$-alkynylcarbonyl, wherein the carbon atoms in the last 5 mentioned radicals may be unsubstituted or may carry any combination of 1, 2 or 3 radicals $R^a$;
  $C(O)NR^fR^g$, $C(S)NR^fR^g$,
  $C_3$-$C_8$-cycloalkyl, $C_3$-$C_8$-cycloalkenyl, aryl, arylmethyl, aryloxycarbonyl, arylcarbonyl, 5 or 6 membered hetaryl, 5 or 6 membered hetarylmethyl and 5 or 6 membered hetarylcarbonyl, each of the six last mentioned radicals may be unsubstituted or may carry any combination of 1, 2, 3, 4 or 5 radicals $R^b$;
$R^{5.1}$ $R^{5.2}$ are independently from each other selected from the group consisting of hydrogen, halogen, hydroxy, nitro, cyano, carboxy, formyl, formyloxy, $C_2$-$C_6$-alkenyl, $C_2$-$C_6$-alkynyl, $C_1$-$C_6$-alkoxy, $C_2$-$C_6$-alkenoxy, $C_2$-$C_6$-alkynoxy, $C_1$-$C_6$-haloalkoxy, $C_1$-$C_6$-alkylthio, $C_2$-$C_6$-alkenylthio, $C_2$-$C_6$-alkynylthio, $C_1$-$C_6$-haloalkylthio, wherein the carbon atoms in these groups may carry any combination of 1, 2 or 3 radicals $R^a$,
  $C_3$-$C_8$-cycloalkyl, $C_3$-$C_8$-cycloalkenyl, phenyl, benzyl, 5 or 6 membered hetaryl and 5 or 6 membered hetarylmethyl, each of the last mentioned cyclic radicals may be unsubstituted or may carry any combination of 1, 2, 3, 4 or 5 radicals $R^b$, and wherein the 5 or 6 membered heteroaromatic ring in hetarylmethyl and hetaryl contains 1, 2, 3 or 4 heteroatoms selected from oxygen, sulfur and nitrogen as ring members; or
  $R^{5.1}$ together with $R^{5.2}$ may also be =O, =S, =$NR^c$ or =$CR^dR^e$;
$R^6$ is selected from the group consisting of halogen, OH, SH, $NH_2$, $SO_3H$, COOH, cyano, azido, nitro, formyl, formyloxy, $CONH_2$, $CSNH_2$, CH=N—OH, CH=N—

O—($C_1$-$C_6$)-alkyl, C(=O)$R^j$, C(=S)$R^j$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, $C_1$-$C_6$-alkylamino, di($C_1$-$C_6$-alkyl)amino, $C_1$-$C_6$-alkylthio, $C_2$-$C_6$-alkenyloxy, $C_2$-$C_6$-alkenylamino, di($C_1$-$C_6$-alkenyl)amino, $C_2$-$C_6$-alkenylthio, $C_2$-$C_6$-alkynyl, $C_2$-$C_6$-alkynyloxy, $C_2$-$C_6$-alkynylamino, di($C_1$-$C_6$-alkynyl)amino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkenylsulfoxyl, $C_2$-$C_6$-alkynylsulfonyl, $C_2$-$C_6$-alkynylsulfoxyl, ($C_1$-$C_6$-alkoxy)carbonyl, ($C_2$-$C_6$-alkenyloxy)carbonyl, ($C_2$-$C_6$-alkynyloxy)carbonyl, ($C_1$-$C_6$-alkyl)carbonyloxy, ($C_2$-$C_6$-alkenyl-)carbonyl-oxy or ($C_2$-$C_6$-alkynyl)carbonyloxy, ($C_1$-$C_6$-alkyl)carbonyl-amino, ($C_2$-$C_6$-alkenyl)carbonyl-amino, ($C_2$-$C_6$-alkynyl)carbonyl-amino, wherein the carbon atoms in the aliphatic radicals of the aforementioned groups may carry any combination of 1, 2 or 3 radicals $R^a$, C(O)N$R^f R^g$, (S$O_2$)N$R^f R^g$, a radical Y-Ar, a radical Y-Hc or a radical Y-Cy, wherein Y is a single bond, oxygen, sulfur, nitrogen, NH, N$R^f$, $C_1$-$C_6$-alkandiyl, $C_1$-$C_6$-alkandiyloxy, carbonyl or carbonyloxy group;

Ar is phenyl or naphthyl, wherein Ar is unsubstituted or may carry any combination of 1 to 5 radicals $R^b$;

Hc is a mono- or bicyclic 5- to 10-membered heteroaromatic ring, which contains 1, 2, 3 or 4 heteroatoms selected from 2 oxygen, 2 sulfur and 3 nitrogen atoms as ring members, wherein Hc is unsubstituted or may carry any combination of 1 to 5 radicals $R^b$ Cy is $C_3$-$C_{12}$-cycloalkyl, which is unsubstituted or substituted with 1 to 5 radicals $R^b$ and wherein the radical(s) $R^6$ that is/are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals $R^b$ $R^a$ is selected from the group consisting of halogen, cyano, nitro, hydroxy, mercapto, amino, carboxyl, $C_3$-$C_6$-cycloalkyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylcarbonyl, $C_1$-$C_6$-alkoxycarbonyl, $C_1$-$C_6$-alkylthio, $C_1$-$C_6$-haloalkylthio, $C_1$-$C_6$-alkylsulfonyl and $C_1$-$C_6$-haloalkylsulfonyl;

$R^b$ is selected from the group consisting of halogen, cyano, nitro, hydroxy, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy, and $C_1$-$C_6$-alkylcarbonyloxy;

$R^c$ is selected from the group consisting of hydrogen, OH, N$H_2$, $C_1$-$C_6$-alkyl, $C_2$-$C_6$-alkenyl, $C_2$-$C_6$-alkynyl, $C_1$-$C_6$-alkoxy, $C_1$-$C_6$-alkylamino, di($C_1$-$C_6$-alkyl)amino, wherein the carbon atoms in these radicals may carry any combination of 1, 2 or 3 radicals $R^a$, phenyl, benzyl, 5 or 6 membered hetaryl, phenylamino, N—($C_1$-$C_6$-alkyl)-N-phenyl-amino and diphenylamino, wherein aromatic group may be unsubstituted or may carry 1, 2 or 3 substituents $R^b$;

$R^d$, $R^e$ are independently of each other selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, di($C_1$-$C_6$-alkyl)amino, wherein the carbon atoms in these groups may carry any combination of 1, 2 or 3 radicals $R^a$, phenyl, benzyl, 5 or 6 membered hetaryl, wherein the aromatic group may be unsubstituted or may carry 1, 2 or 3 substituents $R^b$ $R^f$, $R^g$ are independently of each other selected from the group consisting of hydrogen, hydroxy, amino, $C_1$-$C_6$-alkyl, $C_1$-$C_6$-haloalkyl, $C_2$-$C_6$-alkenyl and $C_2$-$C_6$-alkynyl, wherein the carbon atoms in these groups may carry any combination of 1, 2 or 3 radicals $R^a$;

phenyl, benzyl, 5 or 6 membered hetaryl, wherein aromatic group may be unsubstituted or may carry 1, 2 or 3 substituents $R^b$ $R^h$ is selected from hydrogen, $C_1$-$C_6$-alkyl, $C_2$-$C_6$-alkenyl, $C_2$-$C_6$-alkynyl, $C_1$-$C_6$-alkylamino, di($C_1$-$C_6$-alkyl)amino, $C_2$-$C_6$-alkandiylamino, $C_2$-$C_6$-alkenylamino, di($C_2$-$C_6$-alkenyl)amino, $C_2$-$C_6$-alkynylamino, di($C_2$-$C_6$-alkynyl)amino, $C_1$-$C_6$-alkoxy, $C_2$-$C_6$-alkenyloxy, $C_2$-$C_6$-alkynyloxy, $C_1$-$C_6$-alkylthio, $C_3$-$C_{12}$-cycloalkylthio, $C_2$-$C_6$-alkenylthio, $C_2$-$C_6$-alkynylthio, and wherein the carbon atoms in these groups may be substituted with 1, 2, 3, 4 or 5 radicals $R^a$;

a radical Y-Ar, a radical Y-Cy or a radical Y-Hc, wherein Y is a single bond, oxygen, sulfur, nitrogen, NH, N$R^f$, $C_1$-$C_6$-alkandiyl, $C_1$-$C_6$-alkandiyloxy, carbonyl or carbonyloxy, wherein the aliphatic carbon atoms in these groups may be unsubstituted or substituted with $R^a$;

Ar is phenyl or naphthyl, wherein Ar is unsubstituted or may carry any combination of 1 to 5 radicals $R^b$ Cy is $C_3$-$C_{12}$-cycloalkyl, which is unsubstituted or substituted with 1 to 5 radicals $R^b$ Hc is saturated or partially unsaturated 3 to 8 membered heterocycle, which contains 1, 2, 3 or 4 heteroatoms selected from oxygen, sulfur and nitrogen atoms and/or 1 or 2 heteroaromatic groups selected from S(O), S(O)$_2$ as ring members, and wherein the ring is unsubstituted or may carry 1, 2, 3 or 4 radicals $R^b$ $R^i$ are each independently selected from hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from O, S and N;

$R^j$ is selected from hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, hydrazino, ($C_1$-$C_6$-alkyl)hydrazino, di($C_1$-$C_6$-alkyl)hydrazino, phenyl and heteroaryl, which can be a mono- or bicyclic 5 to 10 membered heteroaromatic ring, which contains 1, 2, 3 or 4 heteroatoms selected from O, S and N;

or the enantiomers, diastereomers or salts thereof;

with the provisos that i) if B is C$H_2$ and A is C$H_2$, then $R^1$ is different from hydrogen, and ii) if B is C$H_2$ and A is C($R^{4.1}$)($R^{4.2}$) and $R^1$ is hydrogen, then at least one of $R^{4.1}$ and $R^{4.2}$ is different than hydrogen, and iii) if A is C($R^{4.1}$)($R^{4.2}$), then at least one of $R^4$, $R^{5.1}$, $R^{5.2}$, $R^{4.1}$ or $R^{4.2}$ is different than hydrogen.

Depending on the substitution pattern, the compounds of formula I can contain one or more chiral centers, in which case they are present as enantiomer or diastereomer mixtures. Subject matter of this invention are not only compositions containing these mixtures but also those containing the pure enantiomers or diastereomers.

Substituted amino-thiourea compounds have been described among others in BE 825 275, as well as their use as animal growth promoters and herbicides. Preparation methods for ureidotetralins have been described in DT 2505 301.

Substituted amino-thiourea compounds have further been discussed in WO 2007/060120.

The compounds of the formula I, and their agriculturally acceptable salts are highly active against animal pest, i.e. harmful arthropods and nematodes, especially against difficult to control insects and acaridae.

Accordingly, the present invention relates to substituted amino-thiourea compounds of the general formula I and to their agriculturally useful salts.

Moreover, the present invention relates to:
agricultural and veterinary compositions comprising an amount of at least one compound of the formula I or an enantiomer, diasteromer or salt thereof;
the use of a compound of formula I or an enantiomer, diasteromer or salt thereof and not comprising the provisos i) and ii), for combating animal pests;
a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of the formula I or an enantiomer, diasteromer or salt thereof and not comprising the provisos i) and ii);
a method for protecting crops from attack or infestation by animal pests, which comprises contacting a crop with a pesticidally effective amount of at least one compound of the formula I or an enantiomer, diasteromer or salt thereof and not comprising the provisos i) and ii);
a method for the protection of seeds from soil insects and of the seedlings' roots and shoots from soil and foliar insects comprising contacting the seeds before sowing and/or after pregermination with at least one compound of the formula I, or the enantiomers, diastereomers or salts thereof and not comprising the provisos i) and ii);
seeds comprising a compound of the formula I or an enantiomer, diasteromer or salt thereof and not comprising the provisos i) and ii).
the use of compounds of formula I or the enantiomers, diastereomers or veterinary acceptable salts thereof and not comprising the provisos i) and ii), for combating parasites in and on animals.
a method for treating, controlling, preventing or protecting animals against infestation or infection by parasites which comprises orally, topically or parenterally administering or applying to the animals a parasiticidally effective amount of an amino-thiourea compound of formula I or the enantiomers, diastereomers and/or veterinary acceptable salt thereof and not comprising the provisos i) and ii).
a process for the preparation of a composition for treating, controlling, preventing or protecting animals against infestation or infection by parasites which comprises a parasiticidally effective amount of an amino-thiourea compound of formula I or the enantiomers, diastereomers and/or veterinary acceptable salt thereof and not comprising the provisos i) and ii).

Salts of the compounds of the formula I are preferably agriculturally and/or veterinary acceptable salts. They can be formed in a customary method, e.g. by reacting the compound with an acid of the anion in question if the compound of formula I has a basic functionality or by reacting an acidic compound of formula I with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, di-methylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_1$-$C_4$-alkylthio-$C_1$-$C_4$-alkyl" as used herein refers to alkyl having 1 to 4 carbon atoms, wherein one hydrogen atom of the alkyl radical is replaced by a $C_1$-$C_4$-alkylthio group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "aryl-$C_1$-$C_4$-alkyl" as used herein refers to an aromatic hydrocarbon radical, which is bound to the remainder of the molecule via a $C_1$-$C_4$-alkylene group, examples comprise benzyl, 1-phenylethyl or 2-phenylethyl.

The term "3- to 7-membered heterocyclyl" as used herein (and also in "heterocyclyl-$C_1$-$C_4$-alkyl") refers to a saturated, fully or partially unsaturated or aromatic heterocyclic radicals having 3 to 7 ring members, wherein 1, 2 or 3 ring members are heteroatoms selected from O, N and S or heteroatom groups, selected from S=O, $S(O)_2$ or N—R with R being H or alkyl. Examples for non-aromatic rings include azetidiyl, pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like. Examples for aromatic rings are listed in the following paragraph.

The term "3- to 7-membered heteroaryl" as used herein (and also in "heteroaryl-$C_1$-$C_4$-alkyl") refers to an aromatic heterocyclic radical having 3 to 7 ring members, wherein 1, 2 or 3 ring members are heteroatoms selected from O, N and S or heteroatom groups, selected from S=O, S(O)$_2$ or N—R with R being H or alkyl. Examples for monocyclic 3- to 7-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl.

The terms "heterocyclyl-$C_1$-$C_4$-alkyl" as used herein refer to aromatic and non-aromatic saturated, fully or partially unsaturated heterocyclic and the terms "heteroaryl-$C_1$-$C_4$-alkyl" as used herein refer to aromatic radicals, which are both bound to the remainder of the molecule via a $C_1$-$C_4$-alkylene group.

The term "$R^2$ together with $R^1$ may be $C_1$-$C_3$-alkandiyl, $C_1$-$C_2$-alkandiylcarbonyl, $C_1$-$C_2$-alkandiylthiocarbonyl or a bridging C=O or C=S group" as used herein refers to the formation of a ring, e.g. as oxazolidine, [1,3]oxazinane, [1,3]oxazepane, morpholinone, morpholinethione, oxazolidone and oxazolidinethione.

Preferences

With respect to the use according to the invention of the substituted amino-thiourea compounds of formula I, particular preference is given to the following meanings of the substituents and variables, in each case on their own or in combination:

Preferred are substituted amino-thiourea compounds of formula (I), wherein $R^1$ is hydrogen or C(=O)$R^h$.

Preferred are substituted amino-thiourea compounds of formula (I), wherein $R^1$ is C(=S)$R^h$.

Especially preferred are substituted amino-thiourea compounds of formula (I), wherein $R^1$ is hydrogen.

Especially preferred are substituted amino-thiourea compounds of formula (I), wherein $R^1$ is C(=O)$R^h$.

Mostly preferred are substituted amino-thiourea compounds of formula (I), wherein $R^1$ is C(=O)$R^h$ and $R^h$ is $C_1$-$C_6$-alkyl, and wherein the $C_1$-$C_6$-alkyl may be unsubstituted or substituted with 1, 2, 3, 4 or 5 radicals $R^a$.

Preferred are also substituted amino-thiourea compounds of formula (I), wherein $R^1$ is C(=O)$R^h$ and $R^h$ is a radical Y-Ar or Y-Hc, and wherein Y is a single bond, oxygen or nitrogen, NH or $NR^1$, Ar is phenyl or naphthyl and Hc is pyrimidyl, pyridyl, thienyl, furyl, pyrazolyl, imidazolyl, triazolyl, thiazolyl, oxazolyl, isothiazolyl, isoxazolyl, quinolinyl, isoquinolinyl, indolyl, benzofuryl, benzthienyl, benzoxazolyl, benzthiazolyl or benzimidazolyl, and wherein the Ar or the Hc may be unsubstituted or may carry any combination of 1 to 5 radicals $R^b$.

More preferred are also substituted amino-thiourea compounds of formula (I), wherein $R^1$ is C(=O)$R^h$ and $R^h$ is a radical Y-Hc, and wherein Y is a single bond, oxygen or nitrogen, NH or $NR^1$, and Hc is selected from the group consisting of pyridyl, thienyl, furyl, pyrazolyl, imidazolyl, thiazolyl, oxazolyl, quinolinyl, benzofuryl, benzthienyl, benzoxazolyl or benzthiazolyl, and wherein the heterocyclic radicals may be unsubstituted or may carry any combination of 1, 2, 3, 4 or 5 radicals $R^b$.

Preferred are substituted amino-thiourea compounds of formula (I), wherein A is oxygen, $NR^{4.3}$, sulfur, S(O) or S(O)$_2$.

Especially preferred are substituted amino-thiourea compounds of formula (I), wherein A is $NR^{4.3}$ and $R^{4.3}$ is hydrogen, $C_1$-$C_6$-alkyl or $C_1$-$C_6$-alkylcarbonyl.

Preferred are substituted amino-thiourea compounds of formula (I), wherein A is $CR^{4.1}R^{4.2}$ and $R^{4.1}$ and $R^{4.2}$ are independently from one another hydrogen or $C_1$-$C_6$-alkyl.

Especially preferred are substituted amino-thiourea compounds of formula (I), wherein A is $CH_2$.

Preferred are substituted amino-thiourea compounds of formula (I), wherein the phenyl ring carries 1 or 2 radicals $R^6$, which are independently of each other selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio and $C_1$-$C_6$-haloalkylthio.

Especially preferred are substituted amino-thiourea compounds of formula (I), wherein the phenyl ring carries 1 or 2 radicals $R^6$, which are independently of each other selected from the group consisting of halogen, $C_1$-$C_6$-alkyl and $C_1$-$C_6$-haloalkyl.

Preferred are substituted amino-thiourea compounds of formula (I), wherein $R^{5.1}$ and $R^{5.2}$ are selected independently from one another from the group consisting of hydrogen, $C_1$-$C_6$-alkyl, $C_1$-$C_6$-alkenyl, $C_1$-$C_6$-alkynyl $C_1$-$C_6$-haloalkyl, $C_1$-$C_6$-haloalkenyl, $C_1$-$C_6$-haloalkynyl, wherein the aliphatic carbon radicals may be unsubstituted or substituted with 1, 2, 3, 4 or 5 radicals $R^a$, phenyl, benzyl, pyrimidyl, pyridyl, thienyl, furyl, pyrazolyl, imidazolyl, triazolyl, thiazolyl, oxazolyl, isothiazolyl and isoxazolyl, quinolinyl, isoquinolinyl, indolyl, benzofuryl, benzthienyl, benzoxazolyl, benzthiazolyl and benzimidazolyl and wherein the cyclic radicals may be unsubstituted or may carry any combination of 1, 2, 3, 4 or 5 radicals $R^b$.

Especially preferred are substituted amino-thiourea compounds of formula (I), wherein $R^{5.1}$ or $R^{5.2}$ are independently from one another hydrogen or $C_1$-$C_6$-alkyl, and wherein the $C_1$-$C_6$-alkyl may be unsubstituted or substituted with 1, 2, 3, 4 or 5 radicals $R^a$.

Especially preferred are also substituted amino-thiourea compounds of formula (I), wherein $R^{5.1}$ and/or $R^{5.2}$ is phenyl, and wherein the phenyl may be unsubstituted or may carry any combination of 1, 2, 3, 4 or 5 radicals $R^b$.

Especially preferred are also substituted amino-thiourea compounds of formula (I), wherein $R^{5.1}$ and/or $R^{5.2}$ is selected from the group consisting of pyridyl, thienyl, furyl, pyrazolyl, imidazolyl, thiazolyl, oxazolyl, quinolinyl, benzofuryl, benzthienyl, benzoxazolyl or benzthiazolyl and wherein the heterocyclic radicals may be unsubstituted or may carry any combination of 1, 2, 3, 4 or 5 radicals $R^b$.

Preferred are substituted amino-thiourea compounds of formula (I), wherein $R^2$ and $R^3$ are selected independently from one another from the group consisting of hydrogen, C(=O)$R^i$ and $C_1$-$C_6$-alkyl.

Especially preferred are substituted amino-thiourea compounds of formula (I), wherein $R^2$ and $R^3$ are both hydrogen.

Preferred are substituted amino-thiourea compounds of formula (I), wherein $R^4$ is selected from the group consisting of hydrogen, $C_1$-$C_6$-alkyl, $C_2$-$C_6$-alkenyl, optionally substituted phenyl and optionally substituted benzyl.

Especially preferred are substituted amino-thiourea compounds of formula (I), wherein $R^4$ is hydrogen.

Preferred are substituted amino-thiourea compounds of formula (I), wherein B is a single bond.

Preferred are also substituted amino-thiourea compounds of formula (I), wherein B is $CH_2$.

Preferred are substituted amino-thiourea compounds of formula (I), wherein n is 0.

Preferred are also substituted amino-thiourea compounds of formula (I), wherein n is 1 or 2.

Especially preferred are substituted amino-thiourea compounds of formula (I), wherein
n is 1 or 2
A is oxygen or sulfur
B is a chemical bond
$R^1$ is hydrogen or C(=O)$R^h$
$R^2$, $R^3$ are both hydrogen and
$R^6$ is halogen or $C_1$-$C_6$-alkyl.

Examples of Preferred Compounds

Examples of preferred embodiments of the present invention are illustrated by the following formulae (I.1), (I.2), (I.3), (I.4), (I.5), (I.6), (I.7), (I.8), (I.9), (I.10), (I.11), (I.12), (I.13) and (I.14).

In formulae (I.1) and (I.2) at least one of the radicals $R^{5.1}$ and $R^{5.2}$ is different from hydrogen.

In formulae (I.11), and (I.12) is $R^4$ different from hydrogen.

Furthermore in formulae (I.13) and (I.14) $R^1$ and at least one of the radicals $R^{5.1}$ and $R^{5.2}$ is different from hydrogen.

If at least one radical $R^{5.1}$, $R^{5.2}$ or $R^{4.1}$ different from hydrogen is present (e.g. in formula (I.9), the structures depicted represent any possible combination of cisoide or transoide positions of said radicals relative to the amino group and to one another.

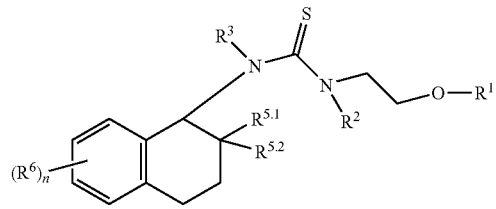
(I.1)

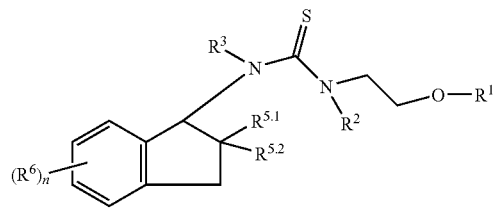
(I.2)

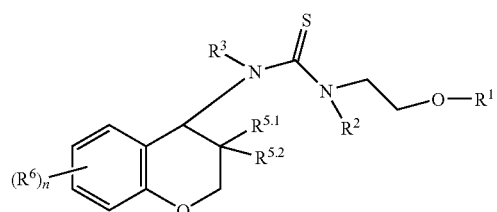
(I.3)

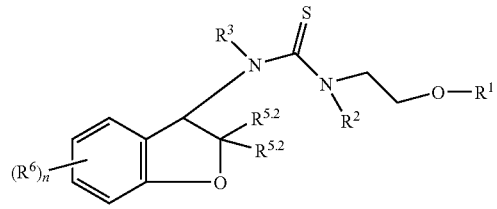
(I.4)

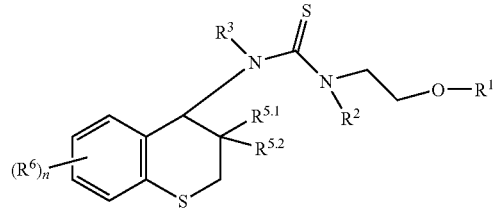
(I.5)

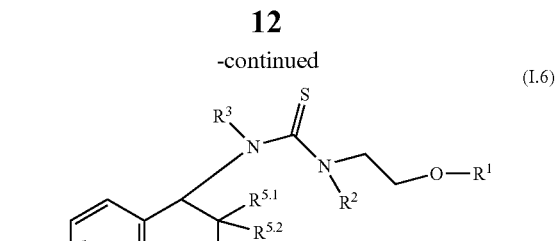
(I.6)

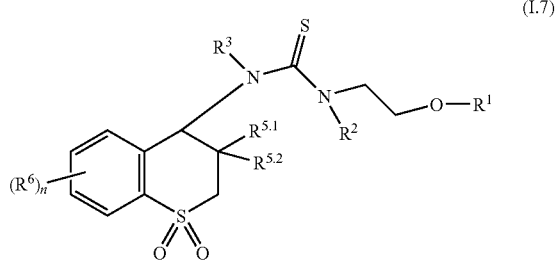
(I.7)

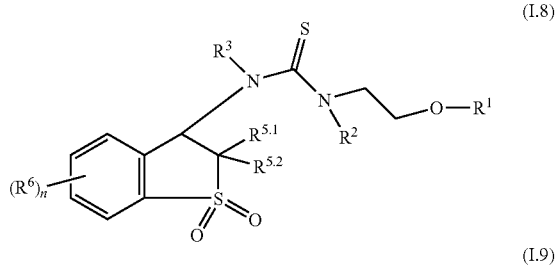
(I.8)

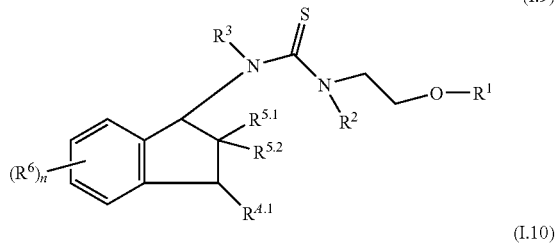
(I.9)

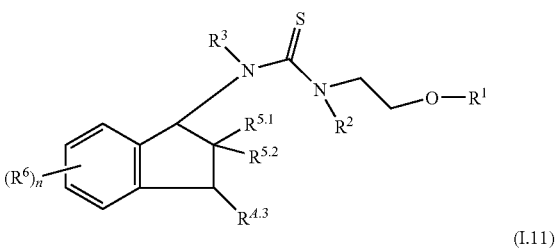
(I.10)

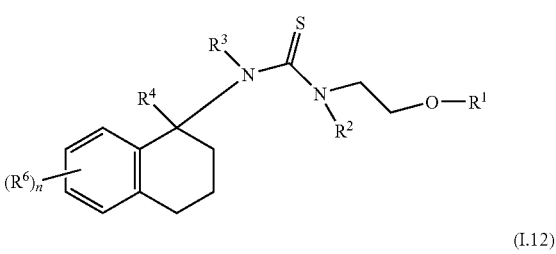
(I.11)

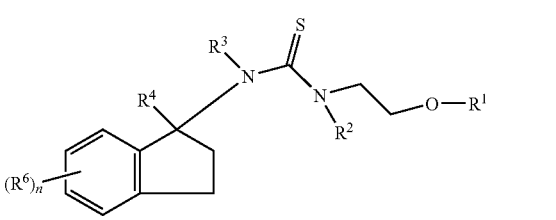
(I.12)

-continued

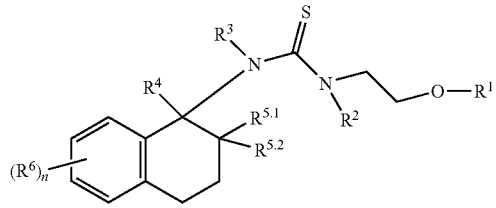
(I.13)

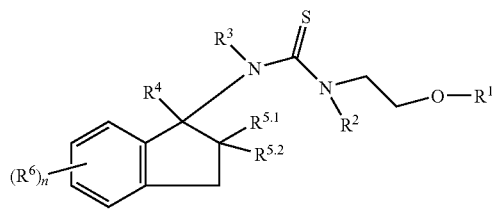
(I.14)

Examples for such preferred compounds are given in the following tables 1 to 720.

Table 1: Compounds of formula (I), wherein A is CH$_2$, R$^1$ is hydrogen, R$^2$ is hydrogen, R$^3$ is hydrogen, R$^4$ is hydrogen and wherein B, (R$^6$)$_n$, R$^{5.1}$ and R$^{5.2}$ have the meanings given in any of lines 145 to 1296 of table A.

TABLE A

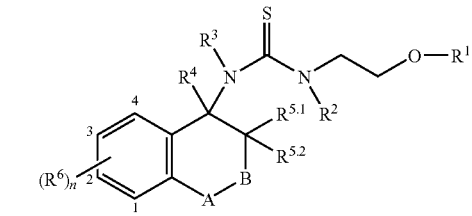
(I)

| | B | (R$^6$)$_n$ | R$^{5.1}$ | R$^{5.2}$ |
|---|---|---|---|---|
| 1 | — | 1-CH$_3$ | H | H |
| 2 | — | 2-CH$_3$ | H | H |
| 3 | — | 3-CH$_3$ | H | H |
| 4 | — | 4-CH$_3$ | H | H |
| 5 | — | 1-CH$_3$, 3-CH$_3$ | H | H |
| 6 | — | 1-CH$_3$, 3-CH$_3$, 4-CH$_3$ | H | H |
| 7 | — | 3-CH$_3$, 4-CH$_3$ | H | H |
| 8 | — | 1-Cl | H | H |
| 9 | — | 2-Cl | H | H |
| 10 | — | 3-Cl | H | H |
| 11 | — | 4-Cl | H | H |
| 12 | — | 1-Cl, 3-Cl | H | H |
| 13 | — | 1-Cl, 3-Cl, 4-Cl | H | H |
| 14 | — | 3-Cl, 4-Cl | H | H |
| 15 | — | 1-F | H | H |
| 16 | — | 2-F | H | H |
| 17 | — | 3-F | H | H |
| 18 | — | 4-F | H | H |
| 19 | — | 1-F, 3-F | H | H |
| 20 | — | 1-F, 3-F, 4-F | H | H |
| 21 | — | 3-F, 4-F | H | H |
| 22 | — | 1-Br | H | H |
| 23 | — | 2-Br | H | H |
| 24 | — | 3-Br | H | H |
| 25 | — | 4-Br | H | H |
| 26 | — | 1-Br, 3-Br | H | H |
| 27 | — | 1-Br, 3-Br, 4-Br | H | H |
| 28 | — | 3-Br, 4-Br | H | H |
| 29 | — | 1-CF$_3$ | H | H |
| 30 | — | 2-CF$_3$ | H | H |
| 31 | — | 3-CF$_3$ | H | H |
| 32 | — | 4-CF$_3$ | H | H |

TABLE A-continued

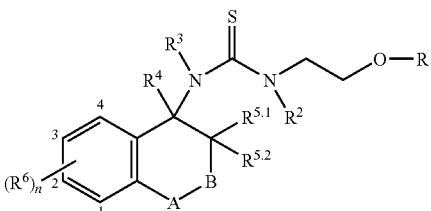
(I)

| | B | (R$^6$)$_n$ | R$^{5.1}$ | R$^{5.2}$ |
|---|---|---|---|---|
| 33 | — | 1CF$_3$, 3-CF$_3$ | H | H |
| 34 | — | 1-CF$_3$, 3-CF$_3$, 4-CF$_3$ | H | H |
| 35 | — | 3-CF$_3$, 4-CF3 | H | H |
| 36 | — | 1-OCH$_3$ | H | H |
| 37 | — | 2-OCH$_3$ | H | H |
| 38 | — | 3-OCH$_3$ | H | H |
| 39 | — | 4-OCH$_3$ | H | H |
| 40 | — | 1-OCH$_3$, 3-OCH$_3$ | H | H |
| 41 | — | 1-OCH$_3$, 3-OCH$_3$, 4-OCH$_3$ | H | H |
| 42 | — | 3,4-OCH$_3$, OCH$_3$ | H | H |
| 43 | — | 1-CH$_3$, 3-Cl | H | H |
| 44 | — | 1-Cl, 3-CH$_3$ | H | H |
| 45 | — | 1-CH$_3$, 3-F | H | H |
| 46 | — | 1-F, 3-CH$_3$ | H | H |
| 47 | — | 1-CH$_3$, 3-Br | H | H |
| 48 | — | 1-Br, 3-CH$_3$ | H | H |
| 49 | — | 1-CH$_3$, 3-CF$_3$ | H | H |
| 50 | — | 1-CF$_3$, 3-CH$_3$ | H | H |
| 51 | — | 1-CH$_3$, 3 OCH$_3$ | H | H |
| 52 | — | 1-OCH$_3$, 3-CH$_3$ | H | H |
| 53 | — | 1-Cl, 3-F | H | H |
| 54 | — | 1-F, 3-Cl | H | H |
| 55 | — | 1-Cl, 3-Br | H | H |
| 56 | — | 1-Br, 3-Cl | H | H |
| 57 | — | 1-Cl, 3-CF3 | H | H |
| 58 | — | 11-CF$_3$, 3-Cl | H | H |
| 59 | — | 1-Cl, 3-OCH$_3$ | H | H |
| 60 | — | 1-OCH$_3$, 3-Cl | H | H |
| 61 | — | 1-F, 3-Br | H | H |
| 62 | — | 1-Br, 3-F | H | H |
| 63 | — | 1-F, 3-CF$_3$ | H | H |
| 64 | — | 1-CF$_3$, 3-F | H | H |
| 65 | — | 1-F, 3-OCH$_3$ | H | H |
| 66 | — | 1-OCH$_3$, 3-F | H | H |
| 67 | — | 1-Br, 3-CF3 | H | H |
| 68 | — | 1-CF$_3$, 3-Br | H | H |
| 69 | — | 1-Br, 3-OCH$_3$ | H | H |
| 70 | — | 1-OCH$_3$, 3-Br | H | H |
| 71 | — | 1-CF$_3$, 3-OCH$_3$ | H | H |
| 72 | — | 1-OCH$_3$, 3-CF$_3$ | H | H |
| 73 | CH$_2$ | 1-CH$_3$ | H | H |
| 74 | CH$_2$ | 2-CH$_3$ | H | H |
| 75 | CH$_2$ | 3-CH$_3$ | H | H |
| 76 | CH$_2$ | 4-CH$_3$ | H | H |
| 77 | CH$_2$ | 1-CH$_3$, 3-CH$_3$ | H | H |
| 78 | CH$_2$ | 1-CH$_3$, 3-CH$_3$, 4-CH$_3$ | H | H |
| 79 | CH$_2$ | 3-CH$_3$, 4-CH$_3$ | H | H |
| 80 | CH$_2$ | 1-Cl | H | H |
| 81 | CH$_2$ | 2-Cl | H | H |
| 82 | CH$_2$ | 3-Cl | H | H |
| 83 | CH$_2$ | 4-Cl | H | H |
| 84 | CH$_2$ | 1-Cl, 3-Cl | H | H |
| 85 | CH$_2$ | 1-Cl, 3-Cl, 4-Cl | H | H |
| 86 | CH$_2$ | 3-Cl, 4-Cl | H | H |
| 87 | CH$_2$ | 1-F | H | H |
| 88 | CH$_2$ | 2-F | H | H |
| 89 | CH$_2$ | 3-F | H | H |
| 90 | CH$_2$ | 4-F | H | H |
| 91 | CH$_2$ | 1-F, 3-F | H | H |
| 92 | CH$_2$ | 1-F, 3-F, 4-F | H | H |
| 93 | CH$_2$ | 3-F, 4-F | H | H |
| 94 | CH$_2$ | 1-Br | H | H |
| 95 | CH$_2$ | 2-Br | H | H |
| 96 | CH$_2$ | 3-Br | H | H |
| 97 | CH$_2$ | 4-Br | H | H |

TABLE A-continued

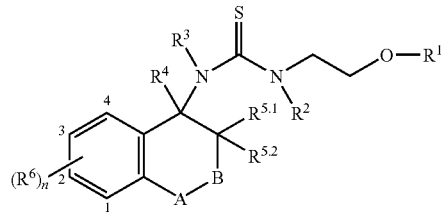

| | B | $(R^6)_n$ | $R^{5.1}$ | $R^{5.2}$ |
|---|---|---|---|---|
| 98 | $CH_2$ | 1-Br, 3-Br | H | H |
| 99 | $CH_2$ | 1-Br, 3-Br, 4-Br | H | H |
| 100 | $CH_2$ | 3-Br, 4-Br | H | H |
| 101 | $CH_2$ | 1-$CF_3$ | H | H |
| 102 | $CH_2$ | 2-$CF_3$ | H | H |
| 103 | $CH_2$ | 3-$CF_3$ | H | H |
| 104 | $CH_2$ | 4-$CF_3$ | H | H |
| 105 | $CH_2$ | 1$CF_3$, 3-$CF_3$ | H | H |
| 106 | $CH_2$ | 1-$CF_3$, 3-$CF_3$, 4-$CF_3$ | H | H |
| 107 | $CH_2$ | 3-$CF_3$, 4-$CF3$ | H | H |
| 108 | $CH_2$ | 1-$OCH_3$ | H | H |
| 109 | $CH_2$ | 2-$OCH_3$ | H | H |
| 110 | $CH_2$ | 3-$OCH_3$ | H | H |
| 111 | $CH_2$ | 4-$OCH_3$ | H | H |
| 112 | $CH_2$ | 1-$OCH_3$, 3-$OCH_3$ | H | H |
| 113 | $CH_2$ | 1-$OCH_3$, 3-$OCH_3$, 4-$OCH_3$ | H | H |
| 114 | $CH_2$ | 3,4-$OCH_3$, $OCH_3$ | H | H |
| 115 | $CH_2$ | 1-$CH_3$, 3-Cl | H | H |
| 116 | $CH_2$ | 1-Cl, 3-$CH_3$ | H | H |
| 117 | $CH_2$ | 1-Cl, 3-F | H | H |
| 118 | $CH_2$ | 1-F, 3-$CH_3$ | H | H |
| 119 | $CH_2$ | 1-$CH_3$, 3-Br | H | H |
| 120 | $CH_2$ | 1-Br, 3-$CH_3$ | H | H |
| 121 | $CH_2$ | 1-$CH_3$, 3-$CF_3$ | H | H |
| 122 | $CH_2$ | 1-$CF_3$, 3-$CH_3$ | H | H |
| 123 | $CH_2$ | 1-$CH_3$, 3 $OCH_3$ | H | H |
| 124 | $CH_2$ | 1-$OCH_3$, 3-$CH_3$ | H | H |
| 125 | $CH_2$ | 1-Cl, 3-F | H | H |
| 126 | $CH_2$ | 1-F, 3-Cl | H | H |
| 127 | $CH_2$ | 1-Cl, 3-Br | H | H |
| 128 | $CH_2$ | 1-Br, 3-Cl | H | H |
| 129 | $CH_2$ | 1-Cl, 3-CF3 | H | H |
| 130 | $CH_2$ | 11-$CF_3$, 3-Cl | H | H |
| 131 | $CH_2$ | 1-Cl, 3-$OCH_3$ | H | H |
| 132 | $CH_2$ | 1-$OCH_3$, 3-Cl | H | H |
| 133 | $CH_2$ | 1-F, 3-Br | H | H |
| 134 | $CH_2$ | 1-Br, 3-F | H | H |
| 135 | $CH_2$ | 1-F, 3-$CF_3$ | H | H |
| 136 | $CH_2$ | 1-$CF_3$, 3-F | H | H |
| 137 | $CH_2$ | 1-F, 3-$OCH_3$ | H | H |
| 138 | $CH_2$ | 1-$OCH_3$, 3-F | H | H |
| 139 | $CH_2$ | 1-Br, 3-$CF_3$ | H | H |
| 140 | $CH_2$ | 1-$CF_3$, 3-Br | H | H |
| 141 | $CH_2$ | 1-Br, 3-$OCH_3$ | H | H |
| 142 | $CH_2$ | 1-$OCH_3$, 3-Br | H | H |
| 143 | $CH_2$ | 1-$CF_3$, 3-$OCH_3$ | H | H |
| 144 | $CH_2$ | 1-$OCH_3$, 3-$CF_3$ | H | H |
| 145 | — | 1-$CH_3$ | $CH_3$ | H |
| 146 | — | 2-$CH_3$ | $CH_3$ | H |
| 147 | — | 3-$CH_3$ | $CH_3$ | H |
| 148 | — | 4-$CH_3$ | $CH_3$ | H |
| 149 | — | 1-$CH_3$, 3-$CH_3$ | $CH_3$ | H |
| 150 | — | 1-$CH_3$, 3-$CH_3$, 4-$CH_3$ | $CH_3$ | H |
| 151 | — | 3-$CH_3$, 4-$CH_3$ | $CH_3$ | H |
| 152 | — | 1-Cl | $CH_3$ | H |
| 153 | — | 2-Cl | $CH_3$ | H |
| 154 | — | 3-Cl | $CH_3$ | H |
| 155 | — | 4-Cl | $CH_3$ | H |
| 156 | — | 1-Cl, 3-Cl | $CH_3$ | H |
| 157 | — | 1-Cl, 3-Cl, 4-Cl | $CH_3$ | H |
| 158 | — | 3-Cl, 4-Cl | $CH_3$ | H |
| 159 | — | 1-F | $CH_3$ | H |
| 160 | — | 2-F | $CH_3$ | H |
| 161 | — | 3-F | $CH_3$ | H |
| 162 | — | 4-F | $CH_3$ | H |

TABLE A-continued

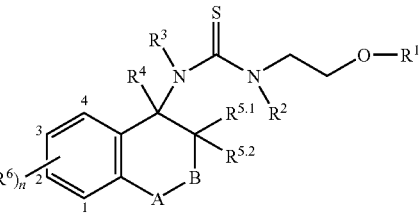

| | B | $(R^6)_n$ | $R^{5.1}$ | $R^{5.2}$ |
|---|---|---|---|---|
| 163 | — | 1-F, 3-F | $CH_3$ | H |
| 164 | — | 1-F, 3-F, 4-F | $CH_3$ | H |
| 165 | — | 3-F, 4-F | $CH_3$ | H |
| 166 | — | 1-Br | $CH_3$ | H |
| 167 | — | 2-Br | $CH_3$ | H |
| 168 | — | 3-Br | $CH_3$ | H |
| 169 | — | 4-Br | $CH_3$ | H |
| 170 | — | 1-Br, 3-Br | $CH_3$ | H |
| 171 | — | 1-Br, 3-Br, 4-Br | $CH_3$ | H |
| 172 | — | 3-Br, 4-Br | $CH_3$ | H |
| 173 | — | 1-$CF_3$ | $CH_3$ | H |
| 174 | — | 2-$CF_3$ | $CH_3$ | H |
| 175 | — | 3-$CF_3$ | $CH_3$ | H |
| 176 | — | 4-$CF_3$ | $CH_3$ | H |
| 177 | — | 1$CF_3$, 3-$CF_3$ | $CH_3$ | H |
| 178 | — | 1-$CF_3$, 3-$CF_3$, 4-$CF_3$ | $CH_3$ | H |
| 179 | — | 3-$CF_3$, 4-$CF3$ | $CH_3$ | H |
| 180 | — | 1-$OCH_3$ | $CH_3$ | H |
| 181 | — | 2-$OCH_3$ | $CH_3$ | H |
| 182 | — | 3-$OCH_3$ | $CH_3$ | H |
| 183 | — | 4-$OCH_3$ | $CH_3$ | H |
| 184 | — | 1-$OCH_3$, 3-$OCH_3$ | $CH_3$ | H |
| 185 | — | 1-$OCH_3$, 3-$OCH_3$, 4-$OCH_3$ | $CH_3$ | H |
| 186 | — | 3,4-$OCH_3$, $OCH_3$ | $CH_3$ | H |
| 187 | — | 1-$CH_3$, 3-Cl | $CH_3$ | H |
| 188 | — | 1-Cl, 3-$CH_3$ | $CH_3$ | H |
| 189 | — | 1-$CH_3$, 3-F | $CH_3$ | H |
| 190 | — | 1-F, 3-$CH_3$ | $CH_3$ | H |
| 191 | — | 1-$CH_3$, 3-Br | $CH_3$ | H |
| 192 | — | 1-Br, 3-$CH_3$ | $CH_3$ | H |
| 193 | — | 1-$CH_3$, 3-$CF_3$ | $CH_3$ | H |
| 194 | — | 1-$CF_3$, 3-$CH_3$ | $CH_3$ | H |
| 195 | — | 1-$CH_3$, 3 $OCH_3$ | $CH_3$ | H |
| 196 | — | 1-$OCH_3$, 3-$CH_3$ | $CH_3$ | H |
| 197 | — | 1-Cl, 3-F | $CH_3$ | H |
| 198 | — | 1-F, 3-Cl | $CH_3$ | H |
| 199 | — | 1-Cl, 3-Br | $CH_3$ | H |
| 200 | — | 1-Br, 3-Cl | $CH_3$ | H |
| 201 | — | 1-Cl, 3-CF3 | $CH_3$ | H |
| 202 | — | 11-$CF_3$, 3-Cl | $CH_3$ | H |
| 203 | — | 1-Cl, 3-$OCH_3$ | $CH_3$ | H |
| 204 | — | 1-$OCH_3$, 3-Cl | $CH_3$ | H |
| 205 | — | 1-F, 3-Br | $CH_3$ | H |
| 206 | — | 1-Br, 3-F | $CH_3$ | H |
| 207 | — | 1-F, 3-$CF_3$ | $CH_3$ | H |
| 208 | — | 1-$CF_3$, 3-F | $CH_3$ | H |
| 209 | — | 1-F, 3-$OCH_3$ | $CH_3$ | H |
| 210 | — | 1-$OCH_3$, 3-F | $CH_3$ | H |
| 211 | — | 1-Br, 3-CF3 | $CH_3$ | H |
| 212 | — | 1-$CF_3$, 3-Br | $CH_3$ | H |
| 213 | — | 1-Br, 3-$OCH_3$ | $CH_3$ | H |
| 214 | — | 1-$OCH_3$, 3-Br | $CH_3$ | H |
| 215 | — | 1-$CF_3$, 3-$OCH_3$ | $CH_3$ | H |
| 216 | — | 1-$OCH_3$, 3-$CF_3$ | $CH_3$ | H |
| 217 | $CH_2$ | 1-$CH_3$ | $CH_3$ | H |
| 218 | $CH_2$ | 2-$CH_3$ | $CH_3$ | H |
| 219 | $CH_2$ | 3-$CH_3$ | $CH_3$ | H |
| 220 | $CH_2$ | 4-$CH_3$ | $CH_3$ | H |
| 221 | $CH_2$ | 1-$CH_3$, 3-$CH_3$ | $CH_3$ | H |
| 222 | $CH_2$ | 1-$CH_3$, 3-$CH_3$, 4-$CH_3$ | $CH_3$ | H |
| 223 | $CH_2$ | 3-$CH_3$, 4-$CH_3$ | $CH_3$ | H |
| 224 | $CH_2$ | 1-Cl | $CH_3$ | H |
| 225 | $CH_2$ | 2-Cl | $CH_3$ | H |
| 226 | $CH_2$ | 3-Cl | $CH_3$ | H |
| 227 | $CH_2$ | 4-Cl | $CH_3$ | H |

TABLE A-continued

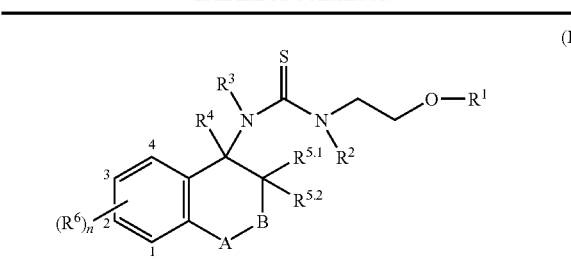

(I)

| | B | $(R^6)_n$ | $R^{5.1}$ | $R^{5.2}$ |
|---|---|---|---|---|
| 228 | CH$_2$ | 1-Cl, 3-Cl | CH$_3$ | H |
| 229 | CH$_2$ | 1-Cl, 3-Cl, 4-Cl | CH$_3$ | H |
| 230 | CH$_2$ | 3-Cl, 4-Cl | CH$_3$ | H |
| 231 | CH$_2$ | 1-F | CH$_3$ | H |
| 232 | CH$_2$ | 2-F | CH$_3$ | H |
| 233 | CH$_2$ | 3-F | CH$_3$ | H |
| 234 | CH$_2$ | 4-F | CH$_3$ | H |
| 235 | CH$_2$ | 1-F, 3-F | CH$_3$ | H |
| 236 | CH$_2$ | 1-F, 3-F, 4-F | CH$_3$ | H |
| 237 | CH$_2$ | 3-F, 4-F | CH$_3$ | H |
| 238 | CH$_2$ | 1-Br | CH$_3$ | H |
| 239 | CH$_2$ | 2-Br | CH$_3$ | H |
| 240 | CH$_2$ | 3-Br | CH$_3$ | H |
| 241 | CH$_2$ | 4-Br | CH$_3$ | H |
| 242 | CH$_2$ | 1-Br, 3-Br | CH$_3$ | H |
| 243 | CH$_2$ | 1-Br, 3-Br, 4-Br | CH$_3$ | H |
| 244 | CH$_2$ | 3-Br, 4-Br | CH$_3$ | H |
| 245 | CH$_2$ | 1-CF$_3$ | CH$_3$ | H |
| 246 | CH$_2$ | 2-CF$_3$ | CH$_3$ | H |
| 247 | CH$_2$ | 3-CF$_3$ | CH$_3$ | H |
| 248 | CH$_2$ | 4-CF$_3$ | CH$_3$ | H |
| 249 | CH$_2$ | 1CF$_3$, 3-CF$_3$ | CH$_3$ | H |
| 250 | CH$_2$ | 1-CF$_3$, 3-CF$_3$, 4-CF$_3$ | CH$_3$ | H |
| 251 | CH$_2$ | 3-CF$_3$, 4-CF3 | CH$_3$ | H |
| 252 | CH$_2$ | 1-OCH$_3$ | CH$_3$ | H |
| 253 | CH$_2$ | 2-OCH$_3$ | CH$_3$ | H |
| 254 | CH$_2$ | 3-OCH$_3$ | CH$_3$ | H |
| 255 | CH$_2$ | 4-OCH$_3$ | CH$_3$ | H |
| 256 | CH$_2$ | 1-OCH$_3$, 3-OCH$_3$ | CH$_3$ | H |
| 257 | CH$_2$ | 1-OCH$_3$, 3-OCH$_3$, 4-OCH$_3$ | CH$_3$ | H |
| 258 | CH$_2$ | 3,4-OCH$_3$, OCH$_3$ | CH$_3$ | H |
| 259 | CH$_2$ | 1-CH$_3$, 3-Cl | CH$_3$ | H |
| 260 | CH$_2$ | 1-Cl, 3-CH$_3$ | CH$_3$ | H |
| 261 | CH$_2$ | 1-CH$_3$, 3-F | CH$_3$ | H |
| 262 | CH$_2$ | 1-F, 3-CH$_3$ | CH$_3$ | H |
| 263 | CH$_2$ | 1-CH$_3$, 3-Br | CH$_3$ | H |
| 264 | CH$_2$ | 1-Br, 3-CH$_3$ | CH$_3$ | H |
| 265 | CH$_2$ | 1-CH$_3$, 3-CF$_3$ | CH$_3$ | H |
| 266 | CH$_2$ | 1-CF$_3$, 3-CH$_3$ | CH$_3$ | H |
| 267 | CH$_2$ | 1-CH$_3$, 3 OCH$_3$ | CH$_3$ | H |
| 268 | CH$_2$ | 1-OCH$_3$, 3-CH$_3$ | CH$_3$ | H |
| 269 | CH$_2$ | 1-Cl, 3-F | CH$_3$ | H |
| 270 | CH$_2$ | 1-F, 3-Cl | CH$_3$ | H |
| 271 | CH$_2$ | 1-Cl, 3-Br | CH$_3$ | H |
| 272 | CH$_2$ | 1-Br, 3-Cl | CH$_3$ | H |
| 273 | CH$_2$ | 1-Cl, 3-CF3 | CH$_3$ | H |
| 274 | CH$_2$ | 11-CF$_3$, 3-Cl | CH$_3$ | H |
| 275 | CH$_2$ | 1-Cl, 3-OCH$_3$ | CH$_3$ | H |
| 276 | CH$_2$ | 1-OCH$_3$, 3-Cl | CH$_3$ | H |
| 277 | CH$_2$ | 1-F, 3-Br | CH$_3$ | H |
| 278 | CH$_2$ | 1-Br, 3-F | CH$_3$ | H |
| 279 | CH$_2$ | 1-F, 3-CF$_3$ | CH$_3$ | H |
| 280 | CH$_2$ | 1-CF$_3$, 3-F | CH$_3$ | H |
| 281 | CH$_2$ | 1-F, 3-OCH$_3$ | CH$_3$ | H |
| 282 | CH$_2$ | 1-OCH$_3$, 3-F | CH$_3$ | H |
| 283 | CH$_2$ | 1-Br, 3-CF$_3$ | CH$_3$ | H |
| 284 | CH$_2$ | 1-CF$_3$, 3-Br | CH$_3$ | H |
| 285 | CH$_2$ | 1-Br, 3-OCH$_3$ | CH$_3$ | H |
| 286 | CH$_2$ | 1-OCH$_3$, 3-Br | CH$_3$ | H |
| 287 | CH$_2$ | 1-CF$_3$, 3-OCH$_3$ | CH$_3$ | H |
| 288 | CH$_2$ | 1-OCH$_3$, 3-CF$_3$ | CH$_3$ | H |
| 289 | — | 1-CH$_3$ | n-propenyl | H |
| 290 | — | 2-CH$_3$ | n-propenyl | H |
| 291 | — | 3-CH$_3$ | n-propenyl | H |
| 292 | — | 4-CH$_3$ | n-propenyl | H |

TABLE A-continued

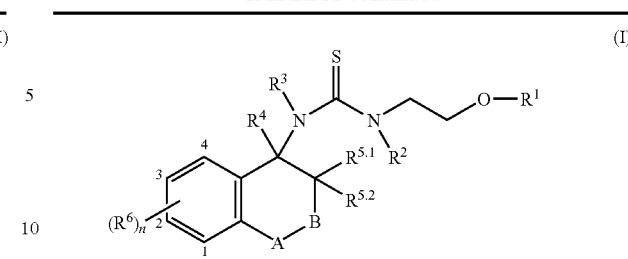

(I)

| | B | $(R^6)_n$ | $R^{5.1}$ | $R^{5.2}$ |
|---|---|---|---|---|
| 293 | — | 1-CH$_3$, 3-CH$_3$ | n-propenyl | H |
| 294 | — | 1-CH$_3$, 3-CH$_3$, 4-CH$_3$ | n-propenyl | H |
| 295 | — | 3-CH$_3$, 4-CH$_3$ | n-propenyl | H |
| 296 | — | 1-Cl | n-propenyl | H |
| 297 | — | 2-Cl | n-propenyl | H |
| 298 | — | 3-Cl | n-propenyl | H |
| 299 | — | 4-Cl | n-propenyl | H |
| 300 | — | 1-Cl, 3-Cl | n-propenyl | H |
| 301 | — | 1-Cl, 3-Cl, 4-Cl | n-propenyl | H |
| 302 | — | 3-Cl, 4-Cl | n-propenyl | H |
| 303 | — | 1-F | n-propenyl | H |
| 304 | — | 2-F | n-propenyl | H |
| 305 | — | 3-F | n-propenyl | H |
| 306 | — | 4-F | n-propenyl | H |
| 307 | — | 1-F, 3-F | n-propenyl | H |
| 308 | — | 1-F, 3-F, 4-F | n-propenyl | H |
| 309 | — | 3-F, 4-F | n-propenyl | H |
| 310 | — | 1-Br | n-propenyl | H |
| 311 | — | 2-Br | n-propenyl | H |
| 312 | — | 3-Br | n-propenyl | H |
| 313 | — | 4-Br | n-propenyl | H |
| 314 | — | 1-Br, 3-Br | n-propenyl | H |
| 315 | — | 1-Br, 3-Br, 4-Br | n-propenyl | H |
| 316 | — | 3-Br, 4-Br | n-propenyl | H |
| 317 | — | 1-CF$_3$ | n-propenyl | H |
| 318 | — | 2-CF$_3$ | n-propenyl | H |
| 319 | — | 3-CF$_3$ | n-propenyl | H |
| 320 | — | 4-CF$_3$ | n-propenyl | H |
| 321 | — | 1CF$_3$, 3-CF$_3$ | n-propenyl | H |
| 322 | — | 1-CF$_3$, 3-CF$_3$, 4-CF$_3$ | n-propenyl | H |
| 323 | — | 3-CF$_3$, 4-CF3 | n-propenyl | H |
| 324 | — | 1-OCH$_3$ | n-propenyl | H |
| 325 | — | 2-OCH$_3$ | n-propenyl | H |
| 326 | — | 3-OCH$_3$ | n-propenyl | H |
| 327 | — | 4-OCH$_3$ | n-propenyl | H |
| 328 | — | 1-OCH$_3$, 3-OCH$_3$ | n-propenyl | H |
| 329 | — | 1-OCH$_3$, 3-OCH$_3$, 4-OCH$_3$ | n-propenyl | H |
| 330 | — | 3,4-OCH$_3$, OCH$_3$ | n-propenyl | H |
| 331 | — | 1-CH$_3$, 3-Cl | n-propenyl | H |
| 332 | — | 1-Cl, 3-CH$_3$ | n-propenyl | H |
| 333 | — | 1-CH$_3$, 3-F | n-propenyl | H |
| 334 | — | 1-F, 3-CH$_3$ | n-propenyl | H |
| 335 | — | 1-CH$_3$, 3-Br | n-propenyl | H |
| 336 | — | 1-Br, 3-CH$_3$ | n-propenyl | H |
| 337 | — | 1-CH$_3$, 3-CF$_3$ | n-propenyl | H |
| 338 | — | 1-CF$_3$, 3-CH$_3$ | n-propenyl | H |
| 339 | — | 1-CH$_3$, 3 OCH$_3$ | n-propenyl | H |
| 340 | — | 1-OCH$_3$, 3-CH$_3$ | n-propenyl | H |
| 341 | — | 1-Cl, 3-F | n-propenyl | H |
| 342 | — | 1-F, 3-Cl | n-propenyl | H |
| 343 | — | 1-Cl, 3-Br | n-propenyl | H |
| 344 | — | 1-Br, 3-Cl | n-propenyl | H |
| 345 | — | 1-Cl, 3-CF3 | n-propenyl | H |
| 346 | — | 11-CF$_3$, 3-Cl | n-propenyl | H |
| 347 | — | 1-Cl, 3-OCH$_3$ | n-propenyl | H |
| 348 | — | 1-OCH$_3$, 3-Cl | n-propenyl | H |
| 349 | — | 1-F, 3-Br | n-propenyl | H |
| 350 | — | 1-Br, 3-F | n-propenyl | H |
| 351 | — | 1-F, 3-CF$_3$ | n-propenyl | H |
| 352 | — | 1-CF$_3$, 3-F | n-propenyl | H |
| 353 | — | 1-F, 3-OCH$_3$ | n-propenyl | H |
| 354 | — | 1-OCH$_3$, 3-F | n-propenyl | H |
| 355 | — | 1-Br, 3-CF3 | n-propenyl | H |
| 356 | — | 1-CF$_3$, 3-Br | n-propenyl | H |
| 357 | — | 1-Br, 3-OCH$_3$ | n-propenyl | H |

TABLE A-continued

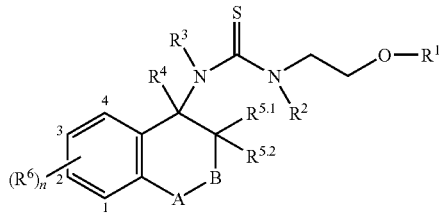

(I)

| | B | $(R^6)_n$ | $R^{5.1}$ | $R^{5.2}$ |
|---|---|---|---|---|
| 358 | — | 1-OCH₃, 3-Br | n-propenyl | H |
| 359 | — | 1-CF₃, 3-OCH₃ | n-propenyl | H |
| 360 | — | 1-OCH₃, 3-CF₃ | n-propenyl | H |
| 361 | CH₂ | 1-CH₃ | n-propenyl | H |
| 362 | CH₂ | 2-CH₃ | n-propenyl | H |
| 363 | CH₂ | 3-CH₃ | n-propenyl | H |
| 364 | CH₂ | 4-CH₃ | n-propenyl | H |
| 365 | CH₂ | 1-CH₃, 3-CH₃ | n-propenyl | H |
| 366 | CH₂ | 1-CH₃, 3-CH₃, 4-CH₃ | n-propenyl | H |
| 367 | CH₂ | 3-CH₃, 4-CH₃ | n-propenyl | H |
| 368 | CH₂ | 1-Cl | n-propenyl | H |
| 369 | CH₂ | 2-Cl | n-propenyl | H |
| 370 | CH₂ | 3-Cl | n-propenyl | H |
| 371 | CH₂ | 4-Cl | n-propenyl | H |
| 372 | CH₂ | 1-Cl, 3-Cl | n-propenyl | H |
| 373 | CH₂ | 1-Cl, 3-Cl, 4-Cl | n-propenyl | H |
| 374 | CH₂ | 3-Cl, 4-Cl | n-propenyl | H |
| 375 | CH₂ | 1-F | n-propenyl | H |
| 376 | CH₂ | 2-F | n-propenyl | H |
| 377 | CH₂ | 3-F | n-propenyl | H |
| 378 | CH₂ | 4-F | n-propenyl | H |
| 379 | CH₂ | 1-F, 3-F | n-propenyl | H |
| 380 | CH₂ | 1-F, 3-F, 4-F | n-propenyl | H |
| 381 | CH₂ | 3-F, 4-F | n-propenyl | H |
| 382 | CH₂ | 1-Br | n-propenyl | H |
| 383 | CH₂ | 2-Br | n-propenyl | H |
| 384 | CH₂ | 3-Br | n-propenyl | H |
| 385 | CH₂ | 4-Br | n-propenyl | H |
| 386 | CH₂ | 1-Br, 3-Br | n-propenyl | H |
| 387 | CH₂ | 1-Br, 3-Br, 4-Br | n-propenyl | H |
| 388 | CH₂ | 3-Br, 4-Br | n-propenyl | H |
| 389 | CH₂ | 1-CF₃ | n-propenyl | H |
| 390 | CH₂ | 2-CF₃ | n-propenyl | H |
| 391 | CH₂ | 3-CF₃ | n-propenyl | H |
| 392 | CH₂ | 4-CF₃ | n-propenyl | H |
| 393 | CH₂ | 1 CF₃, 3-CF₃ | n-propenyl | H |
| 394 | CH₂ | 1-CF₃, 3-CF₃, 4-CF₃ | n-propenyl | H |
| 395 | CH₂ | 3-CF₃, 4-CF3 | n-propenyl | H |
| 396 | CH₂ | 1-OCH₃ | n-propenyl | H |
| 397 | CH₂ | 2-OCH₃ | n-propenyl | H |
| 398 | CH₂ | 3-OCH₃ | n-propenyl | H |
| 399 | CH₂ | 4-OCH₃ | n-propenyl | H |
| 400 | CH₂ | 1-OCH₃, 3-OCH₃ | n-propenyl | H |
| 401 | CH₂ | 1-OCH₃, 3-OCH₃, 4-OCH₃ | n-propenyl | H |
| 402 | CH₂ | 3,4-OCH₃, OCH₃ | n-propenyl | H |
| 403 | CH₂ | 1-CH₃, 3-Cl | n-propenyl | H |
| 404 | CH₂ | 1-Cl, 3-CH₃ | n-propenyl | H |
| 405 | CH₂ | 1-CH₃, 3-F | n-propenyl | H |
| 406 | CH₂ | 1-F, 3-CH₃ | n-propenyl | H |
| 407 | CH₂ | 1-CH₃, 3-Br | n-propenyl | H |
| 408 | CH₂ | 1-Br, 3-CH₃ | n-propenyl | H |
| 409 | CH₂ | 1-CH₃, 3-CF₃ | n-propenyl | H |
| 410 | CH₂ | 1-CF₃, 3-CH₃ | n-propenyl | H |
| 411 | CH₂ | 1-CH₃, 3 OCH₃ | n-propenyl | H |
| 412 | CH₂ | 1-OCH₃, 3-CH₃ | n-propenyl | H |
| 413 | CH₂ | 1-Cl, 3-F | n-propenyl | H |
| 414 | CH₂ | 1-F, 3-Cl | n-propenyl | H |
| 415 | CH₂ | 1-Cl, 3-Br | n-propenyl | H |
| 416 | CH₂ | 1-Br, 3-Cl | n-propenyl | H |
| 417 | CH₂ | 1-Cl, 3-CF3 | n-propenyl | H |
| 418 | CH₂ | 11-CF₃, 3-Cl | n-propenyl | H |
| 419 | CH₂ | 1-Cl, 3-OCH₃ | n-propenyl | H |
| 420 | CH₂ | 1-OCH₃, 3-Cl | n-propenyl | H |
| 421 | CH₂ | 1-F, 3-Br | n-propenyl | H |
| 422 | CH₂ | 1-Br, 3-F | n-propenyl | H |

TABLE A-continued

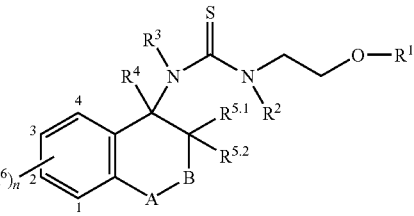

(I)

| | B | $(R^6)_n$ | $R^{5.1}$ | $R^{5.2}$ |
|---|---|---|---|---|
| 423 | CH₂ | 1-F, 3-CF₃ | n-propenyl | H |
| 424 | CH₂ | 1-CF₃, 3-F | n-propenyl | H |
| 425 | CH₂ | 1-F, 3-OCH₃ | n-propenyl | H |
| 426 | CH₂ | 1-OCH₃, 3-F | n-propenyl | H |
| 427 | CH₂ | 1-Br, 3-CF3 | n-propenyl | H |
| 428 | CH₂ | 1-CF₃, 3-Br | n-propenyl | H |
| 429 | CH₂ | 1-Br, 3-OCH₃ | n-propenyl | H |
| 430 | CH₂ | 1-OCH₃, 3-Br | n-propenyl | H |
| 431 | CH₂ | 1-CF₃, 3-OCH₃ | n-propenyl | H |
| 432 | CH₂ | 1-OCH₃, 3-CF₃ | n-propenyl | H |
| 433 | — | 1-CH₃ | benzyl | H |
| 434 | — | 2-CH₃ | benzyl | H |
| 435 | — | 3-CH₃ | benzyl | H |
| 436 | — | 4-CH₃ | benzyl | H |
| 437 | — | 1-CH₃, 3-CH₃ | benzyl | H |
| 438 | — | 1-CH₃, 3-CH₃, 4-CH₃ | benzyl | H |
| 439 | — | 3-CH₃, 4-CH₃ | benzyl | H |
| 440 | — | 1-Cl | benzyl | H |
| 441 | — | 2-Cl | benzyl | H |
| 442 | — | 3-Cl | benzyl | H |
| 443 | — | 4-Cl | benzyl | H |
| 444 | — | 1-Cl, 3-Cl | benzyl | H |
| 445 | — | 1-Cl, 3-Cl, 4-Cl | benzyl | H |
| 446 | — | 3-Cl, 4-Cl | benzyl | H |
| 447 | — | 1-F | benzyl | H |
| 448 | — | 2-F | benzyl | H |
| 449 | — | 3-F | benzyl | H |
| 450 | — | 4-F | benzyl | H |
| 451 | — | 1-F, 3-F | benzyl | H |
| 452 | — | 1-F, 3-F, 4-F | benzyl | H |
| 453 | — | 3-F, 4-F | benzyl | H |
| 454 | — | 1-Br | benzyl | H |
| 455 | — | 2-Br | benzyl | H |
| 456 | — | 3-Br | benzyl | H |
| 457 | — | 4-Br | benzyl | H |
| 458 | — | 1-Br, 3-Br | benzyl | H |
| 459 | — | 1-Br, 3-Br, 4-Br | benzyl | H |
| 460 | — | 3-Br, 4-Br | benzyl | H |
| 461 | — | 1-CF₃ | benzyl | H |
| 462 | — | 2-CF₃ | benzyl | H |
| 463 | — | 3-CF₃ | benzyl | H |
| 464 | — | 4-CF₃ | benzyl | H |
| 465 | — | 1CF₃, 3-CF₃ | benzyl | H |
| 466 | — | 1-CF₃, 3-CF₃, 4-CF₃ | benzyl | H |
| 467 | — | 3-CF₃, 4-CF3 | benzyl | H |
| 468 | — | 1-OCH₃ | benzyl | H |
| 469 | — | 2-OCH₃ | benzyl | H |
| 470 | — | 3-OCH₃ | benzyl | H |
| 471 | — | 4-OCH₃ | benzyl | H |
| 472 | — | 1-OCH₃, 3-OCH₃ | benzyl | H |
| 473 | — | 1-OCH₃, 3-OCH₃, 4-OCH₃ | benzyl | H |
| 474 | — | 3,4-OCH₃, OCH₃ | benzyl | H |
| 475 | — | 1-CH₃, 3-Cl | benzyl | H |
| 476 | — | 1-Cl, 3-CH₃ | benzyl | H |
| 477 | — | 1-CH₃, 3-F | benzyl | H |
| 478 | — | 1-F, 3-CH₃ | benzyl | H |
| 479 | — | 1-CH₃, 3-Br | benzyl | H |
| 480 | — | 1-Br, 3-CH₃ | benzyl | H |
| 481 | — | 1-CH₃, 3-CF₃ | benzyl | H |
| 482 | — | 1-CF₃, 3-CH₃ | benzyl | H |
| 483 | — | 1-CH₃, 3 OCH₃ | benzyl | H |
| 484 | — | 1-OCH₃, 3-CH₃ | benzyl | H |
| 485 | — | 1-Cl, 3-F | benzyl | H |
| 486 | — | 1-F, 3-Cl | benzyl | H |
| 487 | — | 1-Cl, 3-Br | benzyl | H |

TABLE A-continued (I)

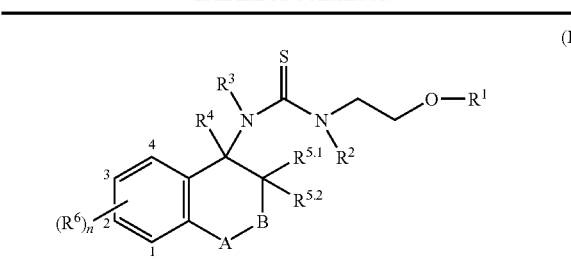

| | B | (R⁶)ₙ | R⁵·¹ | R⁵·² |
|---|---|---|---|---|
| 488 | — | 1-Br, 3-Cl | benzyl | H |
| 489 | — | 1-Cl, 3-CF3 | benzyl | H |
| 490 | — | 11-CF₃, 3-Cl | benzyl | H |
| 491 | — | 1-Cl, 3-OCH₃ | benzyl | H |
| 492 | — | 1-OCH₃, 3-Cl | benzyl | H |
| 493 | — | 1-F, 3-Br | benzyl | H |
| 494 | — | 1-Br, 3-F | benzyl | H |
| 495 | — | 1-F, 3-CF₃ | benzyl | H |
| 496 | — | 1-CF₃, 3-F | benzyl | H |
| 497 | — | 1-F, 3-OCH₃ | benzyl | H |
| 498 | — | 1-OCH₃, 3-F | benzyl | H |
| 499 | — | 1-Br, 3-CF3 | benzyl | H |
| 500 | — | 1-CF₃, 3-Br | benzyl | H |
| 501 | — | 1-Br, 3-OCH₃ | benzyl | H |
| 502 | — | 1-OCH₃, 3-Br | benzyl | H |
| 503 | — | 1-CF₃, 3-OCH₃ | benzyl | H |
| 504 | — | 1-OCH₃, 3-CF₃ | benzyl | H |
| 505 | CH₂ | 1-CH₃ | benzyl | H |
| 506 | CH₂ | 2-CH₃ | benzyl | H |
| 507 | CH₂ | 3-CH₃ | benzyl | H |
| 508 | CH₂ | 4-CH₃ | benzyl | H |
| 509 | CH₂ | 1-CH₃, 3-CH₃ | benzyl | H |
| 510 | CH₂ | 1-CH₃, 3-CH₃, 4-CH₃ | benzyl | H |
| 511 | CH₂ | 3-CH₃, 4-CH₃ | benzyl | H |
| 512 | CH₂ | 1-Cl | benzyl | H |
| 513 | CH₂ | 2-Cl | benzyl | H |
| 514 | CH₂ | 3-Cl | benzyl | H |
| 515 | CH₂ | 4-Cl | benzyl | H |
| 516 | CH₂ | 1-Cl, 3-Cl | benzyl | H |
| 517 | CH₂ | 1-Cl, 3-Cl, 4-Cl | benzyl | H |
| 518 | CH₂ | 3-Cl, 4-Cl | benzyl | H |
| 519 | CH₂ | 1-F | benzyl | H |
| 520 | CH₂ | 2-F | benzyl | H |
| 521 | CH₂ | 3-F | benzyl | H |
| 522 | CH₂ | 4-F | benzyl | H |
| 523 | CH₂ | 1-F, 3-F | benzyl | H |
| 524 | CH₂ | 1-F, 3-F, 4-F | benzyl | H |
| 525 | CH₂ | 3-F, 4-F | benzyl | H |
| 526 | CH₂ | 1-Br | benzyl | H |
| 527 | CH₂ | 2-Br | benzyl | H |
| 528 | CH₂ | 3-Br | benzyl | H |
| 529 | CH₂ | 4-Br | benzyl | H |
| 530 | CH₂ | 1-Br, 3-Br | benzyl | H |
| 531 | CH₂ | 1-Br, 3-Br, 4-Br | benzyl | H |
| 532 | CH₂ | 3-Br, 4-Br | benzyl | H |
| 533 | CH₂ | 1-CF₃ | benzyl | H |
| 534 | CH₂ | 2-CF₃ | benzyl | H |
| 535 | CH₂ | 3-CF₃ | benzyl | H |
| 536 | CH₂ | 4-CF₃ | benzyl | H |
| 537 | CH₂ | 1 CF₃, 3-CF₃ | benzyl | H |
| 538 | CH₂ | 1-CF₃, 3-CF₃, 4-CF₃ | benzyl | H |
| 539 | CH₂ | 3-CF₃, 4-CF3 | benzyl | H |
| 540 | CH₂ | 1-OCH₃ | benzyl | H |
| 541 | CH₂ | 2-OCH₃ | benzyl | H |
| 542 | CH₂ | 3-OCH₃ | benzyl | H |
| 543 | CH₂ | 4-OCH₃ | benzyl | H |
| 544 | CH₂ | 1-OCH₃, 3-OCH₃ | benzyl | H |
| 545 | CH₂ | 1-OCH₃, 3-OCH₃, 4-OCH₃ | benzyl | H |
| 546 | CH₂ | 3,4-OCH₃, OCH₃ | benzyl | H |
| 547 | CH₂ | 1-CH₃, 3-Cl | benzyl | H |
| 548 | CH₂ | 1-Cl, 3-CH₃ | benzyl | H |
| 549 | CH₂ | 1-CH₃, 3-F | benzyl | H |
| 550 | CH₂ | 1-F, 3-CH₃ | benzyl | H |
| 551 | CH₂ | 1-CH₃, 3-Br | benzyl | H |
| 552 | CH₂ | 1-Br, 3-CH₃ | benzyl | H |

TABLE A-continued (I)

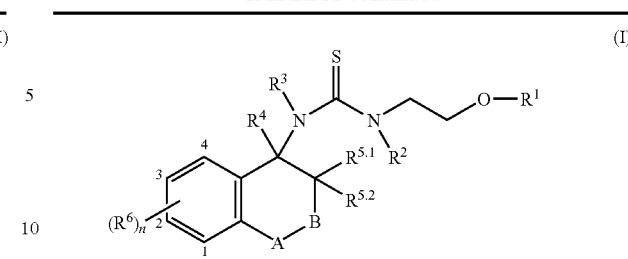

| | B | (R⁶)ₙ | R⁵·¹ | R⁵·² |
|---|---|---|---|---|
| 553 | CH₂ | 1-CH₃, 3-CF₃ | benzyl | H |
| 554 | CH₂ | 1-CF₃, 3-CH₃ | benzyl | H |
| 555 | CH₂ | 1-CH₃, 3 OCH₃ | benzyl | H |
| 556 | CH₂ | 1-OCH₃, 3-CH₃ | benzyl | H |
| 557 | CH₂ | 1-Cl, 3-F | benzyl | H |
| 558 | CH₂ | 1-F, 3-Cl | benzyl | H |
| 559 | CH₂ | 1-Cl, 3-Br | benzyl | H |
| 560 | CH₂ | 1-Br, 3-Cl | benzyl | H |
| 561 | CH₂ | 1-Cl, 3-CF3 | benzyl | H |
| 562 | CH₂ | 11-CF₃, 3-Cl | benzyl | H |
| 563 | CH₂ | 1-Cl, 3-OCH₃ | benzyl | H |
| 564 | CH₂ | 1-OCH₃, 3-Cl | benzyl | H |
| 565 | CH₂ | 1-F, 3-Br | benzyl | H |
| 566 | CH₂ | 1-Br, 3-F | benzyl | H |
| 567 | CH₂ | 1-F, 3-CF₃ | benzyl | H |
| 568 | CH₂ | 1-CF₃, 3-F | benzyl | H |
| 569 | CH₂ | 1-F, 3-OCH₃ | benzyl | H |
| 570 | CH₂ | 1-OCH₃, 3-F | benzyl | H |
| 571 | CH₂ | 1-Br, 3-CF3 | benzyl | H |
| 572 | CH₂ | 1-CF₃, 3-Br | benzyl | H |
| 573 | CH₂ | 1-Br, 3-OCH₃ | benzyl | H |
| 574 | CH₂ | 1-OCH₃, 3-Br | benzyl | H |
| 575 | CH₂ | 1-CF₃, 3-OCH₃ | benzyl | H |
| 576 | CH₂ | 1-OCH₃, 3-CF₃ | benzyl | H |
| 577 | — | 1-CH₃ | F | H |
| 578 | — | 2-CH₃ | F | H |
| 579 | — | 3-CH₃ | F | H |
| 580 | — | 4-CH₃ | F | H |
| 581 | — | 1-CH₃, 3-CH₃ | F | H |
| 582 | — | 1-CH₃, 3-CH₃, 4-CH₃ | F | H |
| 583 | — | 3-CH₃, 4-CH₃ | F | H |
| 584 | — | 1-Cl | F | H |
| 585 | — | 2-Cl | F | H |
| 586 | — | 3-Cl | F | H |
| 587 | — | 4-Cl | F | H |
| 588 | — | 1-Cl, 3-Cl | F | H |
| 589 | — | 1-Cl, 3-Cl, 4-Cl | F | H |
| 590 | — | 3-Cl, 4-Cl | F | H |
| 591 | — | 1-F | F | H |
| 592 | — | 2-F | F | H |
| 593 | — | 3-F | F | H |
| 594 | — | 4-F | F | H |
| 595 | — | 1-F, 3-F | F | H |
| 596 | — | 1-F, 3-F, 4-F | F | H |
| 597 | — | 3-F, 4-F | F | H |
| 598 | — | 1-Br | F | H |
| 599 | — | 2-Br | F | H |
| 600 | — | 3-Br | F | H |
| 601 | — | 4-Br | F | H |
| 602 | — | 1-Br, 3-Br | F | H |
| 603 | — | 1-Br, 3-Br, 4-Br | F | H |
| 604 | — | 3-Br, 4-Br | F | H |
| 605 | — | 1-CF₃ | F | H |
| 606 | — | 2-CF₃ | F | H |
| 607 | — | 3-CF₃ | F | H |
| 608 | — | 4-CF₃ | F | H |
| 609 | — | 1CF₃, 3-CF₃ | F | H |
| 610 | — | 1-CF₃, 3-CF₃, 4-CF₃ | F | H |
| 611 | — | 3-CF₃, 4-CF3 | F | H |
| 612 | — | 1-OCH₃ | F | H |
| 613 | — | 2-OCH₃ | F | H |
| 614 | — | 3-OCH₃ | F | H |
| 615 | — | 4-OCH₃ | F | H |
| 616 | — | 1-OCH₃, 3-OCH₃ | F | H |
| 617 | — | 1-OCH₃, 3-OCH₃, 4-OCH₃ | F | H |

TABLE A-continued

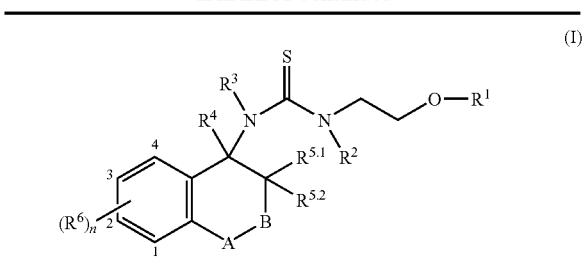

| | B | $(R^6)_n$ | $R^{5.1}$ | $R^{5.2}$ |
|---|---|---|---|---|
| 618 | — | 3,4-OCH₃, OCH₃ | F | H |
| 619 | — | 1-CH₃, 3-Cl | F | H |
| 620 | — | 1-Cl, 3-CH₃ | F | H |
| 621 | — | 1-CH₃, 3-F | F | H |
| 622 | — | 1-F, 3-CH₃ | F | H |
| 623 | — | 1-CH₃, 3-Br | F | H |
| 624 | — | 1-Br, 3-CH₃ | F | H |
| 625 | — | 1-CH₃, 3-CF₃ | F | H |
| 626 | — | 1-CF₃, 3-CH₃ | F | H |
| 627 | — | 1-CH₃, 3 OCH₃ | F | H |
| 628 | — | 1-OCH₃, 3-CH₃ | F | H |
| 629 | — | 1-Cl, 3-F | F | H |
| 630 | — | 1-F, 3-Cl | F | H |
| 631 | — | 1-Cl, 3-Br | F | H |
| 632 | — | 1-Br, 3-Cl | F | H |
| 633 | — | 1-Cl, 3-CF₃ | F | H |
| 634 | — | 11-CF₃, 3-Cl | F | H |
| 635 | — | 1-Cl, 3-OCH₃ | F | H |
| 636 | — | 1-OCH₃, 3-Cl | F | H |
| 637 | — | 1-F, 3-Br | F | H |
| 638 | — | 1-Br, 3-F | F | H |
| 639 | — | 1-F, 3-CF₃ | F | H |
| 640 | — | 1-CF₃, 3-F | F | H |
| 641 | — | 1-F, 3-OCH₃ | F | H |
| 642 | — | 1-OCH₃, 3-F | F | H |
| 643 | — | 1-Br, 3-CF₃ | F | H |
| 644 | — | 1-CF₃, 3-Br | F | H |
| 645 | — | 1-Br, 3-OCH₃ | F | H |
| 646 | — | 1-OCH₃, 3-Br | F | H |
| 647 | — | 1-CF₃, 3-OCH₃ | F | H |
| 648 | — | 1-OCH₃, 3-CF₃ | F | H |
| 649 | CH₂ | 1-CH₃ | F | H |
| 650 | CH₂ | 2-CH₃ | F | H |
| 651 | CH₂ | 3-CH₃ | F | H |
| 652 | CH₂ | 4-CH₃ | F | H |
| 653 | CH₂ | 1-CH₃, 3-CH₃ | F | H |
| 654 | CH₂ | 1-CH₃, 3-CH₃, 4-CH₃ | F | H |
| 655 | CH₂ | 3-CH₃, 4-CH₃ | F | H |
| 656 | CH₂ | 1-Cl | F | H |
| 657 | CH₂ | 2-Cl | F | H |
| 658 | CH₂ | 3-Cl | F | H |
| 659 | CH₂ | 4-Cl | F | H |
| 660 | CH₂ | 1-Cl, 3-Cl | F | H |
| 661 | CH₂ | 1-Cl, 3-Cl, 4-Cl | F | H |
| 662 | CH₂ | 3-Cl, 4-Cl | F | H |
| 663 | CH₂ | 1-F | F | H |
| 664 | CH₂ | 2-F | F | H |
| 665 | CH₂ | 3-F | F | H |
| 666 | CH₂ | 4-F | F | H |
| 667 | CH₂ | 1-F, 3-F | F | H |
| 668 | CH₂ | 1-F, 3-F, 4-F | F | H |
| 669 | CH₂ | 3-F, 4-F | F | H |
| 670 | CH₂ | 1-Br | F | H |
| 671 | CH₂ | 2-Br | F | H |
| 672 | CH₂ | 3-Br | F | H |
| 673 | CH₂ | 4-Br | F | H |
| 674 | CH₂ | 1-Br, 3-Br | F | H |
| 675 | CH₂ | 1-Br, 3-Br, 4-Br | F | H |
| 676 | CH₂ | 3-Br, 4-Br | F | H |
| 677 | CH₂ | 1-CF₃ | F | H |
| 678 | CH₂ | 2-CF₃ | F | H |
| 679 | CH₂ | 3-CF₃ | F | H |
| 680 | CH₂ | 4-CF₃ | F | H |
| 681 | CH₂ | 1CF₃, 3-CF₃ | F | H |
| 682 | CH₂ | 1-CF₃, 3-CF₃, 4-CF₃ | F | H |
| 683 | CH₂ | 3-CF₃, 4-CF3 | F | H |
| 684 | CH₂ | 1-OCH₃ | F | H |
| 685 | CH₂ | 2-OCH₃ | F | H |
| 686 | CH₂ | 3-OCH₃ | F | H |
| 687 | CH₂ | 4-OCH₃ | F | H |
| 688 | CH₂ | 1-OCH₃, 3-OCH₃ | F | H |
| 689 | CH₂ | 1-OCH₃, 3-OCH₃, 4-OCH₃ | F | H |
| 690 | CH₂ | 3,4-OCH₃, OCH₃ | F | H |
| 691 | CH₂ | 1-CH₃, 3-Cl | F | H |
| 692 | CH₂ | 1-Cl, 3-CH₃ | F | H |
| 693 | CH₂ | 1-CH₃, 3-F | F | H |
| 694 | CH₂ | 1-F, 3-CH₃ | F | H |
| 695 | CH₂ | 1-CH₃, 3-Br | F | H |
| 696 | CH₂ | 1-Br, 3-CH₃ | F | H |
| 697 | CH₂ | 1-CH₃, 3-CF₃ | F | H |
| 698 | CH₂ | 1-CF₃, 3-CH₃ | F | H |
| 699 | CH₂ | 1-CH₃, 3 OCH₃ | F | H |
| 700 | CH₂ | 1-OCH₃, 3-CH₃ | F | H |
| 701 | CH₂ | 1-Cl, 3-F | F | H |
| 702 | CH₂ | 1-F, 3-Cl | F | H |
| 703 | CH₂ | 1-Cl, 3-Br | F | H |
| 704 | CH₂ | 1-Br, 3-Cl | F | H |
| 705 | CH₂ | 1-Cl, 3-CF₃ | F | H |
| 706 | CH₂ | 11-CF₃, 3-Cl | F | H |
| 707 | CH₂ | 1-Cl, 3-OCH₃ | F | H |
| 708 | CH₂ | 1-OCH₃, 3-Cl | F | H |
| 709 | CH₂ | 1-F, 3-Br | F | H |
| 710 | CH₂ | 1-Br, 3-F | F | H |
| 711 | CH₂ | 1-F, 3-CF₃ | F | H |
| 712 | CH₂ | 1-CF₃, 3-F | F | H |
| 713 | CH₂ | 1-F, 3-OCH₃ | F | H |
| 714 | CH₂ | 1-OCH₃, 3-F | F | H |
| 715 | CH₂ | 1-Br, 3-CF₃ | F | H |
| 716 | CH₂ | 1-CF₃, 3-Br | F | H |
| 717 | CH₂ | 1-Br, 3-OCH₃ | F | H |
| 718 | CH₂ | 1-OCH₃, 3-Br | F | H |
| 719 | CH₂ | 1-CF₃, 3-OCH₃ | F | H |
| 720 | CH₂ | 1-OCH₃, 3-CF₃ | F | H |
| 721 | — | 1-CH₃ | CH₃ | CH₃ |
| 722 | — | 2-CH₃ | CH₃ | CH₃ |
| 723 | — | 3-CH₃ | CH₃ | CH₃ |
| 724 | — | 4-CH₃ | CH₃ | CH₃ |
| 725 | — | 1-CH₃, 3-CH₃ | CH₃ | CH₃ |
| 726 | — | 1-CH₃, 3-CH₃, 4-CH₃ | CH₃ | CH₃ |
| 727 | — | 3-CH₃, 4-CH₃ | CH₃ | CH₃ |
| 728 | — | 1-Cl | CH₃ | CH₃ |
| 729 | — | 2-Cl | CH₃ | CH₃ |
| 730 | — | 3-Cl | CH₃ | CH₃ |
| 731 | — | 4-Cl | CH₃ | CH₃ |
| 732 | — | 1-Cl, 3-Cl | CH₃ | CH₃ |
| 733 | — | 1-Cl, 3-Cl, 4-Cl | CH₃ | CH₃ |
| 734 | — | 3-Cl, 4-Cl | CH₃ | CH₃ |
| 735 | — | 1-F | CH₃ | CH₃ |
| 736 | — | 2-F | CH₃ | CH₃ |
| 737 | — | 3-F | CH₃ | CH₃ |
| 738 | — | 4-F | CH₃ | CH₃ |
| 739 | — | 1-F, 3-F | CH₃ | CH₃ |
| 740 | — | 1-F, 3-F, 4-F | CH₃ | CH₃ |
| 741 | — | 3-F, 4-F | CH₃ | CH₃ |
| 742 | — | 1-Br | CH₃ | CH₃ |
| 743 | — | 2-Br | CH₃ | CH₃ |
| 744 | — | 3-Br | CH₃ | CH₃ |
| 745 | — | 4-Br | CH₃ | CH₃ |
| 746 | — | 1-Br, 3-Br | CH₃ | CH₃ |
| 747 | — | 1-Br, 3-Br, 4-Br | CH₃ | CH₃ |

TABLE A-continued

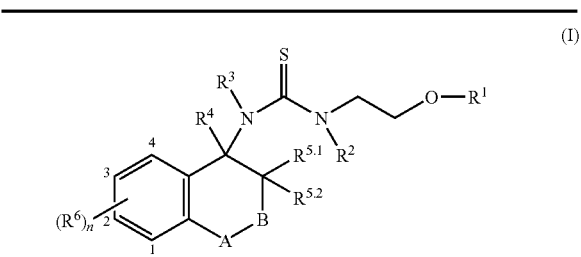

(I)

| | B | $(R^6)_n$ | $R^{5.1}$ | $R^{5.2}$ |
|---|---|---|---|---|
| 748 | — | 3-Br, 4-Br | $CH_3$ | $CH_3$ |
| 749 | — | 1-$CF_3$ | $CH_3$ | $CH_3$ |
| 750 | — | 2-$CF_3$ | $CH_3$ | $CH_3$ |
| 751 | — | 3-$CF_3$ | $CH_3$ | $CH_3$ |
| 752 | — | 4-$CF_3$ | $CH_3$ | $CH_3$ |
| 753 | — | 1$CF_3$, 3-$CF_3$ | $CH_3$ | $CH_3$ |
| 754 | — | 1-$CF_3$, 3-$CF_3$, 4-$CF_3$ | $CH_3$ | $CH_3$ |
| 755 | — | 3-$CF_3$, 4-CF3 | $CH_3$ | $CH_3$ |
| 756 | — | 1-$OCH_3$ | $CH_3$ | $CH_3$ |
| 757 | — | 2-$OCH_3$ | $CH_3$ | $CH_3$ |
| 758 | — | 3-$OCH_3$ | $CH_3$ | $CH_3$ |
| 759 | — | 4-$OCH_3$ | $CH_3$ | $CH_3$ |
| 760 | — | 1-$OCH_3$, 3-$OCH_3$ | $CH_3$ | $CH_3$ |
| 761 | — | 1-$OCH_3$, 3-$OCH_3$, 4-$OCH_3$ | $CH_3$ | $CH_3$ |
| 762 | — | 3,4-$OCH_3$, $OCH_3$ | $CH_3$ | $CH_3$ |
| 763 | — | 1-$CH_3$, 3-Cl | $CH_3$ | $CH_3$ |
| 764 | — | 1-Cl, 3-$CH_3$ | $CH_3$ | $CH_3$ |
| 765 | — | 1-$CH_3$, 3-F | $CH_3$ | $CH_3$ |
| 766 | — | 1-F, 3-$CH_3$ | $CH_3$ | $CH_3$ |
| 767 | — | 1-$CH_3$, 3-Br | $CH_3$ | $CH_3$ |
| 768 | — | 1-Br, 3-$CH_3$ | $CH_3$ | $CH_3$ |
| 769 | — | 1-$CH_3$, 3-$CF_3$ | $CH_3$ | $CH_3$ |
| 770 | — | 1-$CF_3$, 3-$CH_3$ | $CH_3$ | $CH_3$ |
| 771 | — | 1-$CH_3$, 3 $OCH_3$ | $CH_3$ | $CH_3$ |
| 772 | — | 1-$OCH_3$, 3-$CH_3$ | $CH_3$ | $CH_3$ |
| 773 | — | 1-Cl, 3-F | $CH_3$ | $CH_3$ |
| 774 | — | 1-F, 3-Cl | $CH_3$ | $CH_3$ |
| 775 | — | 1-Cl, 3-Br | $CH_3$ | $CH_3$ |
| 776 | — | 1-Br, 3-Cl | $CH_3$ | $CH_3$ |
| 777 | — | 1-Cl, 3-CF3 | $CH_3$ | $CH_3$ |
| 778 | — | 11-$CF_3$, 3-Cl | $CH_3$ | $CH_3$ |
| 779 | — | 1-Cl, 3-$OCH_3$ | $CH_3$ | $CH_3$ |
| 780 | — | 1-$OCH_3$, 3-Cl | $CH_3$ | $CH_3$ |
| 781 | — | 1-F, 3-Br | $CH_3$ | $CH_3$ |
| 782 | — | 1-Br, 3-F | $CH_3$ | $CH_3$ |
| 783 | — | 1-F, 3-$CF_3$ | $CH_3$ | $CH_3$ |
| 784 | — | 1-$CF_3$, 3-F | $CH_3$ | $CH_3$ |
| 785 | — | 1-F, 3-$OCH_3$ | $CH_3$ | $CH_3$ |
| 786 | — | 1-$OCH_3$, 3-F | $CH_3$ | $CH_3$ |
| 787 | — | 1-Br, 3-CF3 | $CH_3$ | $CH_3$ |
| 788 | — | 1-$CF_3$, 3-Br | $CH_3$ | $CH_3$ |
| 789 | — | 1-Br, 3-$OCH_3$ | $CH_3$ | $CH_3$ |
| 790 | — | 1-$OCH_3$, 3-Br | $CH_3$ | $CH_3$ |
| 791 | — | 1-$CF_3$, 3-$OCH_3$ | $CH_3$ | $CH_3$ |
| 792 | — | 1-$OCH_3$, 3-$CF_3$ | $CH_3$ | $CH_3$ |
| 793 | $CH_2$ | 1-$CH_3$ | $CH_3$ | $CH_3$ |
| 794 | $CH_2$ | 2-$CH_3$ | $CH_3$ | $CH_3$ |
| 795 | $CH_2$ | 3-$CH_3$ | $CH_3$ | $CH_3$ |
| 796 | $CH_2$ | 4-$CH_3$ | $CH_3$ | $CH_3$ |
| 797 | $CH_2$ | 1-$CH_3$, 3-$CH_3$ | $CH_3$ | $CH_3$ |
| 798 | $CH_2$ | 1-$CH_3$, 3-$CH_3$, 4-$CH_3$ | $CH_3$ | $CH_3$ |
| 799 | $CH_2$ | 3-$CH_3$, 4-$CH_3$ | $CH_3$ | $CH_3$ |
| 800 | $CH_2$ | 1-Cl | $CH_3$ | $CH_3$ |
| 801 | $CH_2$ | 2-Cl | $CH_3$ | $CH_3$ |
| 802 | $CH_2$ | 3-Cl | $CH_3$ | $CH_3$ |
| 803 | $CH_2$ | 4-Cl | $CH_3$ | $CH_3$ |
| 804 | $CH_2$ | 1-Cl, 3-Cl | $CH_3$ | $CH_3$ |
| 805 | $CH_2$ | 1-Cl, 3-Cl, 4-Cl | $CH_3$ | $CH_3$ |
| 806 | $CH_2$ | 3-Cl, 4-Cl | $CH_3$ | $CH_3$ |
| 807 | $CH_2$ | 1-F | $CH_3$ | $CH_3$ |
| 808 | $CH_2$ | 2-F | $CH_3$ | $CH_3$ |
| 809 | $CH_2$ | 3-F | $CH_3$ | $CH_3$ |
| 810 | $CH_2$ | 4-F | $CH_3$ | $CH_3$ |
| 811 | $CH_2$ | 1-F, 3-F | $CH_3$ | $CH_3$ |
| 812 | $CH_2$ | 1-F, 3-F, 4-F | $CH_3$ | $CH_3$ |
| 813 | $CH_2$ | 3-F, 4-F | $CH_3$ | $CH_3$ |
| 814 | $CH_2$ | 1-Br | $CH_3$ | $CH_3$ |
| 815 | $CH_2$ | 2-Br | $CH_3$ | $CH_3$ |
| 816 | $CH_2$ | 3-Br | $CH_3$ | $CH_3$ |
| 817 | $CH_2$ | 4-Br | $CH_3$ | $CH_3$ |
| 818 | $CH_2$ | 1-Br, 3-Br | $CH_3$ | $CH_3$ |
| 819 | $CH_2$ | 1-Br, 3-Br, 4-Br | $CH_3$ | $CH_3$ |
| 820 | $CH_2$ | 3-Br, 4-Br | $CH_3$ | $CH_3$ |
| 821 | $CH_2$ | 1-$CF_3$ | $CH_3$ | $CH_3$ |
| 822 | $CH_2$ | 2-$CF_3$ | $CH_3$ | $CH_3$ |
| 823 | $CH_2$ | 3-$CF_3$ | $CH_3$ | $CH_3$ |
| 824 | $CH_2$ | 4-$CF_3$ | $CH_3$ | $CH_3$ |
| 825 | $CH_2$ | 1$CF_3$, 3-$CF_3$ | $CH_3$ | $CH_3$ |
| 826 | $CH_2$ | 1-$CF_3$, 3-$CF_3$, 4-$CF_3$ | $CH_3$ | $CH_3$ |
| 827 | $CH_2$ | 3-$CF_3$, 4-CF3 | $CH_3$ | $CH_3$ |
| 828 | $CH_2$ | 1-$OCH_3$ | $CH_3$ | $CH_3$ |
| 829 | $CH_2$ | 2-$OCH_3$ | $CH_3$ | $CH_3$ |
| 830 | $CH_2$ | 3-$OCH_3$ | $CH_3$ | $CH_3$ |
| 831 | $CH_2$ | 4-$OCH_3$ | $CH_3$ | $CH_3$ |
| 832 | $CH_2$ | 1-$OCH_3$, 3-$OCH_3$ | $CH_3$ | $CH_3$ |
| 833 | $CH_2$ | 1-$OCH_3$, 3-$OCH_3$, 4-$OCH_3$ | $CH_3$ | $CH_3$ |
| 834 | $CH_2$ | 3,4-$OCH_3$, $OCH_3$ | $CH_3$ | $CH_3$ |
| 835 | $CH_2$ | 1-$CH_3$, 3-Cl | $CH_3$ | $CH_3$ |
| 836 | $CH_2$ | 1-Cl, 3-$CH_3$ | $CH_3$ | $CH_3$ |
| 837 | $CH_2$ | 1-$CH_3$, 3-F | $CH_3$ | $CH_3$ |
| 838 | $CH_2$ | 1-F, 3-$CH_3$ | $CH_3$ | $CH_3$ |
| 839 | $CH_2$ | 1-$CH_3$, 3-Br | $CH_3$ | $CH_3$ |
| 840 | $CH_2$ | 1-Br, 3-$CH_3$ | $CH_3$ | $CH_3$ |
| 841 | $CH_2$ | 1-$CH_3$, 3-$CF_3$ | $CH_3$ | $CH_3$ |
| 842 | $CH_2$ | 1-$CF_3$, 3-$CH_3$ | $CH_3$ | $CH_3$ |
| 843 | $CH_2$ | 1-$CH_3$, 3 $OCH_3$ | $CH_3$ | $CH_3$ |
| 844 | $CH_2$ | 1-$OCH_3$, 3-$CH_3$ | $CH_3$ | $CH_3$ |
| 845 | $CH_2$ | 1-Cl, 3-F | $CH_3$ | $CH_3$ |
| 846 | $CH_2$ | 1-F, 3-Cl | $CH_3$ | $CH_3$ |
| 847 | $CH_2$ | 1-Cl, 3-Br | $CH_3$ | $CH_3$ |
| 848 | $CH_2$ | 1-Br, 3-Cl | $CH_3$ | $CH_3$ |
| 849 | $CH_2$ | 1-Cl, 3-CF3 | $CH_3$ | $CH_3$ |
| 850 | $CH_2$ | 11-$CF_3$, 3-Cl | $CH_3$ | $CH_3$ |
| 851 | $CH_2$ | 1-Cl, 3-$OCH_3$ | $CH_3$ | $CH_3$ |
| 852 | $CH_2$ | 1-$OCH_3$, 3-Cl | $CH_3$ | $CH_3$ |
| 853 | $CH_2$ | 1-F, 3-Br | $CH_3$ | $CH_3$ |
| 854 | $CH_2$ | 1-Br, 3-F | $CH_3$ | $CH_3$ |
| 855 | $CH_2$ | 1-F, 3-$CF_3$ | $CH_3$ | $CH_3$ |
| 856 | $CH_2$ | 1-$CF_3$, 3-F | $CH_3$ | $CH_3$ |
| 857 | $CH_2$ | 1-F, 3-$OCH_3$ | $CH_3$ | $CH_3$ |
| 858 | $CH_2$ | 1-$OCH_3$, 3-F | $CH_3$ | $CH_3$ |
| 859 | $CH_2$ | 1-Br, 3-CF3 | $CH_3$ | $CH_3$ |
| 860 | $CH_2$ | 1-$CF_3$, 3-Br | $CH_3$ | $CH_3$ |
| 861 | $CH_2$ | 1-Br, 3-$OCH_3$ | $CH_3$ | $CH_3$ |
| 862 | $CH_2$ | 1-$OCH_3$, 3-Br | $CH_3$ | $CH_3$ |
| 863 | $CH_2$ | 1-$CF_3$, 3-$OCH_3$ | $CH_3$ | $CH_3$ |
| 864 | $CH_2$ | 1-$OCH_3$, 3-$CF_3$ | $CH_3$ | $CH_3$ |
| 865 | — | 1-$CH_3$ | n-propenyl | $CH_3$ |
| 866 | — | 2-$CH_3$ | n-propenyl | $CH_3$ |
| 867 | — | 3-$CH_3$ | n-propenyl | $CH_3$ |
| 868 | — | 4-$CH_3$ | n-propenyl | $CH_3$ |
| 869 | — | 1-$CH_3$, 3-$CH_3$ | n-propenyl | $CH_3$ |
| 870 | — | 1-$CH_3$, 3-$CH_3$, 4-$CH_3$ | n-propenyl | $CH_3$ |
| 871 | — | 3-$CH_3$, 4-$CH_3$ | n-propenyl | $CH_3$ |
| 872 | — | 1-Cl | n-propenyl | $CH_3$ |
| 873 | — | 2-Cl | n-propenyl | $CH_3$ |
| 874 | — | 3-Cl | n-propenyl | $CH_3$ |
| 875 | — | 4-Cl | n-propenyl | $CH_3$ |
| 876 | — | 1-Cl, 3-Cl | n-propenyl | $CH_3$ |
| 877 | — | 1-Cl, 3-Cl, 4-Cl | n-propenyl | $CH_3$ |

TABLE A-continued (I)

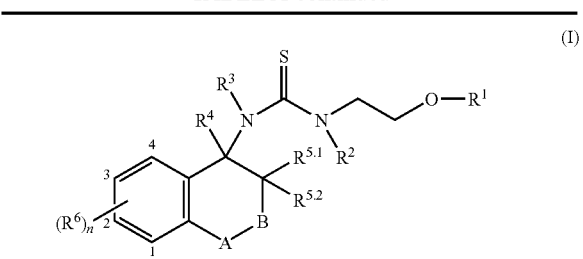

| | B | (R⁶)$_n$ | R^{5.1} | R^{5.2} |
|---|---|---|---|---|
| 878 | — | 3-Cl, 4-Cl | n-propenyl | CH$_3$ |
| 879 | — | 1-F | n-propenyl | CH$_3$ |
| 880 | — | 2-F | n-propenyl | CH$_3$ |
| 881 | — | 3-F | n-propenyl | CH$_3$ |
| 882 | — | 4-F | n-propenyl | CH$_3$ |
| 883 | — | 1-F, 3-F | n-propenyl | CH$_3$ |
| 884 | — | 1-F, 3-F, 4-F | n-propenyl | CH$_3$ |
| 885 | — | 3-F, 4-F | n-propenyl | CH$_3$ |
| 886 | — | 1-Br | n-propenyl | CH$_3$ |
| 887 | — | 2-Br | n-propenyl | CH$_3$ |
| 888 | — | 3-Br | n-propenyl | CH$_3$ |
| 889 | — | 4-Br | n-propenyl | CH$_3$ |
| 890 | — | 1-Br, 3-Br | n-propenyl | CH$_3$ |
| 891 | — | 1-Br, 3-Br, 4-Br | n-propenyl | CH$_3$ |
| 892 | — | 3-Br, 4-Br | n-propenyl | CH$_3$ |
| 893 | — | 1-CF$_3$ | n-propenyl | CH$_3$ |
| 894 | — | 2-CF$_3$ | n-propenyl | CH$_3$ |
| 895 | — | 3-CF$_3$ | n-propenyl | CH$_3$ |
| 896 | — | 4-CF$_3$ | n-propenyl | CH$_3$ |
| 897 | — | 1 CF$_3$, 3-CF$_3$ | n-propenyl | CH$_3$ |
| 898 | — | 1-CF$_3$, 3-CF$_3$, 4-CF$_3$ | n-propenyl | CH$_3$ |
| 899 | — | 3-CF$_3$, 4-CF3 | n-propenyl | CH$_3$ |
| 900 | — | 1-OCH$_3$ | n-propenyl | CH$_3$ |
| 901 | — | 2-OCH$_3$ | n-propenyl | CH$_3$ |
| 902 | — | 3-OCH$_3$ | n-propenyl | CH$_3$ |
| 903 | — | 4-OCH$_3$ | n-propenyl | CH$_3$ |
| 904 | — | 1-OCH$_3$, 3-OCH$_3$ | n-propenyl | CH$_3$ |
| 905 | — | 1-OCH$_3$, 3-OCH$_3$, 4-OCH$_3$ | n-propenyl | CH$_3$ |
| 906 | — | 3,4-OCH$_3$, OCH$_3$ | n-propenyl | CH$_3$ |
| 907 | — | 1-CH$_3$, 3-Cl | n-propenyl | CH$_3$ |
| 908 | — | 1-Cl, 3-CH$_3$ | n-propenyl | CH$_3$ |
| 909 | — | 1-CH$_3$, 3-F | n-propenyl | CH$_3$ |
| 910 | — | 1-F, 3-CH$_3$ | n-propenyl | CH$_3$ |
| 911 | — | 1-CH$_3$, 3-Br | n-propenyl | CH$_3$ |
| 912 | — | 1-Br, 3-CH$_3$ | n-propenyl | CH$_3$ |
| 913 | — | 1-CH$_3$, 3-CF$_3$ | n-propenyl | CH$_3$ |
| 914 | — | 1-CF$_3$, 3-CH$_3$ | n-propenyl | CH$_3$ |
| 915 | — | 1-CH$_3$, 3 OCH$_3$ | n-propenyl | CH$_3$ |
| 916 | — | 1-OCH$_3$, 3-CH$_3$ | n-propenyl | CH$_3$ |
| 917 | — | 1-Cl, 3-F | n-propenyl | CH$_3$ |
| 918 | — | 1-F, 3-Cl | n-propenyl | CH$_3$ |
| 919 | — | 1-Cl, 3-Br | n-propenyl | CH$_3$ |
| 920 | — | 1-Br, 3-Cl | n-propenyl | CH$_3$ |
| 921 | — | 1-Cl, 3-CF3 | n-propenyl | CH$_3$ |
| 922 | — | 11-CF$_3$, 3-Cl | n-propenyl | CH$_3$ |
| 923 | — | 1-Cl, 3-OCH$_3$ | n-propenyl | CH$_3$ |
| 924 | — | 1-OCH$_3$, 3-Cl | n-propenyl | CH$_3$ |
| 925 | — | 1-F, 3-Br | n-propenyl | CH$_3$ |
| 926 | — | 1-Br, 3-F | n-propenyl | CH$_3$ |
| 927 | — | 1-F, 3-CF$_3$ | n-propenyl | CH$_3$ |
| 928 | — | 1-CF$_3$, 3-F | n-propenyl | CH$_3$ |
| 929 | — | 1-F, 3-OCH$_3$ | n-propenyl | CH$_3$ |
| 930 | — | 1-OCH$_3$, 3-F | n-propenyl | CH$_3$ |
| 931 | — | 1-Br, 3-CF3 | n-propenyl | CH$_3$ |
| 932 | — | 1-CF$_3$, 3-Br | n-propenyl | CH$_3$ |
| 933 | — | 1-Br, 3-OCH$_3$ | n-propenyl | CH$_3$ |
| 934 | — | 1-OCH$_3$, 3-Br | n-propenyl | CH$_3$ |
| 935 | — | 1-CF$_3$, 3-OCH$_3$ | n-propenyl | CH$_3$ |
| 936 | — | 1-OCH$_3$, 3-CF$_3$ | n-propenyl | CH$_3$ |
| 937 | CH$_2$ | 1-CH$_3$ | n-propenyl | CH$_3$ |
| 938 | CH$_2$ | 2-CH$_3$ | n-propenyl | CH$_3$ |
| 939 | CH$_2$ | 3-CH$_3$ | n-propenyl | CH$_3$ |
| 940 | CH$_2$ | 4-CH$_3$ | n-propenyl | CH$_3$ |
| 941 | CH$_2$ | 1-CH$_3$, 3-CH$_3$ | n-propenyl | CH$_3$ |
| 942 | CH$_2$ | 1-CH$_3$, 3-CH$_3$, 4-CH$_3$ | n-propenyl | CH$_3$ |
| 943 | CH$_2$ | 3-CH$_3$, 4-CH$_3$ | n-propenyl | CH$_3$ |
| 944 | CH$_2$ | 1-Cl | n-propenyl | CH$_3$ |
| 945 | CH$_2$ | 2-Cl | n-propenyl | CH$_3$ |
| 946 | CH$_2$ | 3-Cl | n-propenyl | CH$_3$ |
| 947 | CH$_2$ | 4-Cl | n-propenyl | CH$_3$ |
| 948 | CH$_2$ | 1-Cl, 3-Cl | n-propenyl | CH$_3$ |
| 949 | CH$_2$ | 1-Cl, 3-Cl, 4-Cl | n-propenyl | CH$_3$ |
| 950 | CH$_2$ | 3-Cl, 4-Cl | n-propenyl | CH$_3$ |
| 951 | CH$_2$ | 1-F | n-propenyl | CH$_3$ |
| 952 | CH$_2$ | 2-F | n-propenyl | CH$_3$ |
| 953 | CH$_2$ | 3-F | n-propenyl | CH$_3$ |
| 954 | CH$_2$ | 4-F | n-propenyl | CH$_3$ |
| 955 | CH$_2$ | 1-F, 3-F | n-propenyl | CH$_3$ |
| 956 | CH$_2$ | 1-F, 3-F, 4-F | n-propenyl | CH$_3$ |
| 957 | CH$_2$ | 3-F, 4-F | n-propenyl | CH$_3$ |
| 958 | CH$_2$ | 1-Br | n-propenyl | CH$_3$ |
| 959 | CH$_2$ | 2-Br | n-propenyl | CH$_3$ |
| 960 | CH$_2$ | 3-Br | n-propenyl | CH$_3$ |
| 961 | CH$_2$ | 4-Br | n-propenyl | CH$_3$ |
| 962 | CH$_2$ | 1-Br, 3-Br | n-propenyl | CH$_3$ |
| 963 | CH$_2$ | 1-Br, 3-Br, 4-Br | n-propenyl | CH$_3$ |
| 964 | CH$_2$ | 3-Br, 4-Br | n-propenyl | CH$_3$ |
| 965 | CH$_2$ | 1-CF$_3$ | n-propenyl | CH$_3$ |
| 966 | CH$_2$ | 2-CF$_3$ | n-propenyl | CH$_3$ |
| 967 | CH$_2$ | 3-CF$_3$ | n-propenyl | CH$_3$ |
| 968 | CH$_2$ | 4-CF$_3$ | n-propenyl | CH$_3$ |
| 969 | CH$_2$ | 1 CF$_3$, 3-CF$_3$ | n-propenyl | CH$_3$ |
| 970 | CH$_2$ | 1-CF$_3$, 3-CF$_3$, 4-CF$_3$ | n-propenyl | CH$_3$ |
| 971 | CH$_2$ | 3-CF$_3$, 4-CF$_3$ | n-propenyl | CH$_3$ |
| 972 | CH$_2$ | 1-OCH$_3$ | n-propenyl | CH$_3$ |
| 973 | CH$_2$ | 2-OCH$_3$ | n-propenyl | CH$_3$ |
| 974 | CH$_2$ | 3-OCH$_3$ | n-propenyl | CH$_3$ |
| 975 | CH$_2$ | 4-OCH$_3$ | n-propenyl | CH$_3$ |
| 976 | CH$_2$ | 1-OCH$_3$, 3-OCH$_3$ | n-propenyl | CH$_3$ |
| 977 | CH$_2$ | 1-OCH$_3$, 3-OCH$_3$, 4-OCH$_3$ | n-propenyl | CH$_3$ |
| 978 | CH$_2$ | 3,4-OCH$_3$, OCH$_3$ | n-propenyl | CH$_3$ |
| 979 | CH$_2$ | 1-CH$_3$, 3-Cl | n-propenyl | CH$_3$ |
| 980 | CH$_2$ | 1-Cl, 3-CH$_3$ | n-propenyl | CH$_3$ |
| 981 | CH$_2$ | 1-CH$_3$, 3-F | n-propenyl | CH$_3$ |
| 982 | CH$_2$ | 1-F, 3-CH$_3$ | n-propenyl | CH$_3$ |
| 983 | CH$_2$ | 1-CH$_3$, 3-Br | n-propenyl | CH$_3$ |
| 984 | CH$_2$ | 1-Br, 3-CH$_3$ | n-propenyl | CH$_3$ |
| 985 | CH$_2$ | 1-CH$_3$, 3-CF$_3$ | n-propenyl | CH$_3$ |
| 986 | CH$_2$ | 1-CF$_3$, 3-CH$_3$ | n-propenyl | CH$_3$ |
| 987 | CH$_2$ | 1-CH$_3$, 3 OCH$_3$ | n-propenyl | CH$_3$ |
| 988 | CH$_2$ | 1-OCH$_3$, 3-CH$_3$ | n-propenyl | CH$_3$ |
| 989 | CH$_2$ | 1-Cl, 3-F | n-propenyl | CH$_3$ |
| 990 | CH$_2$ | 1-F, 3-Cl | n-propenyl | CH$_3$ |
| 991 | CH$_2$ | 1-Cl, 3-Br | n-propenyl | CH$_3$ |
| 992 | CH$_2$ | 1-Br, 3-Cl | n-propenyl | CH$_3$ |
| 993 | CH$_2$ | 1-Cl, 3-CF3 | n-propenyl | CH$_3$ |
| 994 | CH$_2$ | 11-CF$_3$, 3-Cl | n-propenyl | CH$_3$ |
| 995 | CH$_2$ | 1-Cl, 3-OCH$_3$ | n-propenyl | CH$_3$ |
| 996 | CH$_2$ | 1-OCH$_3$, 3-Cl | n-propenyl | CH$_3$ |
| 997 | CH$_2$ | 1-F, 3-Br | n-propenyl | CH$_3$ |
| 998 | CH$_2$ | 1-Br, 3-F | n-propenyl | CH$_3$ |
| 999 | CH$_2$ | 1-F, 3-CF$_3$ | n-propenyl | CH$_3$ |
| 1000 | CH$_2$ | 1-CF$_3$, 3-F | n-propenyl | CH$_3$ |
| 1001 | CH$_2$ | 1-F, 3-OCH$_3$ | n-propenyl | CH$_3$ |
| 1002 | CH$_2$ | 1-OCH$_3$, 3-F | n-propenyl | CH$_3$ |
| 1003 | CH$_2$ | 1-Br, 3-CF3 | n-propenyl | CH$_3$ |
| 1004 | CH$_2$ | 1-CF$_3$, 3-Br | n-propenyl | CH$_3$ |
| 1005 | CH$_2$ | 1-Br, 3-OCH$_3$ | n-propenyl | CH$_3$ |
| 1006 | CH$_2$ | 1-OCH$_3$, 3-Br | n-propenyl | CH$_3$ |
| 1007 | CH$_2$ | 1-CF$_3$, 3-OCH$_3$ | n-propenyl | CH$_3$ |

TABLE A-continued (I)

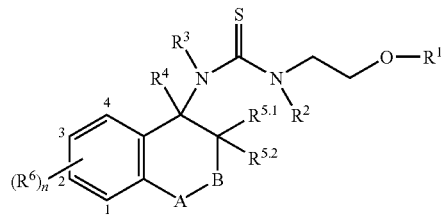 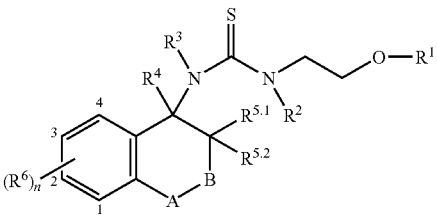

| | B | $(R^6)_n$ | $R^{5.1}$ | $R^{5.2}$ |
|---|---|---|---|---|
| 1008 | CH$_2$ | 1-OCH$_3$, 3-CF$_3$ | n-propenyl | CH$_3$ |
| 1009 | — | 1-CH$_3$ | benzyl | CH$_3$ |
| 1010 | — | 2-CH$_3$ | benzyl | CH$_3$ |
| 1011 | — | 3-CH$_3$ | benzyl | CH$_3$ |
| 1012 | — | 4-CH$_3$ | benzyl | CH$_3$ |
| 1013 | — | 1-CH$_3$, 3-CH$_3$ | benzyl | CH$_3$ |
| 1014 | — | 1-CH$_3$, 3-CH$_3$, 4-CH$_3$ | benzyl | CH$_3$ |
| 1015 | — | 3-CH$_3$, 4-CH$_3$ | benzyl | CH$_3$ |
| 1016 | — | 1-Cl | benzyl | CH$_3$ |
| 1017 | — | 2-Cl | benzyl | CH$_3$ |
| 1018 | — | 3-Cl | benzyl | CH$_3$ |
| 1019 | — | 4-Cl | benzyl | CH$_3$ |
| 1020 | — | 1-Cl, 3-Cl | benzyl | CH$_3$ |
| 1021 | — | 1-Cl, 3-Cl, 4-Cl | benzyl | CH$_3$ |
| 1022 | — | 3-Cl, 4-Cl | benzyl | CH$_3$ |
| 1023 | — | 1-F | benzyl | CH$_3$ |
| 1024 | — | 2-F | benzyl | CH$_3$ |
| 1025 | — | 3-F | benzyl | CH$_3$ |
| 1026 | — | 4-F | benzyl | CH$_3$ |
| 1027 | — | 1-F, 3-F | benzyl | CH$_3$ |
| 1028 | — | 1-F, 3-F, 4-F | benzyl | CH$_3$ |
| 1029 | — | 3-F, 4-F | benzyl | CH$_3$ |
| 1030 | — | 1-Br | benzyl | CH$_3$ |
| 1031 | — | 2-Br | benzyl | CH$_3$ |
| 1032 | — | 3-Br | benzyl | CH$_3$ |
| 1033 | — | 4-Br | benzyl | CH$_3$ |
| 1034 | — | 1-Br, 3-Br | benzyl | CH$_3$ |
| 1035 | — | 1-Br, 3-Br, 4-Br | benzyl | CH$_3$ |
| 1036 | — | 3-Br, 4-Br | benzyl | CH$_3$ |
| 1037 | — | 1-CF$_3$ | benzyl | CH$_3$ |
| 1038 | — | 2-CF$_3$ | benzyl | CH$_3$ |
| 1039 | — | 3-CF$_3$ | benzyl | CH$_3$ |
| 1040 | — | 4-CF$_3$ | benzyl | CH$_3$ |
| 1041 | — | 1CF$_3$, 3-CF$_3$ | benzyl | CH$_3$ |
| 1042 | — | 1-CF$_3$, 3-CF$_3$, 4-CF$_3$ | benzyl | CH$_3$ |
| 1043 | — | 3-CF$_3$, 4-CF3 | benzyl | CH$_3$ |
| 1044 | — | 1-OCH$_3$ | benzyl | CH$_3$ |
| 1045 | — | 2-OCH$_3$ | benzyl | CH$_3$ |
| 1046 | — | 3-OCH$_3$ | benzyl | CH$_3$ |
| 1047 | — | 4-OCH$_3$ | benzyl | CH$_3$ |
| 1048 | — | 1-OCH$_3$, 3-OCH$_3$ | benzyl | CH$_3$ |
| 1049 | — | 1-OCH$_3$, 3-OCH$_3$, 4-OCH$_3$ | benzyl | CH$_3$ |
| 1050 | — | 3,4-OCH$_3$, OCH$_3$ | benzyl | CH$_3$ |
| 1051 | — | 1-CH$_3$, 3-Cl | benzyl | CH$_3$ |
| 1052 | — | 1-Cl, 3-CH$_3$ | benzyl | CH$_3$ |
| 1053 | — | 1-CH$_3$, 3-F | benzyl | CH$_3$ |
| 1054 | — | 1-F, 3-CH$_3$ | benzyl | CH$_3$ |
| 1055 | — | 1-CH$_3$, 3-Br | benzyl | CH$_3$ |
| 1056 | — | 1-Br, 3-CH$_3$ | benzyl | CH$_3$ |
| 1057 | — | 1-CH$_3$, 3-CF$_3$ | benzyl | CH$_3$ |
| 1058 | — | 1-CF$_3$, 3-CH$_3$ | benzyl | CH$_3$ |
| 1059 | — | 1-CH$_3$, 3 OCH$_3$ | benzyl | CH$_3$ |
| 1060 | — | 1-OCH$_3$, 3-CH$_3$ | benzyl | CH$_3$ |
| 1061 | — | 1-Cl, 3-F | benzyl | CH$_3$ |
| 1062 | — | 1-F, 3-Cl | benzyl | CH$_3$ |
| 1063 | — | 1-Cl, 3-Br | benzyl | CH$_3$ |
| 1064 | — | 1-Br, 3-Cl | benzyl | CH$_3$ |
| 1065 | — | 1-Cl, 3-CF3 | benzyl | CH$_3$ |
| 1066 | — | 11-CF$_3$, 3-Cl | benzyl | CH$_3$ |
| 1067 | — | 1-Cl, 3-OCH$_3$ | benzyl | CH$_3$ |
| 1068 | — | 1-OCH$_3$, 3-Cl | benzyl | CH$_3$ |
| 1069 | — | 1-F, 3-Br | benzyl | CH$_3$ |
| 1070 | — | 1-Br, 3-F | benzyl | CH$_3$ |
| 1071 | — | 1-F, 3-CF$_3$ | benzyl | CH$_3$ |
| 1072 | — | 1-CF$_3$, 3-F | benzyl | CH$_3$ |
| 1073 | — | 1-F, 3-OCH$_3$ | benzyl | CH$_3$ |
| 1074 | — | 1-OCH$_3$, 3-F | benzyl | CH$_3$ |
| 1075 | — | 1-Br, 3-CF3 | benzyl | CH$_3$ |
| 1076 | — | 1-CF$_3$, 3-Br | benzyl | CH$_3$ |
| 1077 | — | 1-Br, 3-OCH$_3$ | benzyl | CH$_3$ |
| 1078 | — | 1-OCH$_3$, 3-Br | benzyl | CH$_3$ |
| 1079 | — | 1-CF$_3$, 3-OCH$_3$ | benzyl | CH$_3$ |
| 1080 | — | 1-OCH$_3$, 3-CF$_3$ | benzyl | CH$_3$ |
| 1081 | CH$_2$ | 1-CH$_3$ | benzyl | CH$_3$ |
| 1082 | CH$_2$ | 2-CH$_3$ | benzyl | CH$_3$ |
| 1083 | CH$_2$ | 3-CH$_3$ | benzyl | CH$_3$ |
| 1084 | CH$_2$ | 4-CH$_3$ | benzyl | CH$_3$ |
| 1085 | CH$_2$ | 1-CH$_3$, 3-CH$_3$ | benzyl | CH$_3$ |
| 1086 | CH$_2$ | 1-CH$_3$, 3-CH$_3$, 4-CH$_3$ | benzyl | CH$_3$ |
| 1087 | CH$_2$ | 3-CH$_3$, 4-CH$_3$ | benzyl | CH$_3$ |
| 1088 | CH$_2$ | 1-Cl | benzyl | CH$_3$ |
| 1089 | CH$_2$ | 2-Cl | benzyl | CH$_3$ |
| 1090 | CH$_2$ | 3-Cl | benzyl | CH$_3$ |
| 1091 | CH$_2$ | 4-Cl | benzyl | CH$_3$ |
| 1092 | CH$_2$ | 1-Cl, 3-Cl | benzyl | CH$_3$ |
| 1093 | CH$_2$ | 1-Cl, 3-Cl, 4-Cl | benzyl | CH$_3$ |
| 1094 | CH$_2$ | 3-Cl, 4-Cl | benzyl | CH$_3$ |
| 1095 | CH$_2$ | 1-F | benzyl | CH$_3$ |
| 1096 | CH$_2$ | 2-F | benzyl | CH$_3$ |
| 1097 | CH$_2$ | 3-F | benzyl | CH$_3$ |
| 1098 | CH$_2$ | 4-F | benzyl | CH$_3$ |
| 1099 | CH$_2$ | 1-F, 3-F | benzyl | CH$_3$ |
| 1100 | CH$_2$ | 1-F, 3-F, 4-F | benzyl | CH$_3$ |
| 1101 | CH$_2$ | 3-F, 4-F | benzyl | CH$_3$ |
| 1102 | CH$_2$ | 1-Br | benzyl | CH$_3$ |
| 1103 | CH$_2$ | 2-Br | benzyl | CH$_3$ |
| 1104 | CH$_2$ | 3-Br | benzyl | CH$_3$ |
| 1105 | CH$_2$ | 4-Br | benzyl | CH$_3$ |
| 1106 | CH$_2$ | 1-Br, 3-Br | benzyl | CH$_3$ |
| 1107 | CH$_2$ | 1-Br, 3-Br, 4-Br | benzyl | CH$_3$ |
| 1108 | CH$_2$ | 3-Br, 4-Br | benzyl | CH$_3$ |
| 1109 | CH$_2$ | 1-CF$_3$ | benzyl | CH$_3$ |
| 1110 | CH$_2$ | 2-CF$_3$ | benzyl | CH$_3$ |
| 1111 | CH$_2$ | 3-CF$_3$ | benzyl | CH$_3$ |
| 1112 | CH$_2$ | 4-CF$_3$ | benzyl | CH$_3$ |
| 1113 | CH$_2$ | 1CF$_3$, 3-CF$_3$ | benzyl | CH$_3$ |
| 1114 | CH$_2$ | 1-CF$_3$, 3-CF$_3$, 4-CF$_3$ | benzyl | CH$_3$ |
| 1115 | CH$_2$ | 3-CF$_3$, 4-CF3 | benzyl | CH$_3$ |
| 1116 | CH$_2$ | 1-OCH$_3$ | benzyl | CH$_3$ |
| 1117 | CH$_2$ | 2-OCH$_3$ | benzyl | CH$_3$ |
| 1118 | CH$_2$ | 3-OCH$_3$ | benzyl | CH$_3$ |
| 1119 | CH$_2$ | 4-OCH$_3$ | benzyl | CH$_3$ |
| 1120 | CH$_2$ | 1-OCH$_3$, 3-OCH$_3$ | benzyl | CH$_3$ |
| 1121 | CH$_2$ | 1-OCH$_3$, 3-OCH$_3$, 4-OCH$_3$ | benzyl | CH$_3$ |
| 1122 | CH$_2$ | 3,4-OCH$_3$, OCH$_3$ | benzyl | CH$_3$ |
| 1123 | CH$_2$ | 1-CH$_3$, 3-Cl | benzyl | CH$_3$ |
| 1124 | CH$_2$ | 1-Cl, 3-CH$_3$ | benzyl | CH$_3$ |
| 1125 | CH$_2$ | 1-CH$_3$, 3-F | benzyl | CH$_3$ |
| 1126 | CH$_2$ | 1-F, 3-CH$_3$ | benzyl | CH$_3$ |
| 1127 | CH$_2$ | 1-CH$_3$, 3-Br | benzyl | CH$_3$ |
| 1128 | CH$_2$ | 1-Br, 3-CH$_3$ | benzyl | CH$_3$ |
| 1129 | CH$_2$ | 1-CH$_3$, 3-CF$_3$ | benzyl | CH$_3$ |
| 1130 | CH$_2$ | 1-CF$_3$, 3-CH$_3$ | benzyl | CH$_3$ |
| 1131 | CH$_2$ | 1-CH$_3$, 3 OCH$_3$ | benzyl | CH$_3$ |
| 1132 | CH$_2$ | 1-OCH$_3$, 3-CH$_3$ | benzyl | CH$_3$ |
| 1133 | CH$_2$ | 1-Cl, 3-F | benzyl | CH$_3$ |
| 1134 | CH$_2$ | 1-F, 3-Cl | benzyl | CH$_3$ |
| 1135 | CH$_2$ | 1-Cl, 3-Br | benzyl | CH$_3$ |
| 1136 | CH$_2$ | 1-Br, 3-Cl | benzyl | CH$_3$ |
| 1137 | CH$_2$ | 1-Cl, 3-CF3 | benzyl | CH$_3$ |

TABLE A-continued

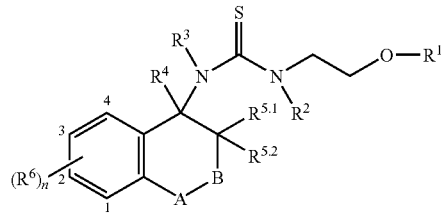

| | B | $(R^6)_n$ | $R^{5.1}$ | $R^{5.2}$ |
|---|---|---|---|---|
| 1138 | $CH_2$ | 11-$CF_3$, 3-Cl | benzyl | $CH_3$ |
| 1139 | $CH_2$ | 1-Cl, 3-$OCH_3$ | benzyl | $CH_3$ |
| 1140 | $CH_2$ | 1-$OCH_3$, 3-Cl | benzyl | $CH_3$ |
| 1141 | $CH_2$ | 1-F, 3-Br | benzyl | $CH_3$ |
| 1142 | $CH_2$ | 1-Br, 3-F | benzyl | $CH_3$ |
| 1143 | $CH_2$ | 1-F, 3-$CF_3$ | benzyl | $CH_3$ |
| 1144 | $CH_2$ | 1-$CF_3$, 3-F | benzyl | $CH_3$ |
| 1145 | $CH_2$ | 1-F, 3-$OCH_3$ | benzyl | $CH_3$ |
| 1146 | $CH_2$ | 1-$OCH_3$, 3-F | benzyl | $CH_3$ |
| 1147 | $CH_2$ | 1-Br, 3-CF3 | benzyl | $CH_3$ |
| 1148 | $CH_2$ | 1-$CF_3$, 3-Br | benzyl | $CH_3$ |
| 1149 | $CH_2$ | 1-Br, 3-$OCH_3$ | benzyl | $CH_3$ |
| 1150 | $CH_2$ | 1-$OCH_3$, 3-Br | benzyl | $CH_3$ |
| 1151 | $CH_2$ | 1-$CF_3$, 3-$OCH_3$ | benzyl | $CH_3$ |
| 1152 | $CH_2$ | 1-$OCH_3$, 3-$CF_3$ | benzyl | $CH_3$ |
| 1153 | — | 1-$CH_3$ | F | F |
| 1154 | — | 2-$CH_3$ | F | F |
| 1155 | — | 3-$CH_3$ | F | F |
| 1156 | — | 4-$CH_3$ | F | F |
| 1157 | — | 1-$CH_3$, 3-$CH_3$ | F | F |
| 1158 | — | 1-$CH_3$, 3-$CH_3$, 4-$CH_3$ | F | F |
| 1159 | — | 3-$CH_3$, 4-$CH_3$ | F | F |
| 1160 | — | 1-Cl | F | F |
| 1161 | — | 2-Cl | F | F |
| 1162 | — | 3-Cl | F | F |
| 1163 | — | 4-Cl | F | F |
| 1164 | — | 1-Cl, 3-Cl | F | F |
| 1165 | — | 1-Cl, 3-Cl, 4-Cl | F | F |
| 1166 | — | 3-Cl, 4-Cl | F | F |
| 1167 | — | 1-F | F | F |
| 1168 | — | 2-F | F | F |
| 1169 | — | 3-F | F | F |
| 1170 | — | 4-F | F | F |
| 1171 | — | 1-F, 3-F | F | F |
| 1172 | — | 1-F, 3-F, 4-F | F | F |
| 1173 | — | 3-F, 4-F | F | F |
| 1174 | — | 1-Br | F | F |
| 1175 | — | 2-Br | F | F |
| 1176 | — | 3-Br | F | F |
| 1177 | — | 4-Br | F | F |
| 1178 | — | 1-Br, 3-Br | F | F |
| 1179 | — | 1-Br, 3-Br, 4-Br | F | F |
| 1180 | — | 3-Br, 4-Br | F | F |
| 1181 | — | 1-$CF_3$ | F | F |
| 1182 | — | 2-$CF_3$ | F | F |
| 1183 | — | 3-$CF_3$ | F | F |
| 1184 | — | 4-$CF_3$ | F | F |
| 1185 | — | 1$CF_3$, 3-$CF_3$ | F | F |
| 1186 | — | 1-$CF_3$, 3-$CF_3$, 4-$CF_3$ | F | F |
| 1187 | — | 3-$CF_3$, 4-CF3 | F | F |
| 1188 | — | 1-$OCH_3$ | F | F |
| 1189 | — | 2-$OCH_3$ | F | F |
| 1190 | — | 3-$OCH_3$ | F | F |
| 1191 | — | 4-$OCH_3$ | F | F |
| 1192 | — | 1-$OCH_3$, 3-$OCH_3$ | F | F |
| 1193 | — | 1-$OCH_3$, 3-$OCH_3$, 4-$OCH_3$ | F | F |
| 1194 | — | 3,4-$OCH_3$, $OCH_3$ | F | F |
| 1195 | — | 1-$CH_3$, 3-Cl | F | F |
| 1196 | — | 1-Cl, 3-$CH_3$ | F | F |
| 1197 | — | 1-$CH_3$, 3-F | F | F |
| 1198 | — | 1-F, 3-$CH_3$ | F | F |
| 1199 | — | 1-$CH_3$, 3-Br | F | F |
| 1200 | — | 1-Br, 3-$CH_3$ | F | F |
| 1201 | — | 1-$CH_3$, 3-$CF_3$ | F | F |
| 1202 | — | 1-$CF_3$, 3-$CH_3$ | F | F |

TABLE A-continued

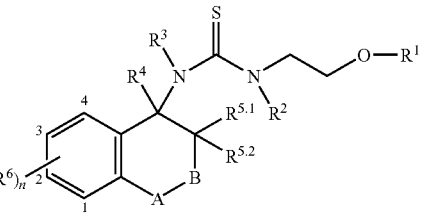

| | B | $(R^6)_n$ | $R^{5.1}$ | $R^{5.2}$ |
|---|---|---|---|---|
| 1203 | — | 1-$CH_3$, 3 $OCH_3$ | F | F |
| 1204 | — | 1-$OCH_3$, 3-$CH_3$ | F | F |
| 1205 | — | 1-Cl, 3-F | F | F |
| 1206 | — | 1-F, 3-Cl | F | F |
| 1207 | — | 1-Cl, 3-Br | F | F |
| 1208 | — | 1-Br, 3-Cl | F | F |
| 1209 | — | 1-Cl, 3-$CF_3$ | F | F |
| 1210 | — | 11-$CF_3$, 3-Cl | F | F |
| 1211 | — | 1-Cl, 3-$OCH_3$ | F | F |
| 1212 | — | 1-$OCH_3$, 3-Cl | F | F |
| 1213 | — | 1-F, 3-Br | F | F |
| 1214 | — | 1-Br, 3-F | F | F |
| 1215 | — | 1-F, 3-$CF_3$ | F | F |
| 1216 | — | 1-$CF_3$, 3-F | F | F |
| 1217 | — | 1-F, 3-$OCH_3$ | F | F |
| 1218 | — | 1-$OCH_3$, 3-F | F | F |
| 1219 | — | 1-Br, 3-$CF_3$ | F | F |
| 1220 | — | 1-$CF_3$, 3-Br | F | F |
| 1221 | — | 1-Br, 3-$OCH_3$ | F | F |
| 1222 | — | 1-$OCH_3$, 3-Br | F | F |
| 1223 | — | 1-$CF_3$, 3-$OCH_3$ | F | F |
| 1224 | — | 1-$OCH_3$, 3-$CF_3$ | F | F |
| 1225 | $CH_2$ | 1-$CH_3$ | F | F |
| 1226 | $CH_2$ | 2-$CH_3$ | F | F |
| 1227 | $CH_2$ | 3-$CH_3$ | F | F |
| 1228 | $CH_2$ | 4-$CH_3$ | F | F |
| 1229 | $CH_2$ | 1-$CH_3$, 3-$CH_3$ | F | F |
| 1230 | $CH_2$ | 1-$CH_3$, 3-$CH_3$, 4-$CH_3$ | F | F |
| 1231 | $CH_2$ | 3-$CH_3$, 4-$CH_3$ | F | F |
| 1232 | $CH_2$ | 1-Cl | F | F |
| 1233 | $CH_2$ | 2-Cl | F | F |
| 1234 | $CH_2$ | 3-Cl | F | F |
| 1235 | $CH_2$ | 4-Cl | F | F |
| 1236 | $CH_2$ | 1-Cl, 3-Cl | F | F |
| 1237 | $CH_2$ | 1-Cl, 3-Cl, 4-Cl | F | F |
| 1238 | $CH_2$ | 3-Cl, 4-Cl | F | F |
| 1239 | $CH_2$ | 1-F | F | F |
| 1240 | $CH_2$ | 2-F | F | F |
| 1241 | $CH_2$ | 3-F | F | F |
| 1242 | $CH_2$ | 4-F | F | F |
| 1243 | $CH_2$ | 1-F, 3-F | F | F |
| 1244 | $CH_2$ | 1-F, 3-F, 4-F | F | F |
| 1245 | $CH_2$ | 3-F, 4-F | F | F |
| 1246 | $CH_2$ | 1-Br | F | F |
| 1247 | $CH_2$ | 2-Br | F | F |
| 1248 | $CH_2$ | 3-Br | F | F |
| 1249 | $CH_2$ | 4-Br | F | F |
| 1250 | $CH_2$ | 1-Br, 3-Br | F | F |
| 1251 | $CH_2$ | 1-Br, 3-Br, 4-Br | F | F |
| 1252 | $CH_2$ | 3-Br, 4-Br | F | F |
| 1253 | $CH_2$ | 1-$CF_3$ | F | F |
| 1254 | $CH_2$ | 2-$CF_3$ | F | F |
| 1255 | $CH_2$ | 3-$CF_3$ | F | F |
| 1256 | $CH_2$ | 4-$CF_3$ | F | F |
| 1257 | $CH_2$ | 1$CF_3$, 3-$CF_3$ | F | F |
| 1258 | $CH_2$ | 1-$CF_3$, 3-$CF_3$, 4-$CF_3$ | F | F |
| 1259 | $CH_2$ | 3-$CF_3$, 4-CF3 | F | F |
| 1260 | $CH_2$ | 1-$OCH_3$ | F | F |
| 1261 | $CH_2$ | 2-$OCH_3$ | F | F |
| 1262 | $CH_2$ | 3-$OCH_3$ | F | F |
| 1263 | $CH_2$ | 4-$OCH_3$ | F | F |
| 1264 | $CH_2$ | 1-$OCH_3$, 3-$OCH_3$ | F | F |
| 1265 | $CH_2$ | 1-$OCH_3$, 3-$OCH_3$, 4-$OCH_3$ | F | F |
| 1266 | $CH_2$ | 3,4-$OCH_3$, $OCH_3$ | F | F |
| 1267 | $CH_2$ | 1-$CH_3$, 3-Cl | F | F |

TABLE A-continued (I)

[Structure of formula (I) showing a bicyclic system with substituents R³, R⁴, N, S, N, R⁵·¹, R², R⁵·², O-R¹, (R⁶)ₙ, and ring positions 1, 2, 3, 4, A, B]

| | B | $(R^6)_n$ | $R^{5.1}$ | $R^{5.2}$ |
|---|---|---|---|---|
| 1268 | $CH_2$ | 1-Cl, 3-$CH_3$ | F | F |
| 1269 | $CH_2$ | 1-$CH_3$, 3-F | F | F |
| 1270 | $CH_2$ | 1-F, 3-$CH_3$ | F | F |
| 1271 | $CH_2$ | 1-$CH_3$, 3-Br | F | F |
| 1272 | $CH_2$ | 1-Br, 3-$CH_3$ | F | F |
| 1273 | $CH_2$ | 1-$CH_3$, 3-$CF_3$ | F | F |
| 1274 | $CH_2$ | 1-$CF_3$, 3-$CH_3$ | F | F |
| 1275 | $CH_2$ | 1-$CH_3$, 3 $OCH_3$ | F | F |
| 1276 | $CH_2$ | 1-$OCH_3$, 3-$CH_3$ | F | F |
| 1277 | $CH_2$ | 1-Cl, 3-F | F | F |
| 1278 | $CH_2$ | 1-F, 3-Cl | F | F |
| 1279 | $CH_2$ | 1-Cl, 3-Br | F | F |
| 1280 | $CH_2$ | 1-Br, 3-Cl | F | F |
| 1281 | $CH_2$ | 1-Cl, 3-$CF_3$ | F | F |
| 1282 | $CH_2$ | 11-$CF_3$, 3-Cl | F | F |
| 1283 | $CH_2$ | 1-Cl, 3-$OCH_3$ | F | F |
| 1284 | $CH_2$ | 1-$OCH_3$, 3-Cl | F | F |
| 1285 | $CH_2$ | 1-F, 3-Br | F | F |
| 1286 | $CH_2$ | 1-Br, 3-F | F | F |
| 1287 | $CH_2$ | 1-F, 3-$CF_3$ | F | F |
| 1288 | $CH_2$ | 1-$CF_3$, 3-F | F | F |
| 1289 | $CH_2$ | 1-F, 3-$OCH_3$ | F | F |
| 1290 | $CH_2$ | 1-$OCH_3$, 3-F | F | F |
| 1291 | $CH_2$ | 1-Br, 3-$CF_3$ | F | F |
| 1292 | $CH_2$ | 1-$CF_3$, 3-Br | F | F |
| 1293 | $CH_2$ | 1-Br, 3-$OCH_3$ | F | F |
| 1294 | $CH_2$ | 1-$OCH_3$, 3-Br | F | F |
| 1295 | $CH_2$ | 1-$CF_3$, 3-$OCH_3$ | F | F |
| 1296 | $CH_2$ | 1-$OCH_3$, 3-$CF_3$ | F | F | in table A the sign "-" has the meaning of B being a single bond; the numbers in the definition of $(R^6)_n$ indicates the position the radicals are attached to the aromatic ring.

Table 2 Compounds of formula (I), wherein A is O, $R^1$ is hydrogen, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 3 Compounds of formula (I), wherein A is S, $R^1$ is hydrogen, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 4 Compounds of formula (I), wherein A is S(O), $R^1$ is hydrogen, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 5 Compounds of formula (I), wherein A is $S(O)_2$, $R^1$ is hydrogen, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 6 Compounds of formula (I), wherein A is NH, $R^1$ is hydrogen, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 7 Compounds of formula (I), wherein A is $NCH_3$, $R^1$ is hydrogen, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 8 Compounds of formula (I), wherein A is $CHC_6H_5$, $R^1$ is hydrogen, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 9 Compounds of formula (I), wherein A is $CH_2$, $R^1$ is hydrogen, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 10 Compounds of formula (I), wherein A is O, $R^1$ is hydrogen, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 11 Compounds of formula (I), wherein A is S, $R^1$ is hydrogen, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 12 Compounds of formula (I), wherein A is S(O), $R^1$ is hydrogen, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 13 Compounds of formula (I), wherein A is $S(O)_2$, $R^1$ is hydrogen, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 14 Compounds of formula (I), wherein A is NH, $R^1$ is hydrogen, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 15 Compounds of formula (I), wherein A is $NCH_3$, $R^1$ is hydrogen, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 16 Compounds of formula (I), wherein A is $CHC_6H_5$, $R^1$ is hydrogen, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 17 Compounds of formula (I), wherein A is $CH_2$, $R^1$ is hydrogen, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 18 Compounds of formula (I), wherein A is O, $R^1$ is hydrogen, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 19 Compounds of formula (I), wherein A is S, $R^1$ is hydrogen, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 20 Compounds of formula (I), wherein A is S(O), $R^1$ is hydrogen, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 21 Compounds of formula (I), wherein A is $S(O)_2$, $R^1$ is hydrogen, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 22 Compounds of formula (I), wherein A is NH, $R^1$ is hydrogen, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 23 Compounds of formula (I), wherein A is $NCH_3$, $R^1$ is hydrogen, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 24 Compounds of formula (I), wherein A is CHC$_6$H$_5$, R$^1$ is hydrogen, R$^2$ is hydrogen, R$^3$ is hydrogen, R$^4$ is phenyl and wherein B, R$^{5.1}$, R$^{5.2}$ and (R$^6$)$_n$ have the meanings given in one line of table A.

Table 25 Compounds of formula (I), wherein A is CH$_2$, R$^1$ is hydrogen, R$^2$ is hydrogen, R$^3$ is hydrogen, R$^4$ is benzyl and wherein B, R$^{5.1}$, R$^{5.2}$ and (R$^6$)$_n$ have the meanings given in one line of table A.

Table 26 Compounds of formula (I), wherein A is O, R$^1$ is hydrogen, R$^2$ is hydrogen, R$^3$ is hydrogen, R$^4$ is benzyl and wherein B, R$^{5.1}$, R$^{5.2}$ and (R$^6$)$_n$ have the meanings given in one line of table A.

Table 27 Compounds of formula (I), wherein A is S, R$^1$ is hydrogen, R$^2$ is hydrogen, R$^3$ is hydrogen, R$^4$ is benzyl and wherein B, R$^{5.1}$, R$^5$ and (R$^6$)$_n$ have the meanings given in one line of table A.

Table 28 Compounds of formula (I), wherein A is S(O), R$^1$ is hydrogen, R$^2$ is hydrogen, R$^3$ is hydrogen, R$^4$ is benzyl and wherein B, R$^{5.1}$, R$^{5.2}$ and (R$^6$)$_n$ have the meanings given in one line of table A.

Table 29 Compounds of formula (I), wherein A is S(O)$_2$, R$^1$ is hydrogen, R$^2$ is hydrogen, R$^3$ is hydrogen, R$^4$ is benzyl and wherein B, R$^{5.1}$, R$^{5.2}$ and (R$^6$)$_n$ have the meanings given in one line of table A.

Table 30 Compounds of formula (I), wherein A is NH, R$^1$ is hydrogen, R$^2$ is hydrogen, R$^3$ is hydrogen, R$^4$ is benzyl and wherein B, R$^{5.1}$, R$^{5.2}$ and (R$^6$)$_n$ have the meanings given in one line of table A.

Table 31 Compounds of formula (I), wherein A is NCH$_3$, R$^1$ is hydrogen, R$^2$ is hydrogen, R$^3$ is hydrogen, R$^4$ is benzyl and wherein B, R$^{5.1}$, R$^{5.2}$ and (R$^6$)$_n$ have the meanings given in one line of table A.

Table 32 Compounds of formula (I), wherein A is CHC$_6$H$_5$, R$^1$ is hydrogen, R$^2$ is hydrogen, R$^3$ is hydrogen, R$^4$ is benzyl and wherein B, R$^{5.1}$, R$^{5.2}$ and (R$^6$)$_n$ have the meanings given in one line of table A.

Table 33 Compounds of formula (I), wherein A is CH$_2$, R$^1$ is hydrogen, R$^2$ is hydrogen, R$^3$ is hydrogen, R$^4$ is allyl and wherein B, R$^{5.1}$, R$^{5.2}$ and (R$^6$)$_n$ have the meanings given in one line of table A.

Table 34 Compounds of formula (I), wherein A is O, R$^1$ is hydrogen, R$^2$ is hydrogen, R$^3$ is hydrogen, R$^4$ is allyl and wherein B, R$^{5.1}$, R$^{5.2}$ and (R$^6$)$_n$ have the meanings given in one line of table A.

Table 35 Compounds of formula (I), wherein A is S, R$^1$ is hydrogen, R$^2$ is hydrogen, R$^3$ is hydrogen, R$^4$ is allyl and wherein B, R$^{5.1}$, R$^{5.2}$ and (R$^6$)$_n$ have the meanings given in one line of table A.

Table 36 Compounds of formula (I), wherein A is S(O), R$^1$ is hydrogen, R$^2$ is hydrogen, R$^3$ is hydrogen, R$^4$ is allyl and wherein B, R$^{5.1}$, R$^{5.2}$ and (R$^6$)$_n$ have the meanings given in one line of table A.

Table 37 Compounds of formula (I), wherein A is S(O)$_2$, R$^1$ is hydrogen, R$^2$ is hydrogen, R$^3$ is hydrogen, R$^4$ is allyl and wherein B, R$^{5.1}$, R$^{5.2}$ and (R$^6$)$_n$ have the meanings given in one line of table A.

Table 38 Compounds of formula (I), wherein A is NH, R$^1$ is hydrogen, R$^2$ is hydrogen, R$^3$ is hydrogen, R$^4$ is allyl and wherein B, R$^{5.1}$, R$^{5.2}$ and (R$^6$)$_n$ have the meanings given in one line of table A.

Table 39 Compounds of formula (I), wherein A is NCH$_3$, R$^1$ is hydrogen, R$^2$ is hydrogen, R$^3$ is hydrogen, R$^4$ is allyl and wherein B, R$^{5.1}$, R$^{5.2}$ and (R$^6$)$_n$ have the meanings given in one line of table A.

Table 40 Compounds of formula (I), wherein A is CHC$_6$H$_5$, R$^1$ is hydrogen, R$^2$ is hydrogen, R$^3$ is hydrogen, R$^4$ is allyl and wherein B, R$^{5.1}$, R$^{5.2}$ and (R$^6$)$_n$ have the meanings given in one line of table A.

Table 41 Compounds of formula (I), wherein A is CH$_2$, R$^1$ is hydrogen, R$^2$ is CH$^3$, R$^3$ is hydrogen, R$^4$ is hydrogen and wherein B, R$^{5.1}$, R$^{5.2}$ and (R$^6$)$_n$ have the meanings given in any of lines 145 to 1296 of table A Table 42 Compounds of formula (I), wherein A is O, R$^1$ is hydrogen, R$^2$ is CH$^3$, R$^3$ is hydrogen, R$^4$ is hydrogen and wherein B, R$^{5.1}$, R$^{5.2}$ and (R$^6$)$_n$ have the meanings given in one line of table A.

Table 43 Compounds of formula (I), wherein A is S, R$^1$ is hydrogen, R$^2$ is CH$^3$, R$^3$ is hydrogen, R$^4$ is hydrogen and wherein B, R$^{5.1}$, R$^{5.2}$ and (R$^6$)$_n$ have the meanings given in one line of table A.

Table 44 Compounds of formula (I), wherein A is S(O), R$^1$ is hydrogen, R$^2$ is CH$^3$, R$^3$ is hydrogen, R$^4$ is hydrogen and wherein B, R$^{5.1}$, R$^{5.2}$ and (R$^6$)$_n$ have the meanings given in one line of table A.

Table 45 Compounds of formula (I), wherein A is S(O)$_2$, R$^1$ is hydrogen, R$^2$ is CH$^3$, R$^3$ is hydrogen, R$^4$ is hydrogen and wherein B, R$^{5.1}$, R$^{5.2}$ and (R$^6$)$_n$ have the meanings given in one line of table A.

Table 46 Compounds of formula (I), wherein A is NH, R$^1$ is hydrogen, R$^2$ is CH$^3$, R$^3$ is hydrogen, R$^4$ is hydrogen and wherein B, R$^{5.1}$, R$^{5.2}$ and (R$^6$)$_n$ have the meanings given in one line of table A.

Table 47 Compounds of formula (I), wherein A is NCH$_3$, R$^1$ is hydrogen, R$^2$ is CH$^3$, R$^3$ is hydrogen, R$^4$ is hydrogen and wherein B, R$^{5.1}$, R$^{5.2}$ and (R$^6$)$_n$ have the meanings given in one line of table A.

Table 48 Compounds of formula (I), wherein A is CHC$_6$H$_5$, R$^1$ is hydrogen, R$^2$ is CH$^3$, R$^3$ is hydrogen, R$^4$ is hydrogen and wherein B, R$^{5.1}$, R$^{5.2}$ and (R$^6$)$_n$ have the meanings given in one line of table A.

Table 49 Compounds of formula (I), wherein A is CH$_2$, R$^1$ is hydrogen, R$^2$ is CH$_3$, R$^3$ is hydrogen, R$^4$ is CH$_3$ and wherein B, R$^{5.1}$, R$^{5.2}$ and (R$^6$)$_n$ have the meanings given in one line of table A.

Table 50 Compounds of formula (I), wherein A is O, R$^1$ is hydrogen, R$^2$ is CH$_3$, R$^3$ is hydrogen, R$^4$ is CH$_3$ and wherein B, R$^{5.1}$, R$^{5.2}$ and (R$^6$)$_n$ have the meanings given in one line of table A.

Table 51 Compounds of formula (I), wherein A is S, R$^1$ is hydrogen, R$^2$ is CH$_3$, R$^3$ is hydrogen, R$^4$ is CH$_3$ and wherein B, R$^{5.1}$, R$^{5.2}$ and (R$^6$)$_n$ have the meanings given in one line of table A.

Table 52 Compounds of formula (I), wherein A is S(O), R$^1$ is hydrogen, R$^2$ is CH$_3$, R$^3$ is hydrogen, R$^4$ is CH$_3$ and wherein B, R$^{5.1}$, R$^{5.2}$ and (R$^6$)$_n$ have the meanings given in one line of table A.

Table 53 Compounds of formula (I), wherein A is S(O)$_2$, R$^1$ is hydrogen, R$^2$ is CH$_3$, R$^3$ is hydrogen, R$^4$ is CH$_3$ and wherein B, R$^{5.1}$, R$^{5.2}$ and (R$^6$)$_n$ have the meanings given in one line of table A.

Table 54 Compounds of formula (I), wherein A is NH, R$^1$ is hydrogen, R$^2$ is CH$_3$, R$^3$ is hydrogen, R$^4$ is CH$_3$ and wherein B, R$^{5.1}$, R$^{5.2}$ and (R$^6$)$_n$ have the meanings given in one line of table A.

Table 55 Compounds of formula (I), wherein A is NCH$_3$, R$^1$ is hydrogen, R$^2$ is CH$_3$, R$^3$ is hydrogen, R$^4$ is CH$_3$ and wherein B, R$^{5.1}$, R$^{5.2}$ and (R$^6$)$_n$ have the meanings given in one line of table A.

Table 56 Compounds of formula (I), wherein A is CHC$_6$H$_5$, R$^1$ is hydrogen, R$^2$ is CH$_3$, R$^3$ is hydrogen, R$^4$ is CH$_3$ and wherein B, R$^{5.1}$, R$^{5.2}$ and (R$^6$)$_n$ have the meanings given in one line of table A.

Table 57 Compounds of formula (I), wherein A is CH$_2$, R$^1$ is hydrogen, R$^2$ is CH$_3$, R$^3$ is hydrogen, R$^4$ is phenyl and wherein B, R$^{5.1}$, R$^{5.2}$ and (R$^6$)$_n$ have the meanings given in one line of table A.

Table 58 Compounds of formula (I), wherein A is O, R$^1$ is hydrogen, R$^2$ is CH$_3$, R$^3$ is hydrogen, R$^4$ is phenyl and wherein B, R$^{5.1}$, R$^{5.2}$ and (R$^6$)$_n$ have the meanings given in one line of table A.

Table 59 Compounds of formula (I), wherein A is S, R$^1$ is hydrogen, R$^2$ is CH$_3$, R$^3$ is hydrogen, R$^4$ is phenyl and wherein B, R$^{5.1}$, R$^{5.2}$ and (R$^6$)$_n$ have the meanings given in one line of table A.

Table 60 Compounds of formula (I), wherein A is S(O), R$^1$ is hydrogen, R$^2$ is CH$_3$, R$^3$ is hydrogen, R$^4$ is phenyl and wherein B, R$^{5.1}$, R$^{5.2}$ and (R$^6$)$_n$ have the meanings given in one line of table A.

Table 61 Compounds of formula (I), wherein A is S(O)$_2$, R$^1$ is hydrogen, R$^2$ is CH$_3$, R$^3$ is hydrogen, R$^4$ is phenyl and wherein B, R$^{5.1}$, R$^{5.2}$ and (R$^6$)$_n$ have the meanings given in one line of table A.

Table 62 Compounds of formula (I), wherein A is NH, R$^1$ is hydrogen, R$^2$ is CH$_3$, R$^3$ is hydrogen, R$^4$ is phenyl and wherein B, R$^{5.1}$, R$^{5.2}$ and (R$^6$)$_n$ have the meanings given in one line of table A.

Table 63 Compounds of formula (I), wherein A is NCH$_3$, R$^1$ is hydrogen, R$^2$ is CH$_3$, R$^3$ is hydrogen, R$^4$ is phenyl and wherein B, R$^{5.1}$, R$^{5.2}$ and (R$^6$)$_n$ have the meanings given in one line of table A.

Table 64 Compounds of formula (I), wherein A is CHC$_6$H$_5$, R$^1$ is hydrogen, R$^2$ is CH$_3$, R$^3$ is hydrogen, R$^4$ is phenyl and wherein B, R$^{5.1}$, R$^{5.2}$ and (R$^6$)$_n$ have the meanings given in one line of table A.

Table 65 Compounds of formula (I), wherein A is CH$_2$, R$^1$ is hydrogen, R$^2$ is CH$_3$, R$^3$ is hydrogen, R$^4$ is benzyl and wherein B, R$^{5.1}$, R$^{5.2}$ and (R$^6$)$_n$ have the meanings given in one line of table A.

Table 66 Compounds of formula (I), wherein A is O, R$^1$ is hydrogen, R$^2$ is CH$_3$, R$^3$ is hydrogen, R$^4$ is benzyl and wherein B, R$^{5.1}$, R$^{5.2}$ and (R$^6$)$_n$ have the meanings given in one line of table A.

Table 67 Compounds of formula (I), wherein A is S, R$^1$ is hydrogen, R$^2$ is CH$_3$, R$^3$ is hydrogen, R$^4$ is benzyl and wherein B, R$^{5.1}$, R$^{5.2}$ and (R$^6$)$_n$ have the meanings given in one line of table A.

Table 68 Compounds of formula (I), wherein A is S(O), R$^1$ is hydrogen, R$^2$ is CH$_3$, R$^3$ is hydrogen, R$^4$ is benzyl and wherein B, R$^{5.1}$, R$^{5.2}$ and (R$^6$)$_n$ have the meanings given in one line of table A.

Table 69 Compounds of formula (I), wherein A is S(O)$_2$, R$^1$ is hydrogen, R$^2$ is CH$_3$, R$^3$ is hydrogen, R$^4$ is benzyl and wherein B, R$^{5.1}$, R$^{5.2}$ and (R$^6$)$_n$ have the meanings given in one line of table A.

Table 70 Compounds of formula (I), wherein A is NH, R$^1$ is hydrogen, R$^2$ is CH$_3$, R$^3$ is hydrogen, R$^4$ is benzyl and wherein B, R$^{5.1}$, R$^{5.2}$ and (R$^6$)$_n$ have the meanings given in one line of table A.

Table 71 Compounds of formula (I), wherein A is NCH$_3$, R$^1$ is hydrogen, R$^2$ is CH$_3$, R$^3$ is hydrogen, R$^4$ is benzyl and wherein B, R$^{5.1}$, R$^{5.2}$ and (R$^6$)$_n$ have the meanings given in one line of table A.

Table 72 Compounds of formula (I), wherein A is CHC$_6$H$_5$, R$^1$ is hydrogen, R$^2$ is CH$_3$, R$^3$ is hydrogen, R$^4$ is benzyl and wherein B, R$^{5.1}$, R$^{5.2}$ and (R$^6$)$_n$ have the meanings given in one line of table A.

Table 73 Compounds of formula (I), wherein A is CH$_2$, R$^1$ is hydrogen, R$^2$ is CH$_3$, R$^3$ is hydrogen, R$^4$ is allyl and wherein B, R$^{5.1}$, R$^{5.2}$ and (R$^6$)$_n$ have the meanings given in one line of table A.

Table 74 Compounds of formula (I), wherein A is O, R$^1$ is hydrogen, R$^2$ is CH$_3$, R$^3$ is hydrogen, R$^4$ is allyl and wherein B, R$^{5.1}$, R$^{5.2}$ and (R$^6$)$_n$ have the meanings given in one line of table A.

Table 75 Compounds of formula (I), wherein A is S, R$^1$ is hydrogen, R$^2$ is CH$_3$, R$^3$ is hydrogen, R$^4$ is allyl and wherein B, R$^{5.1}$, R$^{5.2}$ and (R$^6$)$_n$ have the meanings given in one line of table A.

Table 76 Compounds of formula (I), wherein A is S(O), R$^1$ is hydrogen, R$^2$ is CH$_3$, R$^3$ is hydrogen, R$^4$ is allyl and wherein B, R$^{5.1}$, R$^{5.2}$ and (R$^6$)$_n$ have the meanings given in one line of table A.

Table 77 Compounds of formula (I), wherein A is S(O)$_2$, R$^1$ is hydrogen, R$^2$ is CH$_3$, R$^3$ is hydrogen, R$^4$ is allyl and wherein B, R$^{5.1}$, R$^{5.2}$ and (R$^6$)$_n$ have the meanings given in one line of table A.

Table 78 Compounds of formula (I), wherein A is NH, R$^1$ is hydrogen, R$^2$ is CH$_3$, R$^3$ is hydrogen, R$^4$ is allyl and wherein B, R$^{5.1}$, R$^{5.2}$ and (R$^6$)$_n$ have the meanings given in one line of table A.

Table 79 Compounds of formula (I), wherein A is NCH$_3$, R$^1$ is hydrogen, R$^2$ is CH$_3$, R$^3$ is hydrogen, R$^4$ is allyl and wherein B, R$^{5.1}$, R$^{5.2}$ and (R$^6$)$_n$ have the meanings given in one line of table A.

Table 80 Compounds of formula (I), wherein A is CHC$_6$H$_5$, R$^1$ is hydrogen, R$^2$ is CH$_3$, R$^3$ is hydrogen, R$^4$ is allyl and wherein B, R$^{5.1}$, R$^{5.2}$ and (R$^6$)$_n$ have the meanings given in one line of table A.

Table 81 Compounds of formula (I), wherein A is CH$_2$, R$^1$ is hydrogen, R$^2$ is COCH$_3$, R$^3$ is hydrogen, R$^4$ is hydrogen and wherein B, R$^{5.1}$, R$^{5.2}$ and (R$^6$)$_n$ have the meanings given in any of lines 145 to 1296 of table A.

Table 82 Compounds of formula (I), wherein A is O, R$^1$ is hydrogen, R$^2$ is COCH$_3$, R$^3$ is hydrogen, R$^4$ is hydrogen and wherein B, R$^{5.1}$, R$^{5.2}$ and (R$^6$)$_n$ have the meanings given in one line of table A.

Table 83 Compounds of formula (I), wherein A is S, R$^1$ is hydrogen, R$^2$ is COCH$_3$, R$^3$ is hydrogen, R$^4$ is hydrogen and wherein B, R$^{5.1}$, R$^{5.2}$ and (R$^6$)$_n$ have the meanings given in one line of table A.

Table 84 Compounds of formula (I), wherein A is S(O), R$^1$ is hydrogen, R$^2$ is COCH$_3$, R$^3$ is hydrogen, R$^4$ is hydrogen and wherein B, R$^{5.1}$, R$^{5.2}$ and (R$^6$)$_n$ have the meanings given in one line of table A.

Table 85 Compounds of formula (I), wherein A is S(O)$_2$, R$^1$ is hydrogen, R$^2$ is COCH$_3$, R$^3$ is hydrogen, R$^4$ is hydrogen and wherein B, R$^{5.1}$, R$^{5.2}$ and (R$^6$)$_n$ have the meanings given in one line of table A.

Table 86 Compounds of formula (I), wherein A is NH, R$^1$ is hydrogen, R$^2$ is COCH$_3$, R$^3$ is hydrogen, R$^4$ is hydrogen and wherein B, R$^{5.1}$, R$^{5.2}$ and (R$^6$)$_n$ have the meanings given in one line of table A.

Table 87 Compounds of formula (I), wherein A is NCH$_3$, R$^1$ is hydrogen, R$^2$ is COCH$_3$, R$^3$ is hydrogen, R$^4$ is hydrogen and wherein B, R$^{5.1}$, R$^{5.2}$ and (R$^6$)$_n$ have the meanings given in one line of table A.

Table 88 Compounds of formula (I), wherein A is CHC$_6$H$_5$, R$^1$ is hydrogen, R$^2$ is COCH$_3$, R$^3$ is hydrogen, R$^4$ is hydrogen and wherein B, R$^{5.1}$, R$^{5.2}$ and (R$^6$)$_n$ have the meanings given in one line of table A.

Table 89 Compounds of formula (I), wherein A is CH$_2$, R$^1$ is hydrogen, R$^2$ is COCH$_3$, R$^3$ is hydrogen, R$^4$ is CH$_3$ and wherein B, R$^{5.1}$, R$^{5.2}$ and (R$^6$)$_n$ have the meanings given in one line of table A.

Table 90 Compounds of formula (I), wherein A is O, R$^1$ is hydrogen, R$^2$ is COCH$_3$, R$^3$ is hydrogen, R$^4$ is CH$_3$ and wherein B, R$^{5.1}$, R$^{5.2}$ and (R$^6$)$_n$ have the meanings given in one line of table A.

Table 91 Compounds of formula (I), wherein A is S, R$^1$ is hydrogen, R$^2$ is COCH$_3$, R$^3$ is hydrogen, R$^4$ is CH$_3$ and wherein B, R$^{5.1}$, R$^{5.2}$ and (R$^6$)$_n$ have the meanings given in one line of table A.

Table 92 Compounds of formula (I), wherein A is S(O), R$^1$ is hydrogen, R$^2$ is COCH$_3$, R$^3$ is hydrogen, R$^4$ is CH$_3$ and wherein B, R$^{5.1}$, R$^{5.2}$ and (R$^6$)$_n$ have the meanings given in one line of table A.

Table 93 Compounds of formula (I), wherein A is S(O)$_2$, R$^1$ is hydrogen, R$^2$ is COCH$_3$, R$^3$ is hydrogen, R$^4$ is CH$_3$ and wherein B, R$^{5.1}$, R$^{5.2}$ and (R$^6$)$_n$ have the meanings given in one line of table A.

Table 94 Compounds of formula (I), wherein A is NH, R$^1$ is hydrogen, R$^2$ is COCH$_3$, R$^3$ is hydrogen, R$^4$ is CH$_3$ and wherein B, R$^{5.1}$, R$^{5.2}$ and (R$^6$)$_n$ have the meanings given in one line of table A.

Table 95 Compounds of formula (I), wherein A is NCH$_3$, R$^1$ is hydrogen, R$^2$ is COCH$_3$, R$^3$ is hydrogen, R$^4$ is CH$_3$ and wherein B, R$^{5.1}$, R$^{5.2}$ and (R$^6$)$_n$ have the meanings given in one line of table A.

Table 96 Compounds of formula (I), wherein A is CHC$_6$H$_5$, R$^1$ is hydrogen, R$^2$ is COCH$_3$, R$^3$ is hydrogen, R$^4$ is CH$_3$ and wherein B, R$^{5.1}$, R$^{5.2}$ and (R$^6$)$_n$ have the meanings given in one line of table A.

Table 97 Compounds of formula (I), wherein A is CH$_2$, R$^1$ is hydrogen, R$^2$ is COCH$_3$, R$^3$ is hydrogen, R$^4$ is phenyl and wherein B, R$^{5.1}$, R$^{5.2}$ and (R$^6$)$_n$ have the meanings given in one line of table A.

Table 98 Compounds of formula (I), wherein A is O, R$^1$ is hydrogen, R$^2$ is COCH$_3$, R$^3$ is hydrogen, R$^4$ is phenyl and wherein B, R$^{5.1}$, R$^{5.2}$ and (R$^6$)$_n$ have the meanings given in one line of table A.

Table 99 Compounds of formula (I), wherein A is S, R$^1$ is hydrogen, R$^2$ is COCH$_3$, R$^3$ is hydrogen, R$^4$ is phenyl and wherein B, R$^{5.1}$, R$^{5.2}$ and (R$^6$)$_n$ have the meanings given in one line of table A.

Table 100 Compounds of formula (I), wherein A is S, R$^1$ is hydrogen, R$^2$ is COCH$_3$, R$^3$ is hydrogen, R$^4$ is phenyl and wherein B, R$^{5.1}$, R$^{5.2}$ and (R$^6$)$_n$ have the meanings given in one line of table A.

Table 101 Compounds of formula (I), wherein A is S, R$^1$ is hydrogen, R$^2$ is COCH$_3$, R$^3$ is hydrogen, R$^4$ is phenyl and wherein B, R$^{5.1}$, R$^{5.2}$ and (R$^6$)$_n$ have the meanings given in one line of table A.

Table 102 Compounds of formula (I), wherein A is S, R$^1$ is hydrogen, R$^2$ is COCH$_3$, R$^3$ is hydrogen, R$^4$ is phenyl and wherein B, R$^{5.1}$, R$^{5.2}$ and (R$^6$)$_n$ have the meanings given in one line of table A.

Table 103 Compounds of formula (I), wherein A is S, R$^1$ is hydrogen, R$^2$ is COCH$_3$, R$^3$ is hydrogen, R$^4$ is phenyl and wherein B, R$^{5.1}$, R$^{5.2}$ and (R$^6$)$_n$ have the meanings given in one line of table A.

Table 104 Compounds of formula (I), wherein A is S, R$^1$ is hydrogen, R$^2$ is COCH$_3$, R$^3$ is hydrogen, R$^4$ is phenyl and wherein B, R$^{5.1}$, R$^{5.2}$ and (R$^6$)$_n$ have the meanings given in one line of table A.

Table 105 Compounds of formula (I), wherein A is CH$_2$, R$^1$ is hydrogen, R$^2$ is COCH$_3$, R$^3$ is hydrogen, R$^4$ is benzyl and wherein B, R$^{5.1}$, R$^{5.2}$ and (R$^6$)$_n$ have the meanings given in one line of table A.

Table 106 Compounds of formula (I), wherein A is O, R$^1$ is hydrogen, R$^2$ is COCH$_3$, R$^3$ is hydrogen, R$^4$ is benzyl and wherein B, R$^{5.1}$, R$^{5.2}$ and (R$^6$)$_n$ have the meanings given in one line of table A.

Table 107 Compounds of formula (I), wherein A is S, R$^1$ is hydrogen, R$^2$ is COCH$_3$, R$^3$ is hydrogen, R$^4$ is benzyl and wherein B, R$^{5.1}$, R$^{5.2}$ and (R$^6$)$_n$ have the meanings given in one line of table A.

Table 108 Compounds of formula (I), wherein A is S(O), R$^1$ is hydrogen, R$^2$ is COCH$_3$, R$^3$ is hydrogen, R$^4$ is benzyl and wherein B, R$^{5.1}$, R$^{5.2}$ and (R$^6$)$_n$ have the meanings given in one line of table A.

Table 109 Compounds of formula (I), wherein A is S(O)$_2$, R$^1$ is hydrogen, R$^2$ is COCH$_3$, R$^3$ is hydrogen, R$^4$ is benzyl and wherein B, R$^{5.1}$, R$^{5.2}$ and (R$^6$)$_n$ have the meanings given in one line of table A.

Table 110 Compounds of formula (I), wherein A is NH, R$^1$ is hydrogen, R$^2$ is COCH$_3$, R$^3$ is hydrogen, R$^4$ is benzyl and wherein B, R$^{5.1}$, R$^{5.2}$ and (R$^6$)$_n$ have the meanings given in one line of table A.

Table 111 Compounds of formula (I), wherein A is NCH$_3$, R$^1$ is hydrogen, R$^2$ is COCH$_3$, R$^3$ is hydrogen, R$^4$ is benzyl and wherein B, R$^{5.1}$, R$^{5.2}$ and (R$^6$)$_n$ have the meanings given in one line of table A.

Table 112 Compounds of formula (I), wherein A is CHC$_6$H$_5$, R$^1$ is hydrogen, R$^2$ is COCH$_3$, R$^3$ is hydrogen, R$^4$ is benzyl and wherein B, R$^{5.1}$, R$^{5.2}$ and (R$^6$)$_n$ have the meanings given in one line of table A.

Table 113 Compounds of formula (I), wherein A is CH$_2$, R$^1$ is hydrogen, R$^2$ is COCH$_3$, R$^3$ is hydrogen, R$^4$ is allyl and wherein B, R$^{5.1}$, R$^{5.2}$ and (R$^6$)$_n$ have the meanings given in one line of table A.

Table 114 Compounds of formula (I), wherein A is O, R$^1$ is hydrogen, R$^2$ is COCH$_3$, R$^3$ is hydrogen, R$^4$ is allyl and wherein B, R$^{5.1}$, R$^{5.2}$ and (R$^6$)$_n$ have the meanings given in one line of table A.

Table 115 Compounds of formula (I), wherein A is S, R$^1$ is hydrogen, R$^2$ is COCH$_3$, R$^3$ is hydrogen, R$^4$ is allyl and wherein B, R$^{5.1}$, R$^{5.2}$ and (R$^6$)$_n$ have the meanings given in one line of table A.

Table 116 Compounds of formula (I), wherein A is S(O), R$^1$ is hydrogen, R$^2$ is COCH$_3$, R$^3$ is hydrogen, R$^4$ is allyl and wherein B, R$^{5.1}$, R$^{5.2}$ and (R$^6$)$_n$ have the meanings given in one line of table A.

Table 117 Compounds of formula (I), wherein A is S(O)$_2$, R$^1$ is hydrogen, R$^2$ is COCH$_3$, R$^3$ is hydrogen, R$^4$ is allyl and wherein B, R$^{5.1}$, R$^{5.2}$ and (R$^6$)$_n$ have the meanings given in one line of table A.

Table 118 Compounds of formula (I), wherein A is NH, R$^1$ is hydrogen, R$^2$ is COCH$_3$, R$^3$ is hydrogen, R$^4$ is allyl and wherein B, R$^{5.1}$, R$^{5.2}$ and (R$^6$)$_n$ have the meanings given in one line of table A.

Table 119 Compounds of formula (I), wherein A is NCH$_3$, R$^1$ is hydrogen, R$^2$ is COCH$_3$, R$^3$ is hydrogen, R$^4$ is allyl and wherein B, R$^{5.1}$, R$^{5.2}$ and (R$^6$)$_n$ have the meanings given in one line of table A.

Table 120 Compounds of formula (I), wherein A is $CHC_6H_5$, $R^1$ is hydrogen, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 121 Compounds of formula (I), wherein A is $CH_2$, $R^1$ is hydrogen, $R^3$ is $CH_3$, $R^2$ is hydrogen, $R^4$ is hydrogen and wherein B, $R^{5.1}$, $R^{5.2}$ and $(R^6)_n$ have the meanings given in any of lines 145 to 1296 of table A.

Table 122 Compounds of formula (I), wherein A is O, $R^1$ is hydrogen, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 123 Compounds of formula (I), wherein A is S, $R^1$ is hydrogen, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 124 Compounds of formula (I), wherein A is S(O), $R^1$ is hydrogen, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 125 Compounds of formula (I), wherein A is $S(O)_2$, $R^1$ is hydrogen, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 126 Compounds of formula (I), wherein A is NH, $R^1$ is hydrogen, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 127 Compounds of formula (I), wherein A is $NCH_3$, $R^1$ is hydrogen, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 128 Compounds of formula (I), wherein A is $CHC_6H_5$, $R^1$ is hydrogen, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 129 Compounds of formula (I), wherein A is $CH_2$, $R^1$ is hydrogen, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 130 Compounds of formula (I), wherein A is O, $R^1$ is hydrogen, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 131 Compounds of formula (I), wherein A is S, $R^1$ is hydrogen, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 132 Compounds of formula (I), wherein A is S(O) $R^1$ is hydrogen, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 133 Compounds of formula (I), wherein A is $S(O)_2$, $R^1$ is hydrogen, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 134 Compounds of formula (I), wherein A is NH, $R^1$ is hydrogen, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 135 Compounds of formula (I), wherein A is $NCH_3$, $R^1$ is hydrogen, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 136 Compounds of formula (I), wherein A is $CHC_6H_5$, $R^1$ is hydrogen, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 137 Compounds of formula (I), wherein A is $CH_2$, $R^1$ is hydrogen, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 138 Compounds of formula (I), wherein A is O, $R^1$ is hydrogen, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 139 Compounds of formula (I), wherein A is S, $R^1$ is hydrogen, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 140 Compounds of formula (I), wherein A is S(O), $R^1$ is hydrogen, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 141 Compounds of formula (I), wherein A is $S(O)_2$, $R^1$ is hydrogen, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 142 Compounds of formula (I), wherein A is NH, $R^1$ is hydrogen, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 143 Compounds of formula (I), wherein A is $NCH_3$, $R^1$ is hydrogen, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 144 Compounds of formula (I), wherein A is $CHC_6H_5$, $R^1$ is hydrogen, $R^3$ is $CH_3$, $R^2$ is hydrogen, $R^4$ is phenyl and wherein B, $R^{5.1}$, $R^5$ and $(R^6)_n$ have the meanings given in one line of table A.

Table 145 Compounds of formula (I), wherein A is $CH_2$, $R^1$ is hydrogen, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 146 Compounds of formula (I), wherein A is O, $R^1$ is hydrogen, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 147 Compounds of formula (I), wherein A is S, $R^1$ is hydrogen, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 148 Compounds of formula (I), wherein A is S(O), $R^1$ is hydrogen, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 149 Compounds of formula (I), wherein A is $S(O)_2$, $R^1$ is hydrogen, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 150 Compounds of formula (I), wherein A is NH, $R^1$ is hydrogen, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 151 Compounds of formula (I), wherein A is $NCH_3$, $R^1$ is hydrogen, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 152 Compounds of formula (I), wherein A is $CHC_6H_5$, $R^1$ is hydrogen, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 153 Compounds of formula (I), wherein A is $CH_2$, $R^1$ is hydrogen, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 154 Compounds of formula (I), wherein A is O, $R^1$ is hydrogen, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 155 Compounds of formula (I), wherein A is S, $R^1$ is hydrogen, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 156 Compounds of formula (I), wherein A is S(O), $R^1$ is hydrogen, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 157 Compounds of formula (I), wherein A is $S(O)_2$, $R^1$ is hydrogen, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 158 Compounds of formula (I), wherein A is NH, $R^1$ is hydrogen, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 159 Compounds of formula (I), wherein A is $NCH_3$, $R^1$ is hydrogen, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 160 Compounds of formula (I), wherein A is $CHC_6H_5$, $R^1$ is hydrogen, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 161 Compounds of formula (I), wherein A is $CH_2$, $R^1$ is hydrogen, $R^3$ is $CH_3$, $R^2$ is $CH_3$, $R^4$ is hydrogen and wherein B, $R^{5.1}$, $R^{5.2}$ and $(R^6)_n$ have the meanings given in any of lines 145 to 1296 of table A.

Table 162 Compounds of formula (I), wherein A is O, $R^1$ is hydrogen, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 163 Compounds of formula (I), wherein A is S, $R^1$ is hydrogen, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 164 Compounds of formula (I), wherein A is S(O), $R^1$ is hydrogen, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 165 Compounds of formula (I), wherein A is $S(O)_2$, $R^1$ is hydrogen, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 166 Compounds of formula (I), wherein A is NH, $R^1$ is hydrogen, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 167 Compounds of formula (I), wherein A is $NCH_3$, $R^1$ is hydrogen, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 168 Compounds of formula (I), wherein A is $CHC_6H_5$, $R^1$ is hydrogen, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 169 Compounds of formula (I), wherein A is $CH_2$, $R^1$ is hydrogen, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 170 Compounds of formula (I), wherein A is O, $R^1$ is hydrogen, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 171 Compounds of formula (I), wherein A is S, $R^1$ is hydrogen, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 172 Compounds of formula (I), wherein A is S(O), $R^1$ is hydrogen, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 173 Compounds of formula (I), wherein A is $S(O)_2$, $R^1$ is hydrogen, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 174 Compounds of formula (I), wherein A is NH, $R^1$ is hydrogen, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 175 Compounds of formula (I), wherein A is $NCH_3$, $R^1$ is hydrogen, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 176 Compounds of formula (I), wherein A is $CHC_6H_5$, $R^1$ is hydrogen, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 177 Compounds of formula (I), wherein A is $CH_2$, $R^1$ is hydrogen, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 178 Compounds of formula (I), wherein A is O, $R^1$ is hydrogen, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 179 Compounds of formula (I), wherein A is S, $R^1$ is hydrogen, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 180 Compounds of formula (I), wherein A is S(O), $R^1$ is hydrogen, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 181 Compounds of formula (I), wherein A is $S(O)_2$, $R^1$ is hydrogen, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 182 Compounds of formula (I), wherein A is NH, $R^1$ is hydrogen, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 183 Compounds of formula (I), wherein A is $NCH_3$, $R^1$ is hydrogen, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 184 Compounds of formula (I), wherein A is $CHC_6H_5$, $R^1$ is hydrogen, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 185 Compounds of formula (I), wherein A is $CH_2$, $R^1$ is hydrogen, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 186 Compounds of formula (I), wherein A is O, $R^1$ is hydrogen, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 187 Compounds of formula (I), wherein A is S, $R^1$ is hydrogen, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 188 Compounds of formula (I), wherein A is S(O), $R^1$ is hydrogen, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 189 Compounds of formula (I), wherein A is $S(O)_2$, $R^1$ is hydrogen, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 190 Compounds of formula (I), wherein A is NH, $R^1$ is hydrogen, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 191 Compounds of formula (I), wherein A is $NCH_3$, $R^1$ is hydrogen, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 192 Compounds of formula (I), wherein A is $CHC_6H_5$, $R^1$ is hydrogen, $R^3$ is $CH_3$, $R^2$ is $CH_3$, $R^4$ is benzyl and wherein B, $R^{5.1}$, $R^5$ and $(R^6)_n$ have the meanings given in one line of table A.

Table 193 Compounds of formula (I), wherein A is $CH_2$, $R^1$ is hydrogen, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 194 Compounds of formula (I), wherein A is O, $R^1$ is hydrogen, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 195 Compounds of formula (I), wherein A is S, $R^1$ is hydrogen, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 196 Compounds of formula (I), wherein A is S(O), $R^1$ is hydrogen, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 197 Compounds of formula (I), wherein A is $S(O)_2$, $R^1$ is hydrogen, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 198 Compounds of formula (I), wherein A is NH, $R^1$ is hydrogen, $R^3$ is $CH_3$, $R^2$ is $CH_3$, $R^4$ is allyl and wherein B, $R^{5.1}$, $R^5$ and $(R^6)_n$ have the meanings given in one line of table A.

Table 199 Compounds of formula (I), wherein A is $NCH_3$, $R^1$ is hydrogen, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 200 Compounds of formula (I), wherein A is $CHC_6H_5$, $R^1$ is hydrogen, $R^3$ is $CH_3$, $R^2$ is $CH_3$, $R^4$ is allyl and wherein B, $R^{5.1}$, $R^5$ and $(R^6)_n$ have the meanings given in one line of table A.

Table 201 Compounds of formula (I), wherein A is $CH_2$, $R^1$ is hydrogen, $R^3$ is $CH_3$, $R^2$ is $COCH_3$, $R^4$ is hydrogen and wherein B, $R^{5.1}$, $R^{5.2}$ and $(R^6)_n$ have the meanings given in any of lines 145 to 1296 of table A.

Table 202 Compounds of formula (I), wherein A is O, $R^1$ is hydrogen, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 203 Compounds of formula (I), wherein A is S, $R^1$ is hydrogen, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 204 Compounds of formula (I), wherein A is S(O), $R^1$ is hydrogen, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 205 Compounds of formula (I), wherein A is $S(O)_2$, $R^1$ is hydrogen, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 206 Compounds of formula (I), wherein A is NH, $R^1$ is hydrogen, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 207 Compounds of formula (I), wherein A is $NCH_3$, $R^1$ is hydrogen, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 208 Compounds of formula (I), wherein A is $CHC_6H_5$, $R^1$ is hydrogen, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 209 Compounds of formula (I), wherein A is $CH_2$, $R^1$ is hydrogen, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 210 Compounds of formula (I), wherein A is O, $R^1$ is hydrogen, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 211 Compounds of formula (I), wherein A is S, $R^1$ is hydrogen, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 212 Compounds of formula (I), wherein A is S(O), $R^1$ is hydrogen, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 213 Compounds of formula (I), wherein A is $S(O)_2$, $R^1$ is hydrogen, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 214 Compounds of formula (I), wherein A is NH, $R^1$ is hydrogen, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 215 Compounds of formula (I), wherein A is $NCH_3$, $R^1$ is hydrogen, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 216 Compounds of formula (I), wherein A is $CHC_6H_5$, $R^1$ is hydrogen, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 217 Compounds of formula (I), wherein A is $CH_2$, $R^1$ is hydrogen, $R^3$ is $CH_3$, $R^2$ is $COCH_3$, $R^4$ is phenyl and wherein B, $R^{5.1}$, $R^{5.2}$ and $(R^6)_n$ have the meanings given in of one line of table A.

Table 218 Compounds of formula (I), wherein A is O, $R^1$ is hydrogen, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 219 Compounds of formula (I), wherein A is S, $R^1$ is hydrogen, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 220 Compounds of formula (I), wherein A is S(O), $R^1$ is hydrogen, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 221 Compounds of formula (I), wherein A is $S(O)_2$, $R^1$ is hydrogen, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 222 Compounds of formula (I), wherein A is NH, $R^1$ is hydrogen, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 223 Compounds of formula (I), wherein A is $NCH_3$, $R^1$ is hydrogen, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 224 Compounds of formula (I), wherein A is $CHC_6H_5$, $R^1$ is hydrogen, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 225 Compounds of formula (I), wherein A is $CH_2$, $R^1$ is hydrogen, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 226 Compounds of formula (I), wherein A is O, $R^1$ is hydrogen, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 227 Compounds of formula (I), wherein A is S, $R^1$ is hydrogen, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 228 Compounds of formula (I), wherein A is S(O), $R^1$ is hydrogen, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 229 Compounds of formula (I), wherein A is $S(O)_2$, $R^1$ is hydrogen, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 230 Compounds of formula (I), wherein A is NH, $R^1$ is hydrogen, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 231 Compounds of formula (I), wherein A is $NCH_3$, $R^1$ is hydrogen, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 232 Compounds of formula (I), wherein A is $CHC_6H_5$, $R^1$ is hydrogen, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 233 Compounds of formula (I), wherein A is $CH_2$, $R^1$ is hydrogen, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 234 Compounds of formula (I), wherein A is O, $R^1$ is hydrogen, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 235 Compounds of formula (I), wherein A is S, $R^1$ is hydrogen, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 236 Compounds of formula (I), wherein A is S(O), $R^1$ is hydrogen, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 237 Compounds of formula (I), wherein A is $S(O)_2$, $R^1$ is hydrogen, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 238 Compounds of formula (I), wherein A is NH, $R^1$ is hydrogen, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 239 Compounds of formula (I), wherein A is $NCH_3$, $R^1$ is hydrogen, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 240 Compounds of formula (I), wherein A is $CHC_6H_5$, $R^1$ is hydrogen, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 241 Compounds of formula (I), wherein A is $CH_2$, $R^1$ is hydrogen, $R^3$ is $COCH_3$, $R^2$ is hydrogen, $R^4$ is hydrogen and wherein B, $R^{5.1}$, $R^{5.2}$ and $(R^6)_n$ have the meanings given in any of lines 145 to 1296 of table A.

Table 242 Compounds of formula (I), wherein A is O, $R^1$ is hydrogen, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 243 Compounds of formula (I), wherein A is S, $R^1$ is hydrogen, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 244 Compounds of formula (I), wherein A is S(O), $R^1$ is hydrogen, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 245 Compounds of formula (I), wherein A is $S(O)_2$, $R^1$ is hydrogen, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 246 Compounds of formula (I), wherein A is NH, $R^1$ is hydrogen, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 247 Compounds of formula (I), wherein A is $NCH_3$, $R^1$ is hydrogen, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 248 Compounds of formula (I), wherein A is $CHC_6H_5$, $R^1$ is hydrogen, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 249 Compounds of formula (I), wherein A is $CH_2$, $R^1$ is hydrogen, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 250 Compounds of formula (I), wherein A is O, $R^1$ is hydrogen, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 25.1 Compounds of formula (I), wherein A is S, $R^1$ is hydrogen, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 252 Compounds of formula (I), wherein A is S(O), $R^1$ is hydrogen, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 253 Compounds of formula (I), wherein A is $S(O)_2$, $R^1$ is hydrogen, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 254 Compounds of formula (I), wherein A is NH, $R^1$ is hydrogen, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 255 Compounds of formula (I), wherein A is $NCH_3$, $R^1$ is hydrogen, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 256 Compounds of formula (I), wherein A is $CHC_6H_5$, $R^1$ is hydrogen, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 257 Compounds of formula (I), wherein A is $CH_2$, $R^1$ is hydrogen, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 258 Compounds of formula (I), wherein A is O, $R^1$ is hydrogen, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 259 Compounds of formula (I), wherein A is S, $R^1$ is hydrogen, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 260 Compounds of formula (I), wherein A is S(O), $R^1$ is hydrogen, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 261 Compounds of formula (I), wherein A is $S(O)_2$, $R^1$ is hydrogen, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 262 Compounds of formula (I), wherein A is NH, $R^1$ is hydrogen, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 263 Compounds of formula (I), wherein A is $NCH_3$, $R^1$ is hydrogen, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 264 Compounds of formula (I), wherein A is $CHC_6H_5$, $R^1$ is hydrogen, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 265 Compounds of formula (I), wherein A is $CH_2$, $R^1$ is hydrogen, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 266 Compounds of formula (I), wherein A is O, $R^1$ is hydrogen, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 267 Compounds of formula (I), wherein A is S, $R^1$ is hydrogen, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 268 Compounds of formula (I), wherein A is S(O), $R^1$ is hydrogen, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 269 Compounds of formula (I), wherein A is $S(O)_2$, $R^1$ is hydrogen, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 270 Compounds of formula (I), wherein A is NH, $R^1$ is hydrogen, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 271 Compounds of formula (I), wherein A is $NCH_3$, $R^1$ is hydrogen, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 272 Compounds of formula (I), wherein A is $CHC_6H_5$, $R^1$ is hydrogen, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 273 Compounds of formula (I), wherein A is $CH_2$, $R^1$ is hydrogen, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 274 Compounds of formula (I), wherein A is O, $R^1$ is hydrogen, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 275 Compounds of formula (I), wherein A is S, $R^1$ is hydrogen, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 276 Compounds of formula (I), wherein A is S(O), $R^1$ is hydrogen, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 277 Compounds of formula (I), wherein A is $S(O)_2$, $R^1$ is hydrogen, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 278 Compounds of formula (I), wherein A is NH, $R^1$ is hydrogen, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 279 Compounds of formula (I), wherein A is $NCH_3$, $R^1$ is hydrogen, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 280 Compounds of formula (I), wherein A is $CHC_6H_5$, $R^1$ is hydrogen, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 281 Compounds of formula (I), wherein A is $CH_2$, $R^1$ is hydrogen, $R^3$ is $COCH_3$, $R^2$ is $CH_3$, $R^4$ is hydrogen and wherein B, $R^{5.1}$, $R^{5.2}$ and $(R^6)_n$ have the meanings given in any of lines 145 to 1296 of table A.

Table 282 Compounds of formula (I), wherein A is O, $R^1$ is hydrogen, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 283 Compounds of formula (I), wherein A is S, $R^1$ is hydrogen, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 284 Compounds of formula (I), wherein A is S(O), $R^1$ is hydrogen, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 285 Compounds of formula (I), wherein A is $S(O)_2$, $R^1$ is hydrogen, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 286 Compounds of formula (I), wherein A is NH, $R^1$ is hydrogen, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 287 Compounds of formula (I), wherein A is $NCH_3$, $R^1$ is hydrogen, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 288 Compounds of formula (I), wherein A is $CHC_6H_5$, $R^1$ is hydrogen, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 289 Compounds of formula (I), wherein A is $CH_2$, $R^1$ is hydrogen, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 290 Compounds of formula (I), wherein A is O, $R^1$ is hydrogen, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 291 Compounds of formula (I), wherein A is S, $R^1$ is hydrogen, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 292 Compounds of formula (I), wherein A is S(O), $R^1$ is hydrogen, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 293 Compounds of formula (I), wherein A is $S(O)_2$, $R^1$ is hydrogen, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 294 Compounds of formula (I), wherein A is NH, $R^1$ is hydrogen, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 295 Compounds of formula (I), wherein A is $NCH_3$, $R^1$ is hydrogen, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 296 Compounds of formula (I), wherein A is $CHC_6H_5$, $R^1$ is hydrogen, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 297 Compounds of formula (I), wherein A is $CH_2$, $R^1$ is hydrogen, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 298 Compounds of formula (I), wherein A is O, $R^1$ is hydrogen, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 299 Compounds of formula (I), wherein A is S, $R^1$ is hydrogen, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 300 Compounds of formula (I), wherein A is S(O), $R^1$ is hydrogen, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 301 Compounds of formula (I), wherein A is $S(O)_2$, $R^1$ is hydrogen, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 302 Compounds of formula (I), wherein A is NH, $R^1$ is hydrogen, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 303 Compounds of formula (I), wherein A is $NCH_3$, $R^1$ is hydrogen, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 304 Compounds of formula (I), wherein A is $CHC_6H_5$, $R^1$ is hydrogen, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 305 Compounds of formula (I), wherein A is $CH_2$, $R^1$ is hydrogen, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 306 Compounds of formula (I), wherein A is O, $R^1$ is hydrogen, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 307 Compounds of formula (I), wherein A is S, $R^1$ is hydrogen, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 308 Compounds of formula (I), wherein A is S(O), $R^1$ is hydrogen, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 309 Compounds of formula (I), wherein A is $S(O)_2$, $R^1$ is hydrogen, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 310 Compounds of formula (I), wherein A is NH, $R^1$ is hydrogen, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 311 Compounds of formula (I), wherein A is $NCH_3$, $R^1$ is hydrogen, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 312 Compounds of formula (I), wherein A is $CHC_6H_5$, $R^1$ is hydrogen, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 313 Compounds of formula (I), wherein A is $CH_2$, $R^1$ is hydrogen, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 314 Compounds of formula (I), wherein A is O, $R^1$ is hydrogen, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 315 Compounds of formula (I), wherein A is S, $R^1$ is hydrogen, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 316 Compounds of formula (I), wherein A is S(O), $R^1$ is hydrogen, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 317 Compounds of formula (I), wherein A is $S(O)_2$, $R^1$ is hydrogen, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 318 Compounds of formula (I), wherein A is NH, $R^1$ is hydrogen, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 319 Compounds of formula (I), wherein A is $NCH_3$, $R^1$ is hydrogen, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 320 Compounds of formula (I), wherein A is $CHC_6H_5$, $R^1$ is hydrogen, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 321 Compounds of formula (I), wherein A is $CH_2$, $R^1$ is hydrogen, $R^3$ is $COCH_3$, $R^2$ is $COCH_3$, $R^4$ is hydrogen and wherein B, $R^{5.1}$, $R^{5.2}$ and $(R^6)_n$ have the meanings given in any of lines 145 to 1296 of table A.

Table 322 Compounds of formula (I), wherein A is O, $R^1$ is hydrogen, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 323 Compounds of formula (I), wherein A is S, $R^1$ is hydrogen, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 324 Compounds of formula (I), wherein A is S(O), $R^1$ is hydrogen, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 325 Compounds of formula (I), wherein A is $S(O)_2$, $R^1$ is hydrogen, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 326 Compounds of formula (I), wherein A is NH, $R^1$ is hydrogen, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 327 Compounds of formula (I), wherein A is $NCH_3$, $R^1$ is hydrogen, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 328 Compounds of formula (I), wherein A is $CHC_6H_5$, $R^1$ is hydrogen, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 329 Compounds of formula (I), wherein A is $CH_2$, $R^1$ is hydrogen, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 330 Compounds of formula (I), wherein A is O, $R^1$ is hydrogen, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 331 Compounds of formula (I), wherein A is S, $R^1$ is hydrogen, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 332 Compounds of formula (I), wherein A is S(O), $R^1$ is hydrogen, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 333 Compounds of formula (I), wherein A is $S(O)_2$, $R^1$ is hydrogen, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 334 Compounds of formula (I), wherein A is NH, $R^1$ is hydrogen, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 335 Compounds of formula (I), wherein A is $NCH_3$, $R^1$ is hydrogen, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 336 Compounds of formula (I), wherein A is $CHC_6H_5$, $R^1$ is hydrogen, $R^3$ is $COCH_3$ $R^2$ is $COCH_3$ $R^4$ is $CH_3$ and wherein B, $R^{5.1}$, $R^{5.2}$ and $(R^6)_n$ have the meanings given in one line of table A.

Table 337 Compounds of formula (I), wherein A is $CH_2$, $R^1$ is hydrogen, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 338 Compounds of formula (I), wherein A is O, $R^1$ is hydrogen, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 339 Compounds of formula (I), wherein A is S, $R^1$ is hydrogen, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 340 Compounds of formula (I), wherein A is S(O), $R^1$ is hydrogen, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 341 Compounds of formula (I), wherein A is $S(O)_2$, $R^1$ is hydrogen, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 342 Compounds of formula (I), wherein A is NH, $R^1$ is hydrogen, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 343 Compounds of formula (I), wherein A is $NCH_3$, $R^1$ is hydrogen, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 344 Compounds of formula (I), wherein A is $CHC_6H_5$, $R^1$ is hydrogen, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 345 Compounds of formula (I), wherein A is $CH_2$, $R^1$ is hydrogen, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 346 Compounds of formula (I), wherein A is O, $R^1$ is hydrogen, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 347 Compounds of formula (I), wherein A is S, $R^1$ is hydrogen, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 348 Compounds of formula (I), wherein A is S(O), $R^1$ is hydrogen, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 349 Compounds of formula (I), wherein A is $S(O)_2$, $R^1$ is hydrogen, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 350 Compounds of formula (I), wherein A is NH, $R^1$ is hydrogen, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 351 Compounds of formula (I), wherein A is $NCH_3$, $R^1$ is hydrogen, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 352 Compounds of formula (I), wherein A is $CHC_6H_5$, $R^1$ is hydrogen, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 353 Compounds of formula (I), wherein A is $CH_2$, $R^1$ is hydrogen, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 354 Compounds of formula (I), wherein A is O, $R^1$ is hydrogen, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 355 Compounds of formula (I), wherein A is S, $R^1$ is hydrogen, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 356 Compounds of formula (I), wherein A is S(O), $R^1$ is hydrogen, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 357 Compounds of formula (I), wherein A is $S(O)_2$, $R^1$ is hydrogen, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 358 Compounds of formula (I), wherein A is NH, $R^1$ is hydrogen, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 359 Compounds of formula (I), wherein A is $NCH_3$, $R^1$ is hydrogen, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 360 Compounds of formula (I), wherein A is $CHC_6H_5$, $R^1$ is hydrogen, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 361 Compounds of formula (I), wherein A is $CH_2$, $R^1$ is $C(O)CH_3$, $R^2$ is hydrogen, $R^3$ is hydrogen, $R^4$ is hydrogen and wherein B, $(R^6)_n$, $R^{5.1}$ and $R^{5.2}$ have the meanings given in any of lines 145 to 1296 of table A.

Table 362 Compounds of formula (I), wherein A is O, $R^1$ is $C(O)CH_3$, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 363 Compounds of formula (I), wherein A is S, $R^1$ is $C(O)CH_3$, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 364 Compounds of formula (I), wherein A is S(O), $R^1$ is $C(O)CH_3$, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 365 Compounds of formula (I), wherein A is $S(O)_2$, $R^1$ is $C(O)CH_3$, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 366 Compounds of formula (I), wherein A is NH, $R^1$ is $C(O)CH_3$, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 367 Compounds of formula (I), wherein A is $NCH_3$, $R^1$ is $C(O)CH_3$, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 368 Compounds of formula (I), wherein A is $CHC_6H_5$, $R^1$ is $C(O)CH_3$, $R^2$ is hydrogen, $R^3$ is hydrogen, $R^4$ is hydrogen and wherein B, $R^{5.1}$, $R^{5.2}$ and $(R^6)_n$ have the meanings given in one line of table A.

Table 369 Compounds of formula (I), wherein A is $CH_2$, $R^1$ is $C(O)CH_3$, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 370 Compounds of formula (I), wherein A is O, $R^1$ is $C(O)CH_3$, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 371 Compounds of formula (I), wherein A is S, $R^1$ is $C(O)CH_3$, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 372 Compounds of formula (I), wherein A is S(O), $R^1$ is $C(O)CH_3$, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 373 Compounds of formula (I), wherein A is $S(O)_2$, $R^1$ is $C(O)CH_3$, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 374 Compounds of formula (I), wherein A is NH, $R^1$ is $C(O)CH_3$, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 375 Compounds of formula (I), wherein A is $NCH_3$, $R^1$ is $C(O)CH_3$, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 376 Compounds of formula (I), wherein A is $CHC_6H_5$, $R^1$ is $C(O)CH_3$, $R^2$ is hydrogen, $R^3$ is hydrogen, $R^4$ is $CH_3$ and wherein B, $R^{5.1}$, $R^{5.2}$ and $(R^6)_n$ have the meanings given in one line of table A.

Table 377 Compounds of formula (I), wherein A is $CH_2$, $R^1$ is $C(O)CH_3$, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 378 Compounds of formula (I), wherein A is O, $R^1$ is $C(O)CH_3$, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 379 Compounds of formula (I), wherein A is S, $R^1$ is $C(O)CH_3$, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 380 Compounds of formula (I), wherein A is S(O), $R^1$ is $C(O)CH_3$, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 381 Compounds of formula (I), wherein A is $S(O)_2$, $R^1$ is $C(O)CH_3$, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 382 Compounds of formula (I), wherein A is NH, $R^1$ is $C(O)CH_3$, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 383 Compounds of formula (I), wherein A is $NCH_3$, $R^1$ is $C(O)CH_3$, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 384 Compounds of formula (I), wherein A is $CHC_6H_5$, $R^1$ is $C(O)CH_3$, $R^2$ is hydrogen, $R^3$ is hydrogen, $R^4$ is phenyl and wherein B, $R^{5.1}$, $R^{5.2}$ and $(R^6)_n$ have the meanings given in one line of table A.

Table 385 Compounds of formula (I), wherein A is $CH_2$, $R^1$ is $C(O)CH_3$, $R^2$ is hydrogen, $R^3$ is hydrogen, $R^4$ is benzyl and wherein B, $R^{5.1}$, $R^{5.2}$ and $(R^6)_n$ have the meanings given in one line of table A.

Table 386 Compounds of formula (I), wherein A is O, $R^1$ is $C(O)CH_3$, $R^2$ is hydrogen, $R^3$ is hydrogen, $R^4$ is benzyl and wherein B, $R^{5.1}$, $R^{5.2}$ and $(R^6)_n$ have the meanings given in one line of table A.

Table 387 Compounds of formula (I), wherein A is S, $R^1$ is $C(O)CH_3$, $R^2$ is hydrogen, $R^3$ is hydrogen, $R^4$ is benzyl and wherein B, $R^{5.1}$, $R^{5.2}$ and $(R^6)_n$ have the meanings given in one line of table A.

Table 388 Compounds of formula (I), wherein A is S(O), $R^1$ is $C(O)CH_3$, $R^2$ is hydrogen, $R^3$ is hydrogen, $R^4$ is benzyl and wherein B, $R^{5.1}$, $R^{5.2}$ and $(R^6)_n$ have the meanings given in one line of table A.

Table 389 Compounds of formula (I), wherein A is $S(O)_2$, $R^1$ is $C(O)CH_3$, $R^2$ is hydrogen, $R^3$ is hydrogen, $R^4$ is benzyl and wherein B, $R^{5.1}$, $R^{5.2}$ and $(R^6)_n$ have the meanings given in one line of table A.

Table 390 Compounds of formula (I), wherein A is NH, $R^1$ is $C(O)CH_3$, $R^2$ is hydrogen, $R^3$ is hydrogen, $R^4$ is benzyl and wherein B, $R^{5.1}$, $R^{5.2}$ and $(R^6)_n$ have the meanings given in one line of table A.

Table 391 Compounds of formula (I), wherein A is $NCH_3$, $R^1$ is $C(O)CH_3$, $R^2$ is hydrogen, $R^3$ is hydrogen, $R^4$ is benzyl and wherein B, $R^{5.1}$, $R^{5.2}$ and $(R^6)_n$ have the meanings given in one line of table A.

Table 392 Compounds of formula (I), wherein A is $CHC_6H_5$, $R^1$ is $C(O)CH_3$, $R^2$ is hydrogen, $R^3$ is hydrogen, $R^4$ is benzyl and wherein B, $R^{5.1}$, $R^{5.2}$ and $(R^6)_n$ have the meanings given in one line of table A.

Table 393 Compounds of formula (I), wherein A is $CH_2$, $R^1$ is $C(O)CH_3$, $R^2$ is hydrogen, $R^3$ is hydrogen, $R^4$ is allyl and wherein B, $R^{5.1}$, $R^{5.2}$ and $(R^6)_n$ have the meanings given in one line of table A.

Table 394 Compounds of formula (I), wherein A is O, $R^1$ is $C(O)CH_3$, $R^2$ is hydrogen, $R^3$ is hydrogen, $R^4$ is allyl and wherein B, $R^{5.1}$, $R^{5.2}$ and $(R^6)_n$ have the meanings given in one line of table A.

Table 395 Compounds of formula (I), wherein A is S, $R^1$ is $C(O)CH_3$, $R^2$ is hydrogen, $R^3$ is hydrogen, $R^4$ is allyl and wherein B, $R^{5.1}$, $R^{5.2}$ and $(R^6)_n$ have the meanings given in one line of table A.

Table 396 Compounds of formula (I), wherein A is S(O), $R^1$ is $C(O)CH_3$, $R^2$ is hydrogen, $R^3$ is hydrogen, $R^4$ is allyl and wherein B, $R^{5.1}$, $R^{5.2}$ and $(R^6)_n$ have the meanings given in one line of table A.

Table 397 Compounds of formula (I), wherein A is $S(O)_2$, $R^1$ is $C(O)CH_3$, $R^2$ is hydrogen, $R^3$ is hydrogen, $R^4$ is allyl and wherein B, $R^{5.1}$, $R^{5.2}$ and $(R^6)_n$ have the meanings given in one line of table A.

Table 398 Compounds of formula (I), wherein A is NH, $R^1$ is $C(O)CH_3$, $R^2$ is hydrogen, $R^3$ is hydrogen, $R^4$ is allyl and wherein B, $R^{5.1}$, $R^{5.2}$ and $(R^6)_n$ have the meanings given in one line of table A.

Table 399 Compounds of formula (I), wherein A is $NCH_3$, $R^1$ is $C(O)CH_3$, $R^2$ is hydrogen, $R^3$ is hydrogen, $R^4$ is allyl and wherein B, $R^{5.1}$, $R^{5.2}$ and $(R^6)_n$ have the meanings given in one line of table A.

Table 400 Compounds of formula (I), wherein A is $CHC_6H_5$, $R^1$ is $C(O)CH_3$, $R^2$ is hydrogen, $R^3$ is hydrogen, $R^4$ is allyl and wherein B, $R^{5.1}$, $R^{5.2}$ and $(R^6)_n$ have the meanings given in one line of table A.

Table 401 Compounds of formula (I), wherein A is $CH_2$, $R^1$ is $C(O)CH_3$, $R^2$ is $CH^3$, $R^3$ is hydrogen, $R^4$ is hydrogen and wherein B, $R^{5.1}$, $R^{5.2}$ and $(R^6)_n$ have the meanings given in any of lines 145 to 1296 of table A.

Table 402 Compounds of formula (I), wherein A is O, $R^1$ is $C(O)CH_3$, $R^2$ is $CH^3$, $R^3$ is hydrogen, $R^4$ is hydrogen and wherein B, $R^{5.1}$, $R^{5.2}$ and $(R^6)_n$ have the meanings given in one line of table A.

Table 403 Compounds of formula (I), wherein A is S, $R^1$ is $C(O)CH_3$, $R^2$ is $CH^3$, $R^3$ is hydrogen, $R^4$ is hydrogen and wherein B, $R^{5.1}$, $R^{5.2}$ and $(R^6)_n$ have the meanings given in one line of table A.

Table 404 Compounds of formula (I), wherein A is S(O), $R^1$ is $C(O)CH_3$, $R^2$ is $CH^3$, $R^3$ is hydrogen, $R^4$ is hydrogen and wherein B, $R^{5.1}$, $R^{5.2}$ and $(R^6)_n$ have the meanings given in one line of table A.

Table 405 Compounds of formula (I), wherein A is $S(O)_2$, $R^1$ is $C(O)CH_3$, $R^2$ is $CH^3$, $R^3$ is hydrogen, $R^4$ is hydrogen and wherein B, $R^{5.1}$, $R^{5.2}$ and $(R^6)_n$ have the meanings given in one line of table A.

Table 406 Compounds of formula (I), wherein A is NH, $R^1$ is $C(O)CH_3$, $R^2$ is $CH^3$, $R^3$ is hydrogen, $R^4$ is hydrogen and wherein B, $R^{5.1}$, $R^{5.2}$ and $(R^6)_n$ have the meanings given in one line of table A.

Table 407 Compounds of formula (I), wherein A is $NCH_3$, $R^1$ is $C(O)CH_3$, $R^2$ is $CH^3$, $R^3$ is hydrogen, $R^4$ is hydrogen and wherein B, $R^{5.1}$, $R^{5.2}$ and $(R^6)_n$ have the meanings given in one line of table A.

Table 408 Compounds of formula (I), wherein A is $CHC_6H_5$, $R^1$ is $C(O)CH_3$, $R^2$ is $CH^3$, $R^3$ is hydrogen, $R^4$ is hydrogen and wherein B, $R^{5.1}$, $R^{5.2}$ and $(R^6)_n$ have the meanings given in one line of table A.

Table 409 Compounds of formula (I), wherein A is $CH_2$, $R^1$ is $C(O)CH_3$, $R^2$ is $CH_3$, $R^3$ is hydrogen, $R^4$ is $CH_3$ and wherein B, $R^{5.1}$, $R^{5.2}$ and $(R^6)_n$ have the meanings given in one line of table A.

Table 410 Compounds of formula (I), wherein A is O, $R^1$ is $C(O)CH_3$, $R^2$ is $CH_3$, $R^3$ is hydrogen, $R^4$ is $CH_3$ and wherein B, $R^{5.1}$, $R^{5.2}$ and $(R^6)_n$ have the meanings given in one line of table A.

Table 411 Compounds of formula (I), wherein A is S, $R^1$ is $C(O)CH_3$, $R^2$ is $CH_3$, $R^3$ is hydrogen, $R^4$ is $CH_3$ and wherein B, $R^{5.1}$, $R^{5.2}$ and $(R^6)_n$ have the meanings given in one line of table A.

Table 412 Compounds of formula (I), wherein A is S(O), $R^1$ is $C(O)CH_3$, $R^2$ is $CH_3$, $R^3$ is hydrogen, $R^4$ is $CH_3$ and wherein B, $R^{5.1}$, $R^{5.2}$ and $(R^6)_n$ have the meanings given in one line of table A.

Table 413 Compounds of formula (I), wherein A is $S(O)_2$, $R^1$ is $C(O)CH_3$, $R^2$ is $CH_3$, $R^3$ is hydrogen, $R^4$ is $CH_3$ and wherein B, $R^{5.1}$, $R^{5.2}$ and $(R^6)_n$ have the meanings given in one line of table A.

Table 414 Compounds of formula (I), wherein A is NH, $R^1$ is $C(O)CH_3$, $R^2$ is $CH_3$, $R^3$ is hydrogen, $R^4$ is $CH_3$ and wherein B, $R^{5.1}$, $R^{5.2}$ and $(R^6)_n$ have the meanings given in one line of table A.

Table 415 Compounds of formula (I), wherein A is $NCH_3$, $R^1$ is $C(O)CH_3$, $R^2$ is $CH_3$, $R^3$ is hydrogen, $R^4$ is $CH_3$ and wherein B, $R^{5.1}$, $R^{5.2}$ and $(R^6)_n$ have the meanings given in one line of table A.

Table 416 Compounds of formula (I), wherein A is $CHC_6H_5$, $R^1$ is $C(O)CH_3$, $R^2$ is $CH_3$, $R^3$ is hydrogen, $R^4$ is $CH_3$ and wherein B, $R^{5.1}$, $R^{5.2}$ and $(R^6)_n$ have the meanings given in one line of table A.

Table 417 Compounds of formula (I), wherein A is $CH_2$, $R^1$ is $C(O)CH_3$, $R^2$ is $CH_3$, $R^3$ is hydrogen, $R^4$ is phenyl and wherein B, $R^{5.1}$, $R^{5.2}$ and $(R^6)_n$ have the meanings given in one line of table A.

Table 418 Compounds of formula (I), wherein A is O, $R^1$ is $C(O)CH_3$, $R^2$ is $CH_3$, $R^3$ is hydrogen, $R^4$ is phenyl and wherein B, $R^{5.1}$, $R^{5.2}$ and $(R^6)_n$ have the meanings given in one line of table A.

Table 419 Compounds of formula (I), wherein A is S, $R^1$ is $C(O)CH_3$, $R^2$ is $CH_3$, $R^3$ is hydrogen, $R^4$ is phenyl and wherein B, $R^{5.1}$, $R^{5.2}$ and $(R^6)_n$ have the meanings given in one line of table A.

Table 420 Compounds of formula (I), wherein A is S(O), $R^1$ is $C(O)CH_3$, $R^2$ is $CH_3$, $R^3$ is hydrogen, $R^4$ is phenyl and wherein B, $R^{5.1}$, $R^{5.2}$ and $(R^6)_n$ have the meanings given in one line of table A.

Table 421 Compounds of formula (I), wherein A is $S(O)_2$, $R^1$ is $C(O)CH_3$, $R^2$ is $CH_3$, $R^3$ is hydrogen, $R^4$ is phenyl and wherein B, $R^{5.1}$, $R^{5.2}$ and $(R^6)_n$ have the meanings given in one line of table A.

Table 422 Compounds of formula (I), wherein A is NH, $R^1$ is $C(O)CH_3$, $R^2$ is $CH_3$, $R^3$ is hydrogen, $R^4$ is phenyl and wherein B, $R^{5.1}$, $R^{5.2}$ and $(R^6)_n$ have the meanings given in one line of table A.

Table 423 Compounds of formula (I), wherein A is $NCH_3$, $R^1$ is $C(O)CH_3$, $R^2$ is $CH_3$, $R^3$ is hydrogen, $R^4$ is phenyl and wherein B, $R^{5.1}$, $R^{5.2}$ and $(R^6)_n$ have the meanings given in one line of table A.

Table 424 Compounds of formula (I), wherein A is $CHC_6H_5$, $R^1$ is $C(O)CH_3$, $R^2$ is $CH_3$, $R^3$ is hydrogen, $R^4$ is phenyl and wherein B, $R^{5.1}$, $R^{5.2}$ and $(R^6)_n$ have the meanings given in one line of table A.

Table 425 Compounds of formula (I), wherein A is $CH_2$, $R^1$ is $C(O)CH_3$, $R^2$ is $CH_3$, $R^3$ is hydrogen, $R^4$ is benzyl and wherein B, $R^{5.1}$, $R^{5.2}$ and $(R^6)_n$ have the meanings given in one line of table A.

Table 426 Compounds of formula (I), wherein A is O, $R^1$ is $C(O)CH_3$, $R^2$ is $CH_3$, $R^3$ is hydrogen, $R^4$ is benzyl and wherein B, $R^{5.1}$, $R^{5.2}$ and $(R^6)_n$ have the meanings given in one line of table A.

Table 427 Compounds of formula (I), wherein A is S, $R^1$ is $C(O)CH_3$, $R^2$ is $CH_3$, $R^3$ is hydrogen, $R^4$ is benzyl and wherein B, $R^{5.1}$, $R^{5.2}$ and $(R^6)_n$ have the meanings given in one line of table A.

Table 428 Compounds of formula (I), wherein A is S(O), $R^1$ is $C(O)CH_3$, $R^2$ is $CH_3$, $R^3$ is hydrogen, $R^4$ is benzyl and wherein B, $R^{5.1}$, $R^{5.2}$ and $(R^6)_n$ have the meanings given in one line of table A.

Table 429 Compounds of formula (I), wherein A is $S(O)_2$, $R^1$ is $C(O)CH_3$, $R^2$ is $CH_3$, $R^3$ is hydrogen, $R^4$ is benzyl and wherein B, $R^{5.1}$, $R^{5.2}$ and $(R^6)_n$ have the meanings given in one line of table A.

Table 430 Compounds of formula (I), wherein A is NH, $R^1$ is $C(O)CH_3$, $R^2$ is $CH_3$, $R^3$ is hydrogen, $R^4$ is benzyl and wherein B, $R^{5.1}$, $R^{5.2}$ and $(R^6)_n$ have the meanings given in one line of table A.

Table 431 Compounds of formula (I), wherein A is $NCH_3$, $R^1$ is $C(O)CH_3$, $R^2$ is $CH_3$, $R^3$ is hydrogen, $R^4$ is benzyl and wherein B, $R^{5.1}$, $R^{5.2}$ and $(R^6)_n$ have the meanings given in one line of table A.

Table 432 Compounds of formula (I), wherein A is $CHC_6H_5$, $R^1$ is $C(O)CH_3$, $R^2$ is $CH_3$, $R^3$ is hydrogen, $R^4$ is benzyl and wherein B, $R^{5.1}$, $R^{5.2}$ and $(R^6)_n$ have the meanings given in one line of table A.

Table 433 Compounds of formula (I), wherein A is $CH_2$, $R^1$ is $C(O)CH_3$, $R^2$ is $CH_3$, $R^3$ is hydrogen, $R^4$ is allyl and wherein B, $R^{5.1}$, $R^{5.2}$ and $(R^6)_n$ have the meanings given in one line of table A.

Table 434 Compounds of formula (I), wherein A is O, $R^1$ is $C(O)CH_3$, $R^2$ is $CH_3$, $R^3$ is hydrogen, $R^4$ is allyl and wherein B, $R^{5.1}$, $R^{5.2}$ and $(R^6)_n$ have the meanings given in one line of table A.

Table 435 Compounds of formula (I), wherein A is S, $R^1$ is $C(O)CH_3$, $R^2$ is $CH_3$, $R^3$ is hydrogen, $R^4$ is allyl and wherein B, $R^{5.1}$, $R^{5.2}$ and $(R^6)_n$ have the meanings given in one line of table A.

Table 436 Compounds of formula (I), wherein A is S(O), $R^1$ is $C(O)CH_3$, $R^2$ is $CH_3$, $R^3$ is hydrogen, $R^4$ is allyl and wherein B, $R^{5.1}$, $R^{5.2}$ and $(R^6)_n$ have the meanings given in one line of table A.

Table 437 Compounds of formula (I), wherein A is $S(O)_2$, $R^1$ is $C(O)CH_3$, $R^2$ is $CH_3$, $R^3$ is hydrogen, $R^4$ is allyl and wherein B, $R^{5.1}$, $R^{5.2}$ and $(R^6)_n$ have the meanings given in one line of table A.

Table 438 Compounds of formula (I), wherein A is NH, $R^1$ is $C(O)CH_3$, $R^2$ is $CH_3$, $R^3$ is hydrogen, $R^4$ is allyl and wherein B, $R^{5.1}$, $R^{5.2}$ and $(R^6)_n$ have the meanings given in one line of table A.

Table 439 Compounds of formula (I), wherein A is $NCH_3$, $R^1$ is $C(O)CH_3$, $R^2$ is $CH_3$, $R^3$ is hydrogen, $R^4$ is allyl and wherein B, $R^{5.1}$, $R^{5.2}$ and $(R^6)_n$ have the meanings given in one line of table A.

Table 440 Compounds of formula (I), wherein A is $CHC_6H_5$, $R^1$ is $C(O)CH_3$, $R^2$ is $CH_3$, $R^3$ is hydrogen, $R^4$ is allyl and wherein B, $R^{5.1}$, $R^{5.2}$ and $(R^6)_n$ have the meanings given in one line of table A.

Table 441 Compounds of formula (I), wherein A is $CH_2$, $R^1$ is $C(O)CH_3$, $R^2$ is $COCH_3$, $R^3$ is hydrogen, $R^4$ is hydrogen and wherein B, $R^{5.1}$, $R^{5.2}$ and $(R^6)_n$ have the meanings given in any of lines 145 to 1296 of table A.

Table 442 Compounds of formula (I), wherein A is O, $R^1$ is $C(O)CH_3$, $R^2$ is $COCH_3$, $R^3$ is hydrogen, $R^4$ is hydrogen and wherein B, $R^{5.1}$, $R^{5.2}$ and $(R^6)_n$ have the meanings given in one line of table A.

Table 443 Compounds of formula (I), wherein A is S, $R^1$ is $C(O)CH_3$, $R^2$ is $COCH_3$, $R^3$ is hydrogen, $R^4$ is hydrogen and wherein B, $R^{5.1}$, $R^{5.2}$ and $(R^6)_n$ have the meanings given in one line of table A.

Table 444 Compounds of formula (I), wherein A is S(O), $R^1$ is $C(O)CH_3$, $R^2$ is $COCH_3$, $R^3$ is hydrogen, $R^4$ is hydrogen and wherein B, $R^{5.1}$, $R^{5.2}$ and $(R^6)_n$ have the meanings given in one line of table A.

Table 445 Compounds of formula (I), wherein A is $S(O)_2$, $R^1$ is $C(O)CH_3$, $R^2$ is $COCH_3$, $R^3$ is hydrogen, $R^4$ is hydrogen and wherein B, $R^{5.1}$, $R^{5.2}$ and $(R^6)_n$ have the meanings given in one line of table A.

Table 446 Compounds of formula (I), wherein A is NH, $R^1$ is $C(O)CH_3$, $R^2$ is $COCH_3$, $R^3$ is hydrogen, $R^4$ is hydrogen and wherein B, $R^{5.1}$, $R^{5.2}$ and $(R^6)_n$ have the meanings given in one line of table A.

Table 447 Compounds of formula (I), wherein A is $NCH_3$, $R^1$ is $C(O)CH_3$, $R^2$ is $COCH_3$, $R^3$ is hydrogen, $R^4$ is hydrogen and wherein B, $R^{5.1}$, $R^{5.2}$ and $(R^6)_n$ have the meanings given in one line of table A.

Table 448 Compounds of formula (I), wherein A is $CHC_6H_5$, $R^1$ is $C(O)CH_3$, $R^2$ is $COCH_3$, $R^3$ is hydrogen, $R^4$ is hydrogen and wherein B, $R^{5.1}$, $R^{5.2}$ and $(R^6)_n$ have the meanings given in one line of table A.

Table 449 Compounds of formula (I), wherein A is $CH_2$, $R^1$ is $C(O)CH_3$, $R^2$ is $COCH_3$, $R^3$ is hydrogen, $R^4$ is $CH_3$ and wherein B, $R^{5.1}$, $R^{5.2}$ and $(R^6)_n$ have the meanings given in one line of table A.

Table 450 Compounds of formula (I), wherein A is O, $R^1$ is $C(O)CH_3$, $R^2$ is $COCH_3$, $R^3$ is hydrogen, $R^4$ is $CH_3$ and wherein B, $R^{5.1}$, $R^{5.2}$ and $(R^6)_n$ have the meanings given in one line of table A.

Table 451 Compounds of formula (I), wherein A is S, $R^1$ is $C(O)CH_3$, $R^2$ is $COCH_3$, $R^3$ is hydrogen, $R^4$ is $CH_3$ and wherein B, $R^{5.1}$, $R^{5.2}$ and $(R^6)_n$ have the meanings given in one line of table A.

Table 452 Compounds of formula (I), wherein A is S(O), $R^1$ is $C(O)CH_3$, $R^2$ is $COCH_3$, $R^3$ is hydrogen, $R^4$ is $CH_3$ and wherein B, $R^{5.1}$, $R^{5.2}$ and $(R^6)_n$ have the meanings given in one line of table A.

Table 453 Compounds of formula (I), wherein A is $S(O)_2$, $R^1$ is $C(O)CH_3$, $R^2$ is $COCH_3$, $R^3$ is hydrogen, $R^4$ is $CH_3$ and wherein B, $R^{5.1}$, $R^{5.2}$ and $(R^6)_n$ have the meanings given in one line of table A.

Table 454 Compounds of formula (I), wherein A is NH, $R^1$ is $C(O)CH_3$, $R^2$ is $COCH_3$, $R^3$ is hydrogen, $R^4$ is $CH_3$ and wherein B, $R^{5.1}$, $R^{5.2}$ and $(R^6)_n$ have the meanings given in one line of table A.

Table 455 Compounds of formula (I), wherein A is $NCH_3$, $R^1$ is $C(O)CH_3$, $R^2$ is $COCH_3$, $R^3$ is hydrogen, $R^4$ is $CH_3$ and wherein B, $R^{5.1}$, $R^{5.2}$ and $(R^6)_n$ have the meanings given in one line of table A.

Table 456 Compounds of formula (I), wherein A is $CHC_6H_5$, $R^1$ is $C(O)CH_3$, $R^2$ is $COCH_3$, $R^3$ is hydrogen, $R^4$ is $CH_3$ and wherein B, $R^{5.1}$, $R^{5.2}$ and $(R^6)_n$ have the meanings given in one line of table A.

Table 457 Compounds of formula (I), wherein A is $CH_2$, $R^1$ is $C(O)CH_3$, $R^2$ is $COCH_3$, $R^3$ is hydrogen, $R^4$ is phenyl and wherein B, $R^{5.1}$, $R^{5.2}$ and $(R^6)_n$ have the meanings given in one line of table A.

Table 458 Compounds of formula (I), wherein A is O, $R^1$ is $C(O)CH_3$, $R^2$ is $COCH_3$, $R^3$ is hydrogen, $R^4$ is phenyl and wherein B, $R^{5.1}$, $R^{5.2}$ and $(R^6)_n$ have the meanings given in one line of table A.

Table 459 Compounds of formula (I), wherein A is S, $R^1$ is $C(O)CH_3$, $R^2$ is $COCH_3$, $R^3$ is hydrogen, $R^4$ is phenyl and wherein B, $R^{5.1}$, $R^{5.2}$ and $(R^6)_n$ have the meanings given in one line of table A.

Table 460 Compounds of formula (I), wherein A is S, $R^1$ is $C(O)CH_3$, $R^2$ is $COCH_3$, $R^3$ is hydrogen, $R^4$ is phenyl and wherein B, $R^{5.1}$, $R^{5.2}$ and $(R^6)_n$ have the meanings given in one line of table A.

Table 461 Compounds of formula (I), wherein A is S, $R^1$ is $C(O)CH_3$, $R^2$ is $COCH_3$, $R^3$ is hydrogen, $R^4$ is phenyl and wherein B, $R^{5.1}$, $R^{5.2}$ and $(R^6)_n$ have the meanings given in one line of table A.

Table 462 Compounds of formula (I), wherein A is S, $R^1$ is $C(O)CH_3$, $R^2$ is $COCH_3$, $R^3$ is hydrogen, $R^4$ is phenyl and wherein B, $R^{5.1}$, $R^{5.2}$ and $(R^6)_n$ have the meanings given in one line of table A.

Table 463 Compounds of formula (I), wherein A is S, $R^1$ is $C(O)CH_3$, $R^2$ is $COCH_3$, $R^3$ is hydrogen, $R^4$ is phenyl and wherein B, $R^{5.1}$, $R^{5.2}$ and $(R^6)_n$ have the meanings given in one line of table A.

Table 464 Compounds of formula (I), wherein A is S, $R^1$ is $C(O)CH_3$, $R^2$ is $COCH_3$, $R^3$ is hydrogen, $R^4$ is phenyl and wherein B, $R^{5.1}$, $R^{5.2}$ and $(R^6)_n$ have the meanings given in one line of table A.

Table 465 Compounds of formula (I), wherein A is $CH_2$, $R^1$ is $C(O)CH_3$, $R^2$ is $COCH_3$, $R^3$ is hydrogen, $R^4$ is benzyl and wherein B, $R^{5.1}$, $R^{5.2}$ and $(R^6)_n$ have the meanings given in one line of table A.

Table 466 Compounds of formula (I), wherein A is O, $R^1$ is $C(O)CH_3$, $R^2$ is $COCH_3$, $R^3$ is hydrogen, $R^4$ is benzyl and wherein B, $R^{5.1}$, $R^{5.2}$ and $(R^6)_n$ have the meanings given in one line of table A.

Table 467 Compounds of formula (I), wherein A is S, $R^1$ is $C(O)CH_3$, $R^2$ is $COCH_3$, $R^3$ is hydrogen, $R^4$ is benzyl and wherein B, $R^{5.1}$, $R^{5.2}$ and $(R^6)_n$ have the meanings given in one line of table A.

Table 468 Compounds of formula (I), wherein A is S(O), $R^1$ is $C(O)CH_3$, $R^2$ is $COCH_3$, $R^3$ is hydrogen, $R^4$ is benzyl and wherein B, $R^{5.1}$, $R^{5.2}$ and $(R^6)_n$ have the meanings given in one line of table A.

Table 469 Compounds of formula (I), wherein A is $S(O)_2$, $R^1$ is $C(O)CH_3$, $R^2$ is $COCH_3$, $R^3$ is hydrogen, $R^4$ is benzyl and wherein B, $R^{5.1}$, $R^{5.2}$ and $(R^6)_n$ have the meanings given in one line of table A.

Table 470 Compounds of formula (I), wherein A is NH, $R^1$ is $C(O)CH_3$, $R^2$ is $COCH_3$, $R^3$ is hydrogen, $R^4$ is benzyl and wherein B, $R^{5.1}$, $R^{5.2}$ and $(R^6)_n$ have the meanings given in one line of table A.

Table 471 Compounds of formula (I), wherein A is $NCH_3$, $R^1$ is $C(O)CH_3$, $R^2$ is $COCH_3$, $R^3$ is hydrogen, $R^4$ is benzyl and wherein B, $R^{5.1}$, $R^{5.2}$ and $(R^6)_n$ have the meanings given in one line of table A.

Table 472 Compounds of formula (I), wherein A is $CHC_6H_5$, $R^1$ is $C(O)CH_3$, $R^2$ is $COCH_3$, $R^3$ is hydrogen, $R^4$ is benzyl and wherein B, $R^{5.1}$, $R^{5.2}$ and $(R^6)_n$ have the meanings given in one line of table A.

Table 473 Compounds of formula (I), wherein A is $CH_2$, $R^1$ is $C(O)CH_3$, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 474 Compounds of formula (I), wherein A is O, $R^1$ is $C(O)CH_3$, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 475 Compounds of formula (I), wherein A is S, $R^1$ is $C(O)CH_3$, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 476 Compounds of formula (I), wherein A is S(O), $R^1$ is $C(O)CH_3$, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 477 Compounds of formula (I), wherein A is $S(O)_2$, $R^1$ is $C(O)CH_3$, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 478 Compounds of formula (I), wherein A is NH, $R^1$ is $C(O)CH_3$, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 479 Compounds of formula (I), wherein A is $NCH_3$, $R^1$ is $C(O)CH_3$, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 480 Compounds of formula (I), wherein A is $CHC_6H_5$, $R^1$ is $C(O)CH_3$, $R^2$ is $COCH_3$, $R^3$ is hydrogen, $R^4$ is allyl and wherein B, $R^{5.1}$, $R^{5.2}$ and $(R^6)_n$ have the meanings given in one line of table A.

Table 481 Compounds of formula (I), wherein A is $CH_2$, $R^1$ is $C(O)CH_3$, $R^3$ is $CH_3$, $R^2$ is hydrogen, $R^4$ is hydrogen and wherein B, $R^{5.1}$, $R^{5.2}$ and $(R^6)_n$ have the meanings given in any of lines 145 to 1296 of table A.

Table 482 Compounds of formula (I), wherein A is O, $R^1$ is $C(O)CH_3$, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 483 Compounds of formula (I), wherein A is S, $R^1$ is $C(O)CH_3$, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 484 Compounds of formula (I), wherein A is S(O), $R^1$ is $C(O)CH_3$, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 485 Compounds of formula (I), wherein A is $S(O)_2$, $R^1$ is $C(O)CH_3$, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 486 Compounds of formula (I), wherein A is NH, $R^1$ is $C(O)CH_3$, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 487 Compounds of formula (I), wherein A is $NCH_3$, $R^1$ is $C(O)CH_3$, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 488 Compounds of formula (I), wherein A is $CHC_6H_5$, $R^1$ is $C(O)CH_3$, $R^3$ is $CH_3$, $R^2$ is hydrogen, $R^4$ is hydrogen and wherein B, $R^{5.1}$, $R^{5.2}$ and $(R^6)_n$ have the meanings given in one line of table A.

Table 489 Compounds of formula (I), wherein A is $CH_2$, $R^1$ is $C(O)CH_3$, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 490 Compounds of formula (I), wherein A is O, $R^1$ is $C(O)CH_3$, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 491 Compounds of formula (I), wherein A is S, $R^1$ is $C(O)CH_3$, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 492 Compounds of formula (I), wherein A is S(O) $R^1$ is $C(O)CH_3$, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 493 Compounds of formula (I), wherein A is $S(O)_2$, $R^1$ is $C(O)CH_3$, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 494 Compounds of formula (I), wherein A is NH, $R^1$ is $C(O)CH_3$, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 495 Compounds of formula (I), wherein A is $NCH_3$, $R^1$ is $C(O)CH_3$, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 496 Compounds of formula (I), wherein A is $CHC_6H_5$, $R^1$ is $C(O)CH_3$, $R^3$ is $CH_3$, $R^2$ is hydrogen, $R^4$ is $CH_3$ and wherein B, $R^{5.1}$, $R^{5.2}$ and $(R^6)_n$ have the meanings given in one line of table A.

Table 497 Compounds of formula (I), wherein A is $CH_2$, $R^1$ is $C(O)CH_3$, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 498 Compounds of formula (I), wherein A is O, $R^1$ is $C(O)CH_3$, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 499 Compounds of formula (I), wherein A is S, $R^1$ is $C(O)CH_3$, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 500 Compounds of formula (I), wherein A is S(O), $R^1$ is $C(O)CH_3$, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 501 Compounds of formula (I), wherein A is $S(O)_2$, $R^1$ is $C(O)CH_3$, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 502 Compounds of formula (I), wherein A is NH, $R^1$ is $C(O)CH_3$, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 503 Compounds of formula (I), wherein A is $NCH_3$, $R^1$ is $C(O)CH_3$, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 504 Compounds of formula (I), wherein A is $CHC_6H_5$, $R^1$ is $C(O)CH_3$, $R^3$ is $CH_3$, $R^2$ is hydrogen, $R^4$ is phenyl and wherein B, $R^{5.1}$, $R^{5.2}$ and $(R^6)_n$ have the meanings given in one line of table A.

Table 505 Compounds of formula (I), wherein A is $CH_2$, $R^1$ is $C(O)CH_3$, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 506 Compounds of formula (I), wherein A is O, $R^1$ is $C(O)CH_3$, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 507 Compounds of formula (I), wherein A is S, $R^1$ is $C(O)CH_3$, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 508 Compounds of formula (I), wherein A is S(O), $R^1$ is $C(O)CH_3$, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 509 Compounds of formula (I), wherein A is $S(O)_2$, $R^1$ is $C(O)CH_3$, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 510 Compounds of formula (I), wherein A is NH, $R^1$ is $C(O)CH_3$, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 511 Compounds of formula (I), wherein A is $NCH_3$, $R^1$ is $C(O)CH_3$, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 512 Compounds of formula (I), wherein A is $CHC_6H_5$, $R^1$ is $C(O)CH_3$, $R^3$ is $CH_3$, $R^2$ is hydrogen, $R^4$ is benzyl and wherein B, $R^{5.1}$, $R^{5.2}$ and $(R^6)_n$ have the meanings given in one line of table A.

Table 513 Compounds of formula (I), wherein A is $CH_2$, $R^1$ is $C(O)CH_3$, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 514 Compounds of formula (I), wherein A is O, $R^1$ is $C(O)CH_3$, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 515 Compounds of formula (I), wherein A is S, $R^1$ is $C(O)CH_3$, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 516 Compounds of formula (I), wherein A is S(O), $R^1$ is $C(O)CH_3$, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 517 Compounds of formula (I), wherein A is $S(O)_2$, $R^1$ is $C(O)CH_3$, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 518 Compounds of formula (I), wherein A is NH, $R^1$ is $C(O)CH_3$, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 519 Compounds of formula (I), wherein A is $NCH_3$, $R^1$ is $C(O)CH_3$, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 520 Compounds of formula (I), wherein A is $CHC_6H_5$, $R^1$ is $C(O)CH_3$, $R^3$ is $CH_3$, $R^2$ is hydrogen, $R^4$ is allyl and wherein B, $R^{5.1}$, $R^{5.2}$ and $(R^6)_n$ have the meanings given in one line of table A.

Table 521 Compounds of formula (I), wherein A is $CH_2$, $R^1$ is $C(O)CH_3$, $R^3$ is $CH_3$, $R^2$ is $CH_3$, $R^4$ is hydrogen and wherein B, $R^{5.1}$, $R^{5.2}$ and $(R^6)_n$ have the meanings given in any of lines 145 to 1296 of table A.

Table 522 Compounds of formula (I), wherein A is O, $R^1$ is $C(O)CH_3$, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 523 Compounds of formula (I), wherein A is S, $R^1$ is $C(O)CH_3$, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 524 Compounds of formula (I), wherein A is S(O), $R^1$ is $C(O)CH_3$, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 525 Compounds of formula (I), wherein A is $S(O)_2$, $R^1$ is $C(O)CH_3$, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 526 Compounds of formula (I), wherein A is NH, $R^1$ is $C(O)CH_3$, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 527 Compounds of formula (I), wherein A is $NCH_3$, $R^1$ is $C(O)CH_3$, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 528 Compounds of formula (I), wherein A is $CHC_6H_5$, $R^1$ is $C(O)CH_3$, $R^3$ is $CH_3$, $R^2$ is $CH_3$, $R^4$ is hydrogen and wherein B, $R^{5.1}$, $R^{5.2}$ and $(R^6)_n$ have the meanings given in one line of table A.

Table 529 Compounds of formula (I), wherein A is $CH_2$, $R^1$ is $C(O)CH_3$, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 530 Compounds of formula (I), wherein A is O, $R^1$ is $C(O)CH_3$, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 531 Compounds of formula (I), wherein A is S, $R^1$ is $C(O)CH_3$, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 532 Compounds of formula (I), wherein A is S(O), $R^1$ is $C(O)CH_3$, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 533 Compounds of formula (I), wherein A is $S(O)_2$, $R^1$ is $C(O)CH_3$, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 534 Compounds of formula (I), wherein A is NH, $R^1$ is $C(O)CH_3$, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 535 Compounds of formula (I), wherein A is $NCH_3$, $R^1$ is $C(O)CH_3$, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 536 Compounds of formula (I), wherein A is $CHC_6H_5$, $R^1$ is $C(O)CH_3$, $R^3$ is $CH_3$, $R^2$ is $CH_3$, $R^4$ is $CH_3$ and wherein B, $R^{5.1}$, $R^{5.2}$ and $(R^6)_n$ have the meanings given in one line of table A.

Table 537 Compounds of formula (I), wherein A is $CH_2$, $R^1$ is $C(O)CH_3$, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 538 Compounds of formula (I), wherein A is O, $R^1$ is $C(O)CH_3$, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 539 Compounds of formula (I), wherein A is S, $R^1$ is $C(O)CH_3$, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 540 Compounds of formula (I), wherein A is S(O), $R^1$ is $C(O)CH_3$, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 541 Compounds of formula (I), wherein A is $S(O)_2$, $R^1$ is $C(O)CH_3$, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 542 Compounds of formula (I), wherein A is NH, $R^1$ is $C(O)CH_3$, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 543 Compounds of formula (I), wherein A is $NCH_3$, $R^1$ is $C(O)CH_3$, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 544 Compounds of formula (I), wherein A is $CHC_6H_5$, $R^1$ is $C(O)CH_3$, $R^3$ is $CH_3$, $R^2$ is $CH_3$, $R^4$ is phenyl and wherein B, $R^{5.1}$, $R^{5.2}$ and $(R^6)_n$ have the meanings given in one line of table A.

Table 545 Compounds of formula (I), wherein A is $CH_2$, $R^1$ is $C(O)CH_3$, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 546 Compounds of formula (I), wherein A is O, $R^1$ is $C(O)CH_3$, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 547 Compounds of formula (I), wherein A is S, $R^1$ is $C(O)CH_3$, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 548 Compounds of formula (I), wherein A is S(O), $R^1$ is $C(O)CH_3$, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 549 Compounds of formula (I), wherein A is $S(O)_2$, $R^1$ is $C(O)CH_3$, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 550 Compounds of formula (I), wherein A is NH, $R^1$ is $C(O)CH_3$, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 551 Compounds of formula (I), wherein A is $NCH_3$, $R^1$ is $C(O)CH_3$, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 552 Compounds of formula (I), wherein A is $CHC_6H_5$, $R^1$ is $C(O)CH_3$, $R^3$ is $CH_3$, $R^2$ is $CH_3$, $R^4$ is benzyl and wherein B, $R^{5.1}$, $R^{5.2}$ and $(R^6)_n$ have the meanings given in one line of table A.

Table 553 Compounds of formula (I), wherein A is $CH_2$, $R^1$ is $C(O)CH_3$, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 554 Compounds of formula (I), wherein A is O, $R^1$ is $C(O)CH_3$, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 555 Compounds of formula (I), wherein A is S, $R^1$ is $C(O)CH_3$, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 556 Compounds of formula (I), wherein A is S(O), $R^1$ is $C(O)CH_3$, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 557 Compounds of formula (I), wherein A is $S(O)_2$, $R^1$ is $C(O)CH_3$, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 558 Compounds of formula (I), wherein A is NH, $R^1$ is $C(O)CH_3$, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 559 Compounds of formula (I), wherein A is $NCH_3$, $R^1$ is $C(O)CH_3$, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 560 Compounds of formula (I), wherein A is $CHC_6H_5$, $R^1$ is $C(O)CH_3$, $R^3$ is $CH_3$, $R^2$ is $CH_3$, $R^4$ is allyl and wherein B, $R^{5.1}$, $R^{5.2}$ and $(R^6)_n$ have the meanings given in one line of table A.

Table 561 Compounds of formula (I), wherein A is $CH_2$, $R^1$ is $C(O)CH_3$, $R^3$ is $CH_3$, $R^2$ is $COCH_3$, $R^4$ is hydrogen and wherein B, $R^{5.1}$, $R^{5.2}$ and $(R^6)_n$ have the meanings given in any of lines 145 to 1296 of table A.

Table 562 Compounds of formula (I), wherein A is O, $R^1$ is $C(O)CH_3$, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 563 Compounds of formula (I), wherein A is S, $R^1$ is $C(O)CH_3$, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 564 Compounds of formula (I), wherein A is S(O), $R^1$ is $C(O)CH_3$, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 565 Compounds of formula (I), wherein A is $S(O)_2$, $R^1$ is $C(O)CH_3$, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 566 Compounds of formula (I), wherein A is NH, $R^1$ is $C(O)CH_3$, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 567 Compounds of formula (I), wherein A is $NCH_3$, $R^1$ is $C(O)CH_3$, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 568 Compounds of formula (I), wherein A is $CHC_6H_5$, $R^1$ is $C(O)CH_3$, $R^3$ is $CH_3$, $R^2$ is $COCH_3$, $R^4$ is hydrogen and wherein B, $R^{5.1}$, $R^{5.2}$ and $(R^6)_n$ have the meanings given in one line of table A.

Table 569 Compounds of formula (I), wherein A is $CH_2$, $R^1$ is $C(O)CH_3$, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 570 Compounds of formula (I), wherein A is O, $R^1$ is $C(O)CH_3$, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 571 Compounds of formula (I), wherein A is S, $R^1$ is $C(O)CH_3$, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 572 Compounds of formula (I), wherein A is S(O), $R^1$ is $C(O)CH_3$, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 573 Compounds of formula (I), wherein A is $S(O)_2$, $R^1$ is $C(O)CH_3$, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 574 Compounds of formula (I), wherein A is NH, $R^1$ is $C(O)CH_3$, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 575 Compounds of formula (I), wherein A is $NCH_3$, $R^1$ is $C(O)CH_3$, $R^3$ is $CH_3$, $R^2$ is $COCH_3$, $R^4$ is $CH_3$ and wherein B, $R^{5.1}$, $R^{5.2}$ and $(R^6)_n$ have the meanings given in one line of table A.

Table 576 Compounds of formula (I), wherein A is $CHC_6H_5$, $R^1$ is $C(O)CH_3$, $R^3$ is $CH_3$, $R^2$ is $COCH_3$ $R^4$ is $CH_3$ and wherein B, $R^{5.1}$, $R^{5.2}$ and $(R^6)_n$ have the meanings given in one line of table A.

Table 577 Compounds of formula (I), wherein A is $CH_2$, $R^1$ is $C(O)CH_3$, $R^3$ is $CH_3$, $R^2$ is $COCH_3$, $R^4$ is phenyl and wherein B, $R^{5.1}$, $R^{5.2}$ and $(R^6)_n$ have the meanings given in of one line of table A.

Table 578 Compounds of formula (I), wherein A is O, $R^1$ is $C(O)CH_3$, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 579 Compounds of formula (I), wherein A is S, $R^1$ is $C(O)CH_3$, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 580 Compounds of formula (I), wherein A is S(O), $R^1$ is $C(O)CH_3$, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 581 Compounds of formula (I), wherein A is $S(O)_2$, $R^1$ is $C(O)CH_3$, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 582 Compounds of formula (I), wherein A is NH, $R^1$ is $C(O)CH_3$, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 583 Compounds of formula (I), wherein A is $NCH_3$, $R^1$ is $C(O)CH_3$, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 584 Compounds of formula (I), wherein A is $CHC_6H_5$, $R^1$ is $C(O)CH_3$, $R^3$ is $CH_3$, $R^2$ is $COCH_3$, $R^4$ is phenyl and wherein B, $R^{5.1}$, $R^{5.2}$ and $(R^6)_n$ have the meanings given in one line of table A.

Table 585 Compounds of formula (I), wherein A is $CH_2$, $R^1$ is $C(O)CH_3$, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 586 Compounds of formula (I), wherein A is O, $R^1$ is $C(O)CH_3$, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 587 Compounds of formula (I), wherein A is S, $R^1$ is $C(O)CH_3$, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 588 Compounds of formula (I), wherein A is S(O), $R^1$ is $C(O)CH_3$, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 589 Compounds of formula (I), wherein A is $S(O)_2$, $R^1$ is $C(O)CH_3$, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 590 Compounds of formula (I), wherein A is NH, $R^1$ is $C(O)CH_3$, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 591 Compounds of formula (I), wherein A is $NCH_3$, $R^1$ is $C(O)CH_3$, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 592 Compounds of formula (I), wherein A is $CHC_6H_5$, $R^1$ is $C(O)CH_3$, $R^3$ is $CH_3$, $R^2$ is $COCH_3$, $R^4$ is benzyl and wherein B, $R^{5.1}$, $R^{5.2}$ and $(R^6)_n$ have the meanings given in one line of table A.

Table 593 Compounds of formula (I), wherein A is $CH_2$, $R^1$ is $C(O)CH_3$, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 594 Compounds of formula (I), wherein A is O, $R^1$ is $C(O)CH_3$, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 595 Compounds of formula (I), wherein A is S, $R^1$ is $C(O)CH_3$, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 596 Compounds of formula (I), wherein A is S(O), $R^1$ is $C(O)CH_3$, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 597 Compounds of formula (I), wherein A is $S(O)_2$, $R^1$ is $C(O)CH_3$, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 598 Compounds of formula (I), wherein A is NH, $R^1$ is $C(O)CH_3$, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 599 Compounds of formula (I), wherein A is $NCH_3$, $R^1$ is $C(O)CH_3$, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 600 Compounds of formula (I), wherein A is $CHC_6H_5$, $R^1$ is $C(O)CH_3$, $R^3$ is $CH_3$, $R^2$ is $COCH_3$, $R^4$ is allyl and wherein B, $R^{5.1}$, $R^{5.2}$ and $(R^6)_n$ have the meanings given in one line of table A.

Table 601 Compounds of formula (I), wherein A is $CH_2$, $R^1$ is $C(O)CH_3$, $R^3$ is $COCH_3$, $R^2$ is hydrogen, $R^4$ is hydrogen and wherein B, $R^{5.1}$, $R^{5.2}$ and $(R^6)_n$ have the meanings given in any of lines 145 to 1296 of table A.

Table 602 Compounds of formula (I), wherein A is O, $R^1$ is $C(O)CH_3$, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 603 Compounds of formula (I), wherein A is S, $R^1$ is $C(O)CH_3$, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 604 Compounds of formula (I), wherein A is S(O), $R^1$ is $C(O)CH_3$, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 605 Compounds of formula (I), wherein A is $S(O)_2$, $R^1$ is $C(O)CH_3$, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 606 Compounds of formula (I), wherein A is NH, $R^1$ is $C(O)CH_3$, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 607 Compounds of formula (I), wherein A is $NCH_3$, $R^1$ is $C(O)CH_3$, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 608 Compounds of formula (I), wherein A is $CHC_6H_5$, $R^1$ is $C(O)CH_3$, $R^3$ is $COCH_3$, $R^2$ is hydrogen, $R^4$ is hydrogen and wherein B, $R^{5.1}$, $R^{5.2}$ and $(R^6)_n$ have the meanings given in one line of table A.

Table 609 Compounds of formula (I), wherein A is $CH_2$, $R^1$ is $C(O)CH_3$, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 610 Compounds of formula (I), wherein A is O, $R^1$ is $C(O)CH_3$, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 611 Compounds of formula (I), wherein A is S, $R^1$ is $C(O)CH_3$, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 612 Compounds of formula (I), wherein A is S(O), $R^1$ is $C(O)CH_3$, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 613 Compounds of formula (I), wherein A is $S(O)_2$, $R^1$ is $C(O)CH_3$, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 614 Compounds of formula (I), wherein A is NH, $R^1$ is $C(O)CH_3$, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 615 Compounds of formula (I), wherein A is $NCH_3$, $R^1$ is $C(O)CH_3$, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 616 Compounds of formula (I), wherein A is $CHC_6H_5$, $R^1$ is $C(O)CH_3$, $R^3$ is $COCH_3$, $R^2$ is hydrogen, $R^4$ is $CH_3$ and wherein B, $R^{5.1}$, $R^{5.2}$ and $(R^6)_n$ have the meanings given in one line of table A.

Table 617 Compounds of formula (I), wherein A is $CH_2$, $R^1$ is $C(O)CH_3$, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 618 Compounds of formula (I), wherein A is O, $R^1$ is $C(O)CH_3$, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 619 Compounds of formula (I), wherein A is S, $R^1$ is $C(O)CH_3$, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 620 Compounds of formula (I), wherein A is S(O), $R^1$ is $C(O)CH_3$, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 621 Compounds of formula (I), wherein A is $S(O)_2$, $R^1$ is $C(O)CH_3$, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 622 Compounds of formula (I), wherein A is NH, $R^1$ is $C(O)CH_3$, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 623 Compounds of formula (I), wherein A is $NCH_3$, $R^1$ is $C(O)CH_3$, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 624 Compounds of formula (I), wherein A is $CHC_6H_5$, $R^1$ is $C(O)CH_3$, $R^3$ is $COCH_3$, $R^2$ is hydrogen, $R^4$ is phenyl and wherein B, $R^{5.1}$, $R^{5.2}$ and $(R^6)_n$ have the meanings given in one line of table A.

Table 625 Compounds of formula (I), wherein A is $CH_2$, $R^1$ is $C(O)CH_3$, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 626 Compounds of formula (I), wherein A is O, $R^1$ is $C(O)CH_3$, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 627 Compounds of formula (I), wherein A is S, $R^1$ is $C(O)CH_3$, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 628 Compounds of formula (I), wherein A is S(O), $R^1$ is $C(O)CH_3$, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 629 Compounds of formula (I), wherein A is $S(O)_2$, $R^1$ is $C(O)CH_3$, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 630 Compounds of formula (I), wherein A is NH, $R^1$ is $C(O)CH_3$, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 631 Compounds of formula (I), wherein A is $NCH_3$, $R^1$ is $C(O)CH_3$, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 632 Compounds of formula (I), wherein A is $CHC_6H_5$, $R^1$ is $C(O)CH_3$, $R^3$ is $COCH_3$, $R^2$ is hydrogen, $R^4$ is benzyl and wherein B, $R^{5.1}$, $R^{5.2}$ and $(R^6)_n$ have the meanings given in one line of table A.

Table 633 Compounds of formula (I), wherein A is $CH_2$, $R^1$ is $C(O)CH_3$, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 634 Compounds of formula (I), wherein A is O, $R^1$ is $C(O)CH_3$, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 635 Compounds of formula (I), wherein A is S, $R^1$ is $C(O)CH_3$, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 636 Compounds of formula (I), wherein A is S(O), $R^1$ is $C(O)CH_3$, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 637 Compounds of formula (I), wherein A is $S(O)_2$, $R^1$ is $C(O)CH_3$, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 638 Compounds of formula (I), wherein A is NH, $R^1$ is $C(O)CH_3$, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 639 Compounds of formula (I), wherein A is $NCH_3$, $R^1$ is $C(O)CH_3$, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 640 Compounds of formula (I), wherein A is $CHC_6H_5$, $R^1$ is $C(O)CH_3$, $R^3$ is $COCH_3$, $R^2$ is hydrogen, $R^4$ is allyl and wherein B, $R^{5.1}$, $R^{5.2}$ and $(R^6)_n$ have the meanings given in one line of table A.

Table 641 Compounds of formula (I), wherein A is $CH_2$, $R^1$ is $C(O)CH_3$, $R^3$ is $COCH_3$, $R^2$ is $CH_3$, $R^4$ is hydrogen and wherein B, $R^{5.1}$, $R^{5.2}$ and $(R^6)_n$ have the meanings given in any of lines 145 to 1296 of table A.

Table 642 Compounds of formula (I), wherein A is O, $R^1$ is $C(O)CH_3$, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 643 Compounds of formula (I), wherein A is S, $R^1$ is $C(O)CH_3$, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 644 Compounds of formula (I), wherein A is S(O), $R^1$ is $C(O)CH_3$, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 645 Compounds of formula (I), wherein A is $S(O)_2$, $R^1$ is $C(O)CH_3$, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 646 Compounds of formula (I), wherein A is NH, $R^1$ is $C(O)CH_3$, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 647 Compounds of formula (I), wherein A is $NCH_3$, $R^1$ is $C(O)CH_3$, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 648 Compounds of formula (I), wherein A is $CHC_6H_5$, $R^1$ is $C(O)CH_3$, $R^3$ is $COCH_3$, $R^2$ is $CH_3$, $R^4$ is hydrogen and wherein B, $R^{5.1}$, $R^{5.2}$ and $(R^6)_n$ have the meanings given in one line of table A.

Table 649 Compounds of formula (I), wherein A is $CH_2$, $R^1$ is $C(O)CH_3$, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 650 Compounds of formula (I), wherein A is O, $R^1$ is $C(O)CH_3$, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 65.1 Compounds of formula (I), wherein A is S, $R^1$ is $C(O)CH_3$, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 652 Compounds of formula (I), wherein A is S(O), $R^1$ is $C(O)CH_3$, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 653 Compounds of formula (I), wherein A is $S(O)_2$, $R^1$ is $C(O)CH_3$, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 654 Compounds of formula (I), wherein A is NH, $R^1$ is $C(O)CH_3$, $R^3$ is $COCH_3$, $R^2$ is $CH_3$, $R^4$ is $CH_3$ and wherein B, $R^{5.1}$, $R^{5.2}$ and $(R^6)_n$ have the meanings given in one line of table A.

Table 655 Compounds of formula (I), wherein A is $NCH_3$, $R^1$ is $C(O)CH_3$, $R^3$ is $COCH_3$, $R^2$ is $CH_3$ $R^4$ is $CH_3$ and wherein B, $R^{5.1}$, $R^{5.2}$ and $(R^6)_n$ have the meanings given in one line of table A.

Table 656 Compounds of formula (I), wherein A is $CHC_6H_5$, $R^1$ is $C(O)CH_3$, $R^3$ is $COCH_3$, $R^2$ is $CH_3$ $R^4$ is $CH_3$ and wherein B, $R^{5.1}$, $R^{5.2}$ and $(R^6)_n$ have the meanings given in one line of table A.

Table 657 Compounds of formula (I), wherein A is $CH_2$, $R^1$ is $C(O)CH_3$, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 658 Compounds of formula (I), wherein A is O, $R^1$ is $C(O)CH_3$, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 659 Compounds of formula (I), wherein A is S, $R^1$ is $C(O)CH_3$, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 660 Compounds of formula (I), wherein A is S(O), $R^1$ is $C(O)CH_3$, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 661 Compounds of formula (I), wherein A is $S(O)_2$, $R^1$ is $C(O)CH_3$, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 662 Compounds of formula (I), wherein A is NH, $R^1$ is $C(O)CH_3$, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 663 Compounds of formula (I), wherein A is $NCH_3$, $R^1$ is $C(O)CH_3$, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 664 Compounds of formula (I), wherein A is $CHC_6H_5$, $R^1$ is $C(O)CH_3$, $R^3$ is $COCH_3$, $R^2$ is $CH_3$, $R^4$ is phenyl and wherein B, $R^{5.1}$, $R^{5.2}$ and $(R^6)_n$ have the meanings given in one line of table A.

Table 665 Compounds of formula (I), wherein A is $CH_2$, $R^1$ is $C(O)CH_3$, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 666 Compounds of formula (I), wherein A is O, $R^1$ is $C(O)CH_3$, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 667 Compounds of formula (I), wherein A is S, $R^1$ is $C(O)CH_3$, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 668 Compounds of formula (I), wherein A is S(O), $R^1$ is $C(O)CH_3$, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 669 Compounds of formula (I), wherein A is $S(O)_2$, $R^1$ is $C(O)CH_3$, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 670 Compounds of formula (I), wherein A is NH, $R^1$ is $C(O)CH_3$, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 671 Compounds of formula (I), wherein A is $NCH_3$, $R^1$ is $C(O)CH_3$, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 672 Compounds of formula (I), wherein A is $CHC_6H_5$, $R^1$ is $C(O)CH_3$, $R^3$ is $COCH_3$, $R^2$ is $CH_3$, $R^4$ is benzyl and wherein B, $R^{5.1}$, $R^{5.2}$ and $(R^6)_n$ have the meanings given in one line of table A.

Table 673 Compounds of formula (I), wherein A is $CH_2$, $R^1$ is $C(O)CH_3$, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 674 Compounds of formula (I), wherein A is O, $R^1$ is $C(O)CH_3$, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 675 Compounds of formula (I), wherein A is S, $R^1$ is $C(O)CH_3$, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 676 Compounds of formula (I), wherein A is S(O), $R^1$ is $C(O)CH_3$, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 677 Compounds of formula (I), wherein A is $S(O)_2$, $R^1$ is $C(O)CH_3$, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 678 Compounds of formula (I), wherein A is NH, $R^1$ is $C(O)CH_3$, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 679 Compounds of formula (I), wherein A is $NCH_3$, $R^1$ is $C(O)CH_3$, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 680 Compounds of formula (I), wherein A is $CHC_6H_5$, $R^1$ is $C(O)CH_3$, $R^3$ is $COCH_3$, $R^2$ is $CH_3$, $R^4$ is allyl and wherein B, $R^{5.1}$, $R^{5.2}$ and $(R^6)_n$ have the meanings given in one line of table A.

Table 681 Compounds of formula (I), wherein A is $CH_2$, $R^1$ is $C(O)CH_3$, $R^3$ is $COCH_3$, $R^2$ is $COCH_3$, $R^4$ is hydrogen and wherein B, $R^{5.1}$, $R^{5.2}$ and $(R^6)_n$ have the meanings given in any of lines 145 to 1296 of table A.

Table 682 Compounds of formula (I), wherein A is O, $R^1$ is $C(O)CH_3$, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 683 Compounds of formula (I), wherein A is S, $R^1$ is $C(O)CH_3$, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 684 Compounds of formula (I), wherein A is S(O), $R^1$ is $C(O)CH_3$, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 685 Compounds of formula (I), wherein A is $S(O)_2$, $R^1$ is $C(O)CH_3$, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 686 Compounds of formula (I), wherein A is NH, $R^1$ is $C(O)CH_3$, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 687 Compounds of formula (I), wherein A is $NCH_3$, $R^1$ is $C(O)CH_3$, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 688 Compounds of formula (I), wherein A is $CHC_6H_5$, $R^1$ is $C(O)CH_3$, $R^3$ is $COCH_3$, $R^2$ is $COCH_3$, $R^4$ is hydrogen and wherein B, $R^{5.1}$, $R^{5.2}$ and $(R^6)_n$ have the meanings given in one line of table A.

Table 689 Compounds of formula (I), wherein A is $CH_2$, $R^1$ is $C(O)CH_3$, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 690 Compounds of formula (I), wherein A is O, $R^1$ is $C(O)CH_3$, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 691 Compounds of formula (I), wherein A is S, $R^1$ is $C(O)CH_3$, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 692 Compounds of formula (I), wherein A is S(O), $R^1$ is $C(O)CH_3$, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 693 Compounds of formula (I), wherein A is $S(O)_2$, $R^1$ is $C(O)CH_3$, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 694 Compounds of formula (I), wherein A is NH, $R^1$ is $C(O)CH_3$, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 695 Compounds of formula (I), wherein A is $NCH_3$, $R^1$ is $C(O)CH_3$, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 696 Compounds of formula (I), wherein A is $CHC_6H_5$, $R^1$ is $C(O)CH_3$, $R^3$ is $COCH_3$, $R^2$ is $COCH_3$, $R^4$ is $CH_3$ and wherein B, $R^{5.1}$, $R^{5.2}$ and $(R^6)_n$ have the meanings given in one line of table A.

Table 697 Compounds of formula (I), wherein A is $CH_2$, $R^1$ is $C(O)CH_3$, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 698 Compounds of formula (I), wherein A is O, $R^1$ is $C(O)CH_3$, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 699 Compounds of formula (I), wherein A is S, $R^1$ is $C(O)CH_3$, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 700 Compounds of formula (I), wherein A is S(O), $R^1$ is $C(O)CH_3$, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 701 Compounds of formula (I), wherein A is $S(O)_2$, $R^1$ is $C(O)CH_3$, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 702 Compounds of formula (I), wherein A is NH, $R^1$ is $C(O)CH_3$, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 703 Compounds of formula (I), wherein A is $NCH_3$, $R^1$ is $C(O)CH_3$, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 704 Compounds of formula (I), wherein A is $CHC_6H_5$, $R^1$ is $C(O)CH_3$, $R^3$ is $COCH_3$, $R^2$ is $COCH_3$, $R^4$ is phenyl and wherein B, $R^{5.1}$, $R^{5.2}$ and $(R^6)_n$ have the meanings given in one line of table A.

Table 705 Compounds of formula (I), wherein A is $CH_2$, $R^1$ is $C(O)CH_3$, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 706 Compounds of formula (I), wherein A is O, $R^1$ is $C(O)CH_3$, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 707 Compounds of formula (I), wherein A is S, $R^1$ is $C(O)CH_3$, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 708 Compounds of formula (I), wherein A is S(O), $R^1$ is $C(O)CH_3$, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 709 Compounds of formula (I), wherein A is $S(O)_2$, $R^1$ is $C(O)CH_3$, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 710 Compounds of formula (I), wherein A is NH, $R^1$ is $C(O)CH_3$, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 711 Compounds of formula (I), wherein A is $NCH_3$, $R^1$ is $C(O)CH_3$, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 712 Compounds of formula (I), wherein A is $CHC_6H_5$, $R^1$ is $C(O)CH_3$, $R^3$ is $COCH_3$, $R^2$ is $COCH_3$, $R^4$ is benzyl and wherein B, $R^{5.1}$, $R^{5.2}$ and $(R^6)_n$ have the meanings given in one line of table A.

Table 713 Compounds of formula (I), wherein A is $CH_2$, $R^1$ is $C(O)CH_3$, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 714 Compounds of formula (I), wherein A is O, $R^1$ is $C(O)CH_3$, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 715 Compounds of formula (I), wherein A is S, $R^1$ is $C(O)CH_3$, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 716 Compounds of formula (I), wherein A is S(O), $R^1$ is $C(O)CH_3$, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 717 Compounds of formula (I), wherein A is $S(O)_2$, $R^1$ is $C(O)CH_3$, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 718 Compounds of formula (I), wherein A is NH, $R^1$ is $C(O)CH_3$, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 719 Compounds of formula (I), wherein A is $NCH_3$, $R^1$ is $C(O)CH_3$, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Table 720 Compounds of formula (I), wherein A is $CHC_6H_5$, $R^1$ is $C(O)CH_3$, $R^3$ is $COCH_3$, $R^2$ is $COCH_3$, $R^4$ is allyl and wherein B, $R^{5.1}$, $R^{5.2}$ and $(R^6)_n$ have the meanings given in one line of table A.

Preparation Methods

Compound of formula (I) according to the present invention can be prepared e.g. according the preparation methods and preparation schemes as described below.

Amines (II) are known in the art or can be prepared by methods familiar to an organic chemist, for instance by application of general methods for the synthesis of amines. Suitable amine salts (IV) are e.g. the acid addition salts formed by treating an amine (IV) with an inorganic or organic acid. Anions of useful acids are e.g. sulfate, hydrogen sulfate, phosphate, dihydrogen phosphate, hydrogen phosphate, nitrate, bicarbonate, carbonate, chloride, bromide, p-toluene sulfonate, and the anions of $C_1$-$C_4$-alkanoic acids such as acetate, propionate, and the like.

For instance, amines (II) can be prepared from suitable ketones (III) by the methods depicted in schemes 1 and 2 below.

Scheme 1:

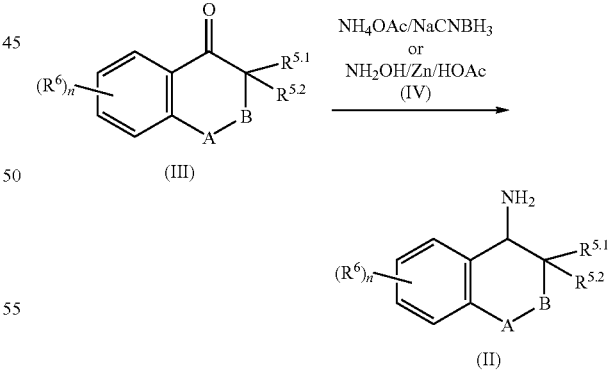

Amines (II) wherein $R^4$ is hydrogen can be obtained through reductive amination using e.g. $NH_4OAc$ and $NaCNBH_3$ or $NH_2OH/Zn/HOAc$ (see R. C. Larock, Comprehensive Organic Transformations $2^{nd}$ Ed., Wiley-VCH, 1999, p. 843-846). Alternatively compounds (II) can be prepared by reduction of the ketone (III) and subsequent amination of the resulting alcohol (see Mitsunobu, Hughes, Organic Reactions 1992, 42, 335-656). Compounds (II) wherein A is O or S can be prepared in analogues manner to the method described in Turan-Zitouni et al. Turk. Farmaco, Edizione Scientifica (1988), 43, 643-55 or P. Sebok et al. Heterocyclic Communications, 1998, 4, 547-557.

Scheme 2:

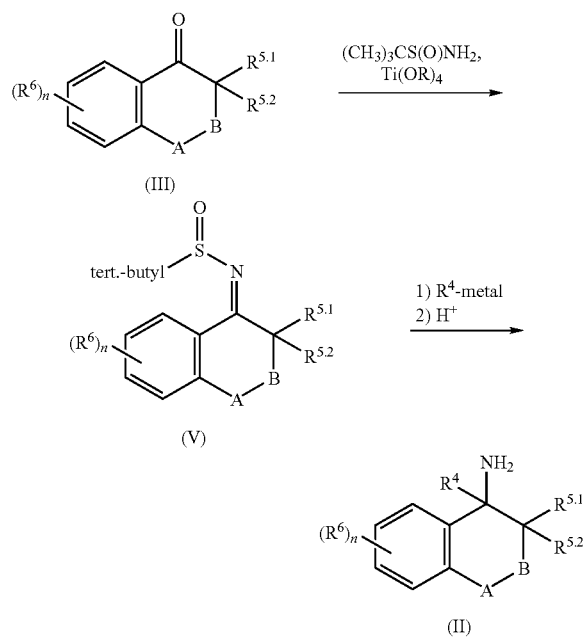

Amines (II) wherein $R^4$ is different from hydrogen can be obtained from the ketone (III) via a two step synthesis. In a first step the ketone is reacted with a suitable sulfinamide such as (2-methyl-2-propane)sulfinamide in presence of a Lewis acid such as titanium tetraalkylate. The radical $R^4$ is subsequently introduced via a nucleophilic addition of some metallorganic compound followed by protonation and deprotection of the amino group.

Suitable ketones (III) are known in the art or can be prepared by methods familiar to an organic chemist, for instance by application of general methods for the synthesis of ketones. Schemes 3 and 4 below illustrate some synthetic routes towards substituted ketones (III).

Scheme 3:

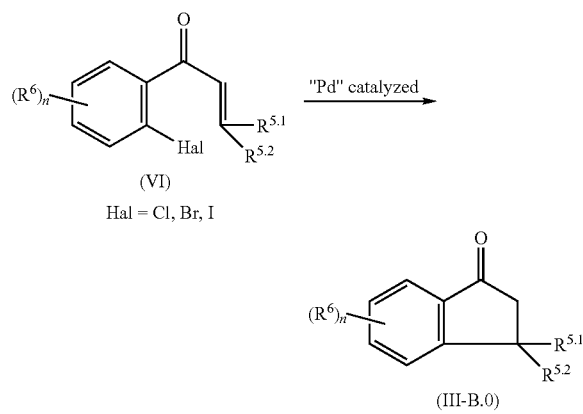

Hal = Cl, Br, I

For instance ketones (III) wherein A is $C(R^{4.1})(R^{4.2})$ and B is a chemical bond (III-B.0) can be obtained from a suitable halogenated phenyl (VI) via a palladium-catalyzed Heck-type cyclization. The preparation of 3-substituted indanones is for instance described in A. Pueschl, H. C. Rudbeck, A. Faldt, A. Confante, J. Kehler Synthesis 2005, 291-295.

Scheme 4:

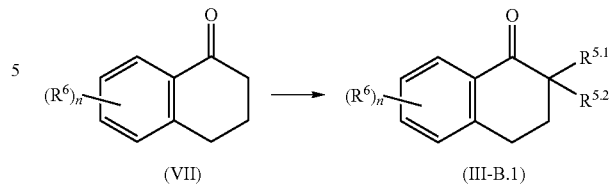

For instance ketones (III) wherein at least one of the radicals $R^{5.1}$ or $R^{5.2}$ is different from hydrogen and B is $CH_2$ (III-B.1) can be obtained from a suitable α,α unsubstituted ketone (VII) via alkylation or palladium-catalyzed arylation (see M. Palucki, S. L. Buchwald J. Am. Chem. Soc. 1997, 119, 11108-11109 or J. M. Fox, X. Huang, A. Chieffi, S. L. Buchwald J. Am. Chem. Soc. 2000, 122, 1360-1370) of the enolate species.

Alternatively α-substituted ketones (III) can be obtained from an intramolecular Friedel-Crafts-Acylation of a suitable aromatic acid chloride (see Y. Oshiro et al. J. Med. Chem. 1991, 34, 2004-2013 or W. Vaccaro et al. J. Med. Chem. 1996, 39, 1704-1719)

Scheme 5:

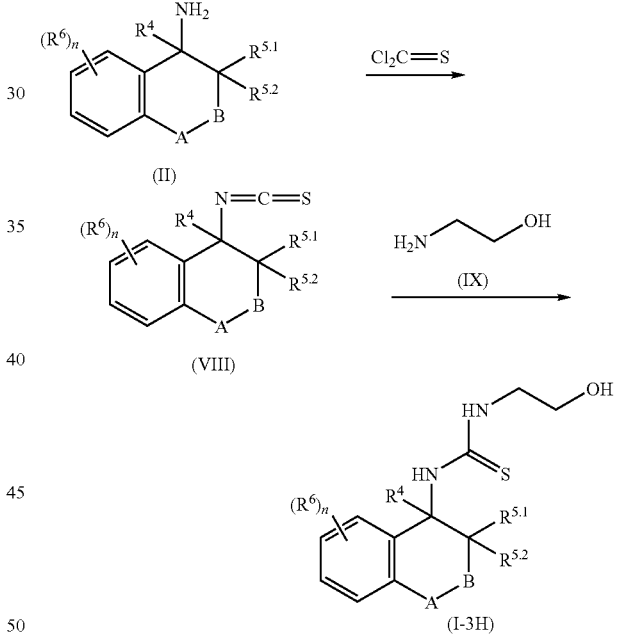

An amine (II) or a salt thereof is converted to the corresponding isothiocyanate (VIII) by conventional means, e.g. by reacting (II) with thiophosgene, as described for example in Houben-Weyl, E4, "Methoden der Organischen Chemie", chapter IIc, pp. 837-842, Georg Thieme Verlag 1983. It may be advantageous to carry out the reaction in the presence of a base. The isothiocyanate (VIII) is then reacted with aminoethanol (IX) to form an aminothiocarbonylaminoethane compound (1-3H). The reaction of the aminoethanol (IX) with isothiocyanate (VIII) can be performed in accordance with standard methods of organic chemistry, see e.g. Biosci. Biotech. Biochem. 56 (7), 1062-65 (1992).

Alternatively, the compounds of formula (I) of the present invention can also be e.g. prepared from the corresponding substituted amines (II-$R^3$) by the synthetic route outlined in the following scheme:

Scheme 6:

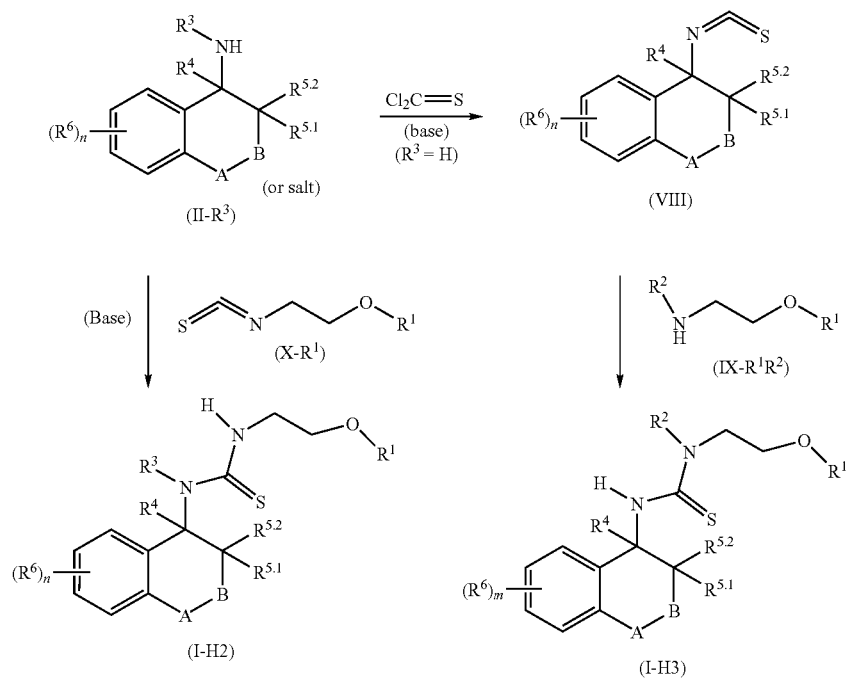

According to the method outlined in scheme 6, an amine (II-R³) (or its salt) is converted to the corresponding isothiocyanate (VIII) by conventional means, e.g. by reacting (II-R³) with thiophosgene (see e.g. Houben-Weyl, E4, "Methoden der Organischen Chemie", chapter IIc, pp. 837-842, Georg Thieme Verlag 1983. The isothiocyanate (VIII) is then reacted with an aminoethanol (IX-R¹R²), thereby obtaining the substituted thiourea compound (I-H3).

The reaction of the aminoethanol (IX-R¹R²) with corresponding isothiocyanate (VIII) can be performed in accordance with standard methods of organic chemistry, see e.g. Biosci. Biotech. Biochem. 56 (7), 1062-65 (1992).

Compounds of the formula (I-H2) and (I-H3) can be further converted into new compounds of the general formula I by modification of R¹. In particular if R¹ is hydrogen these compounds (I-H1) can e.g. converted by esterification reactions e.g. with carboxylic acids or carboxylic acid chlorides by methods familiar to an organic chemist and well known in the art, as outlined in the following scheme and described below.

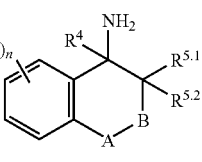

-continued

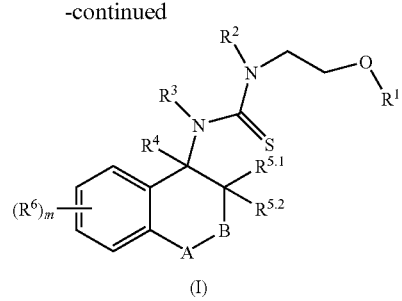

Another method for preparing compounds of formula (I-3H), wherein R¹, R² and R³ are H is shown in scheme 7.

Scheme 7:

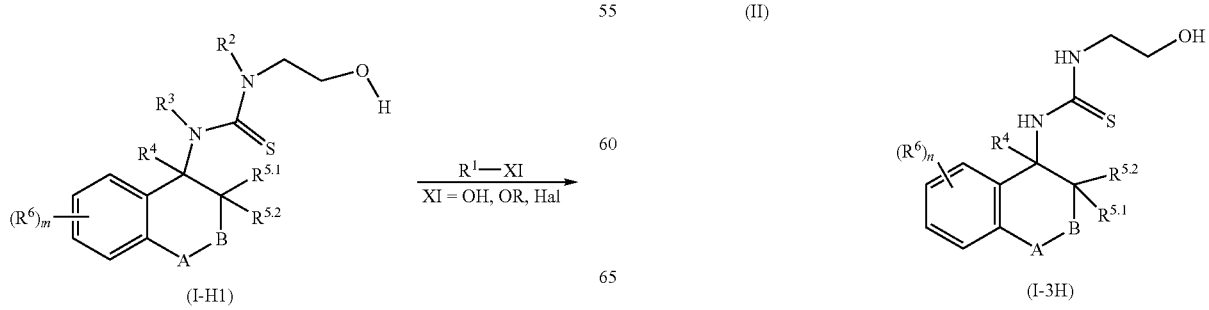

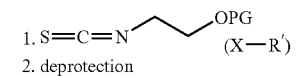

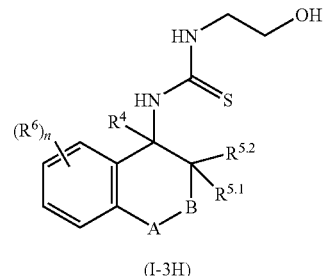

wherein PG is a suitable protecting group as it is well known in the art (Greene, Wuts, Protective Groups in Organic Synthesis, 3$^{rd}$. Ed., John Wiley & Sons, Inc., 1999.)

An amine (II) or a salt thereof can be converted to the corresponding thiourea compound (I-3H), by reacting the amine (II) with an isothiocyanate (X-R') and subsequent deprotection (see e.g. G. Liu et al. J. Org. Chem. 1999, 64, 1278-1284). Isothiocyanates of formula (X-R') can be prepared according to the procedures described in Coll. Czech. Chem. Commun. 1986, 51, 112-117.

The substituted thiourea compounds according to the present invention can be prepared according to the general preparation schemes as described above. If not otherwise specifically defined, the substituents A, B, $R^1$, $R^2$, $R^3$, $R^4$, $R^{5.1}$, $R^{5.2}$ and $R^6$ are defined as above.

As a rule, the thiourea compounds of the formula (I) can be prepared by the methods described above. Some of the preparation methods described above can also be found in WO2007/060120. However, in individual cases, certain compounds I can also advantageously be prepared from other compounds I by ester hydrolysis, amidation, esterification, ether cleavage, olefination, reduction, oxidation and the like.

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Pests

The compounds of the formula I, and their salts are in particular suitable for efficiently controlling arthropodal pests such as arachnids, myriapedes and insects as well as nematodes.

The compounds of the formula I are especially suitable for efficiently combating the following pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga sp., Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (Blattaria-Blattodea), e.g. *Blattella germanica, Blattella asahinae, Periplaneta americana, Periplaneta*

*japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulocorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

They are also suitable for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina species;* Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the formula I and their salts are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni;* Tarsonemidae spp. such as *Phytonemus*

*pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and *Tetranychus urticae, Panonychus ulmi, Panonychus citri*, and oligonychus pratensis.

Compounds of the formula I are particularly useful for controlling insects, preferably sucking or piercing insects such as insects from the genera *Thysanoptera, Diptera* and *Hemiptera*, in particular the following species:

Thysanoptera: *Frankliniella fusca, Frankliniella occidentalis, Frankliniella tritici, Scirtothrips citri, Thrips oryzae, Thrips palmi* and *Thrips tabaci*, Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pornonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla pin, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii;*

Compounds of the formula I are particularly useful for controlling insects of the orders Hemiptera and Thysanoptera, and more preferably for controlling aphids.

Formulations

For use in a method according to the present invention, the compounds I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-methyl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal Suitable thickeners are compounds which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:
1. Products for dilution with water. For seed treatment purposes, such products may be applied to the seed diluted or undiluted.
A) Water-Soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.
B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.
C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.
D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.
E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.
F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the method of this invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphates: acephate, azamethiphos, azinphos-ethyl, azinphosmethyl, chlorethoxyfos, chlorfenvinphos, chlormephos, chlorpyrifos, chlorpyrifosmethyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-, yfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, resmethrin, RU 15525, silafluofen, tefluthrin, tetramethrin, tralomethrin, transfluthrin, ZXI 8901;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), thiacloprid, thiocyclam, thiosultap-sodium and AKD1022.

M.6. GABA gated chloride channel antagonist compounds: chlordane, endosulfan, gamma-HCH (lindane); acetoprole, ethiprole, fipronil, pyrafluprole, pyriprole, vaniliprole, the phenylpyrazole compound of formula $M^{6.1}$

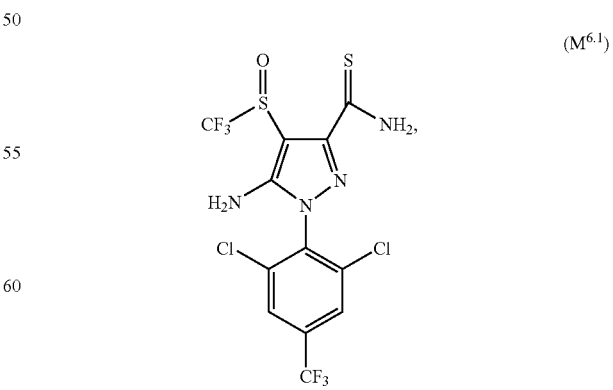

M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. octapaminergic agonsits: amitraz;

M.21. ryanodine receptor modulators: flubendiamide;

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoximine compounds $M^{22.1}$

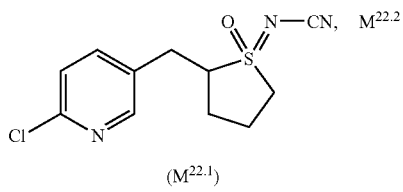

($M^{22.1}$)

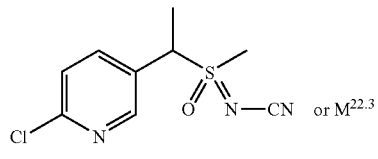

($M^{22.2}$)

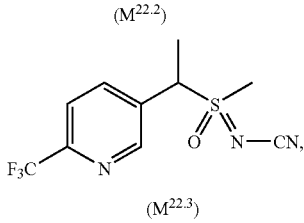

($M^{22.3}$)

pyrimidinyl alkynylether compounds $M^{22.4}$ or thiadiazolyl alkynylether compounds $M^{22.5}$:

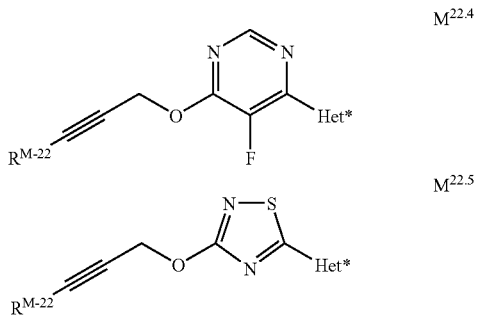

wherein $R^{M-22}$ is methyl or ethyl and Het* is 3,3-dimethylpyrrolidin-1-yl, 3-methylpiperidin-1-yl, 3,5-dimethylpiperidin-1-yl, 3-trifluormethylpiperidin-1-yl, hexa-hydroazepin-1-yl, 2,6-dimethylhexahydroazepin-1-yl or 2,6-dimethylmorpholin-4-yl;

M.23. N-R'-2,2-dihalo-1-R"cyclo-propanecarboxamide-2-(2,6-dichloro-α,α,α-tri-fluoro-p-tolyl)hydrazone or N-R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl;

M.24. Anthranilamides: chloranthraniliprole (Rynaxypyr™), the compound of formula $M^{24.1}$ (Cyazypyr™)

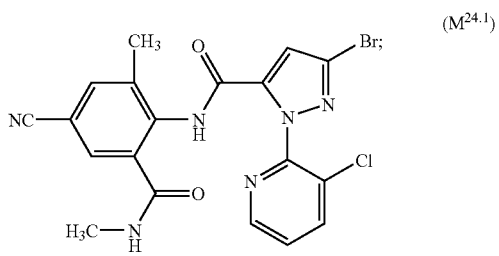

M.25. Malononitrile compounds: $CF_2HCF_2CF_2CF_2CH_2C(CN)_2CH_2CH_2CF_3$ (2-(2,2,3,3,4,4,5,5-octafluoropentyl)-2-(3,3,3-trifluoro-propyl)malononitrile), $CF_3(CH_2)_2C(CN)_2CH_2(CF_2)_5CF_2H$, (2-(2,2,3,3,4,4,5,5,6,6,7,7-Dodecafluoro-heptyl)-2-(3,3,3-trifluoro-propyl)-malononitrile), $CF_3(CH_2)_2C(CN)_2(CH_2)_2C(CF_3)_2F$ (2-(3,4,4,4-Tetrafluoro-3-trifluoromethyl-butyl)-2-(3,3,3-trifluoro-propyl)-malononitrile), $CF_3(CH_2)_2C(CN)_2(CH_2)_2(CF_2)_3CF_3$ (2-(3,3,4,4,5,5,6,6,6-Nonafluoro-hexyl)-2-(3,3,3-trifluoro-propyl)-malononitrile), $CF_2H(CF_2)_3CH_2C(CN)_2CH_2(CF_2)_3CF_2H$ (2,2-Bis-(2,2,3,3,4,4,5,5-octafluoro-pentyl)-malononitrile), $CF_3(CH_2)_2C(CN)_2CH_2(CF_2)_3CF_3$ (2-(2,2,3,3,4,4,5,5,5-Nonafluoro-pentyl)-2-(3,3,3-trifluoro-propyl)-malononitrile), $CF_3(CF_2)_2CH_2C(CN)_2CH_2(CF_2)_3CF_2H$ (2-(2,2,3,3,4,4,4-Heptafluoro-butyl)-2-(2,2,3,3,4,4,5,5-octafluoro-pentyl)-malononitrile), $CF_3CF_2CH_2C(CN)_2CH_2(CF_2)_3CF_2H$ (2-(2,2,3,3,4,4,5,5-Octafluoro-pentyl)-2-(2,2,3,3,3-pentafluoro-propyl)-malononitrile), $CF_2HCF_2CF_2CF_2CH_2C(CN)_2CH_2CH_2CF_3$ (2-(2,2,3,3,4,4,5,5-octafluoropentyl)-2-(3,3,4,4,4-pentafluorobutyl)-malonodinitrile), $CF_3(CH_2)_2C(CN)_2CH_2(CF_2)_3CF_2H$ (2-(2,2,3,3,4,4,5,5-octafluoropentyl)-2-(3,3,3-trifluoro-butyl)-malononitrile);

M.26. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

The commercially available compounds of the group M may be found in The Pesticide Manual, 13$^{th}$ Edition, British Crop Protection Council (2003) among other publications.

Thioamides of formula $M^{6.1}$ and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Anthranilamide derivatives of formula $M^{24.1}$ have been described in WO 01/70671, WO 04/067528 and WO 05/118552. Cyflumetofen and its preparation have been described in WO 04/080180. The aminoquinazolinone compound pyrifluquinazon has been described in EP A 109 7932. Sulfoximine derivatives of formulae $M^{22.1}$, $M^{22.2}$ or $M^{22.3}$ or in analogy thereof and their preparation methods have been described in WO 2006/060029. The alkynylether compounds $M^{22.4}$ and $M^{22.5}$ are described e.g. in JP 2006131529. Organic sulfur compounds have been described in WO 2007060839. The malononitrile compounds have been described in WO 02/089579, WO 02/090320, WO 02/090321, WO 04/006677, WO 05/068423, WO 05/068432 and WO 05/063694.

Fungicidal mixing partners are those selected from the group F consisting of

F.1 acylalanines such as benalaxyl, metalaxyl, ofurace, oxadixyl;

F.2 amine derivatives such as aldimorph, dodine, dodemorph, fenpropimorph, fenpropidin, guazatine, iminoctadine, spiroxamin, tridemorph;

F.3 anilinopyrimidines such as pyrimethanil, mepanipyrim or cyrodinyl;

F.4 antibiotics such as cycloheximid, griseofulvin, kasugamycin, natamycin, polyoxin or streptomycin;

F.5 azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

F.6 dicarboximides such as iprodion, myclozolin, procymidon, vinclozolin;

F.7 dithiocarbamates such as ferbam, nabam, maneb, mancozeb, metam, metiram, propineb, polycarbamate, thiram, ziram, zineb;

F.8 heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

F.9 copper fungicides such as Bordeaux mixture, copper acetate, copper oxychloride, basic copper sulfate;

F.10 nitrophenyl derivatives such as binapacryl, dinocap, dinobuton, nitrophthalisopropyl;

F.11 phenylpyrroles such as fenpiclonil or fludioxonil;

F.12 strobilurins such as azoxystrobin, dimoxystrobin, fluoxastrobin, kresoxim-methyl, metominostrobin, orysastrobin, picoxystrobin or trifloxystrobin;

F.13 sulfenic acid derivatives such as captafol, captan, dichlofluanid, folpet, tolylfluanid;

F.14 cinnemamides and analogs such as dimethomorph, flumetover or flumorph;

F.15 sulfur, and other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentinacetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid.

Applications

The animal pest, i.e. the insects, arachnids and nematodes, the plant, soil or water in which the plant is growing can be contacted with the present compounds of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5):1225-35., Curr Opin Chem Biol. 2006 October; 10(5):487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e. g. EP-A-0242236, EP-A-242246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e. g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e. g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e. g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e. g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitoes, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g in spray cans), oil sprays or pump sprays are highly suitable for the non-professional user for controlling pests such as flies, fleas, ticks, mosquitoes or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysanthemate (Esbiothrin), a repellent derived from or identical with plant extracts like limonene, eugenol, (+)-Eucamalol (1), (−)-1-epi-eucamalol or crude plant extracts from plants like *Eucalyptus maculate, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably aa method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a Gelling Agent is Carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or the enantiomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the enantiomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus,*

*Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:
Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum,*

*Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)
Spirurida, e.g. *Thelazia* spp. *Wuchereria* spp., *Brugia* spp., *Onchocerca* spp., *Dirofilari* spp. a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):
Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-sodium N-lauryl-p-iminodipropionate or lecithin;
anionic surfactants, such as sodium lauryl sulfate, fatty alcohol ether sulfates, mono/dialkyl polyglycol ether orthophosphoric acid ester monoethanolamine salt;
cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 per cent by weight, preferably from 0.1 to 65 per cent by weight, more preferably from 1 to 50 per cent by weight, most preferably from 5 to 40 per cent by weight.

Preparations which are diluted before use contain the compounds acting against ectoparasites in concentrations of 0.5 to 90 per cent by weight, preferably of 1 to 50 per cent by weight.

Furthermore, the preparations comprise the compounds of formula I against endoparasites in concentrations of 10 ppm to 2 per cent by weight, preferably of 0.05 to 0.9 per cent by weight, very particularly preferably of 0.005 to 0.25 per cent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The present invention is now illustrated in further details by the following examples.

EXAMPLES

S. Synthesis Examples

S.1 Synthesis of 1-(5-Fluoro-2,3-dihydro-benzofuran-3-yl)-3-(2-hydroxy-ethyl)-thiourea (Compound Example C.1 of Table C)

A solution of the corresponding isothiocyanate derivate (1.90 g, 9.7 mmol) of the title compound and 2-amino ethanol (0.89 g, 14.6 mmol) in $CHCl_3$ (25 mL) was heated to 60° C. for 2 hours. After cooling to room temperature, the reaction mixture was poured into ethyl acetate (150 mL) and extracted with water (6 times). The organic phase was dried over $Na_2SO_4$ and the solvents evaporated to yield 1-(5-Fluoro-2,3-dihydro-benzofuran-3-yl)-3-(2-hydroxy-ethyl)-thiourea (2.30 g, 9.0 mmol, 92%).

S.2 Synthesis of 7-fluoro-2,3-dihydro-benzo[b]thiophen-3-yl)-3-(2-hydroxy-ethyl)-thiourea (Compound Example C.2 of Table C)

Compound C.2 of table C was prepared in analogy to synthesis example S.1 above.

S.3 Synthesis of Acetic acid 2-[3-(7-fluoro-2,3-dihydro-benzo[b]thiophen-3-yl)thioureido]-ethyl ester (Compound Example C.3 of Table C)

To a solution of 1-(7-Fluoro-2,3-dihydro-benzo[b]thiophen-3-yl)-3-(2-hydroxy-ethyl)-thiourea (200 mg, 0.73 mmol), pyridine (0.07 mL, 0.88 mmol) and DMAP (20 mg, 0.16 mmol) in THF (5 mL) was added a solution of acetyl chloride (0.06 mL, 0.81 mmol) in THF (2 mL) and the reaction mixture stirred for 16 h. The mixture was diluted with ethyl acetate (20 mL) and extracted with water (4 times). The organic phase was dried over $Na_2SO_4$, solvents evaporated and the residue purified by column chromatography to yield Acetic acid 2-[3-(7-fluoro-2,3-dihydro-benzo[b]thiophen-3-yl)thioureido]-ethyl ester (125 mg, 0.40 mmol, 54%).

C. Compound Examples

Some of the preferred compound examples are characterized by their physical data in the following table C. The characterized is done by coupled High Performance Liquid Chromatography/mass spectrometry (HPLC/MS) or by their melting points.

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

TABLE C

| Compound example | Structure of compound | melting point $F_p$ [° C.] | HPLC-MS ($t_r$ = retention time) |
|---|---|---|---|
| C.1 | | 128.0-130.0 | |
| C.2 | | 102.0-106.0 | |
| C.3 | | | $t_r$ = 2.90 min, m/z = 315 [M + 1] |
| C.4 | | 67-69 | |

TABLE C-continued

| Compound example | Structure of compound | melting point $F_p$ [° C.] | HPLC-MS ($t_r$ = retention time) |
|---|---|---|---|
| C.5 | | | $t_r$ = 3.27 min, m/z = 325 [M + 1] |
| C.6 | | 133-135 | |
| C.7 | | 125-127 | |
| C.8 | | | $t_r$ = 2.83 min, m/z = 269 [M + 1] |
| C.9 | | | $t_r$ = 3.49 min, m/z = 391 [M + 23] |

B. Biological Examples of Action Against Pests

The active compounds were formulated in a mixture of 50 vol.-% acetone:50 vol.-% water. A nonionic surfactant (Kinetic®) was included in the solution at a volume of 0.01% v/v.

In the following tests, the formulated solutions of the active compounds were diluted to an active ingredient concentration of 300 ppm, if not otherwise described, and the diluted solutions were applied in the below mentioned tests.

The action of the compounds of the formula I against pests was demonstrated by the following experiments:

B.1 Cotton Aphid (*Aphis gossypii*)

Cotton plants at the cotyledon stage were infested prior to treatment by placing a heavily infested leaf from the main aphid colony on top of each cotyledon. The aphids were allowed to transfer overnight and the host leaf was removed. The infested cotyledons were then dipped and agitated in the test solution for 3 seconds and allowed to dry in a fume hood. Test plants were maintained under fluorescent lighting in a 24-hr photoperiod at 25° C. and 20-40% relative humidity. Aphid mortality on the treated plants, relative to mortality on untreated check plants, was determined after 5 days.

In this test compound examples 1, 2, 5, 6, 7 and 8 at 300 ppm at least 75% mortality of cotton aphid (*Aphis gossypii*, mixed life stages) in comparison with untreated controls.

B.2 Green Peach Aphid (*Myzus persicae*)

Bell pepper plants at the first true-leaf stage were infested prior to treatment by placing heavily infested leaves from the main aphid colony on top of the treatment plants. The aphids were allowed to transfer overnight to accomplish an infestation of 30-40 aphids per plant and the host leaves were removed. The infested leaves of the test plants were then dipped and agitated in the test solution for 3 seconds and allowed to dry in a fume hood. Test plants were maintained under fluorescent lighting in a 24-hr photoperiod at 25° C. and 20-40% relative humidity. Mortality on the treated plants, relative to mortality on untreated check plants, was determined after 5 days.

In this test compound examples 1, 2, 3, 5, 6, 7 and 8 provided at 300 ppm at least 75% mortality of green peach aphid in comparison with untreated controls.

B.3 Cowpea Aphid (*aphis craccivora*)

The active compounds were formulated in 50:50 acetone: water. Potted cowpea plants colonized with 100-150 aphids of various stages were sprayed after the pest population has been recorded. Population reduction was recorded after 24, 72, and 120 hours.

In this test, compounds 1, 2, 3, 5, 6 and 8 at 300 ppm showed at least 75% mortality.

B.4 Silverleaf Whitefly (*bemisia argentifolii*)

The active compounds were formulated in 50:50 acetone: water and 100 ppm Kinetica™ surfactant.

Selected cotton plants were grown to the cotyledon state (one plant per pot). The cotyledons were dipped into the test solution to provide complete coverage of the foliage and placed in a well-vented area to dry. Each pot with treated seedling was placed in a plastic cup and 10 to 12 whitefly adults (approximately 3-5 day old) were introduced. The insects were colleted using an aspirator and an 0.6 cm, non-toxic TygonÒ tubing (R-3603) connected to a barrier pipette tip. The tip, containing the collected insects, was then gently inserted into the soil containing the treated plant, allowing insects to crawl out of the tip to reach the foliage for feeding. The cups were covered with a reusable screened lid (150 micron mesh polyester screen PeCap from Tetko Inc). Test plants were maintained in the holding room at about 25° C. and 20-40% relative humidity for 3 days avoiding direct exposure to the fluorescent light (24 hour photoperiod) to prevent trapping of heat inside the cup. Mortality was assessed 3 days after treatment of the plants.

In this test, compound 3, 5 and 7 at 300 ppm showed at least 75% mortality compared to untreated controls.

B.5 Vetch Aphid (*Megoura viciae*)

The active compounds were formulated in 1:3 DMSO: water. Bean leaf disks were placed into microtiterplates filled with 0.8% agar-agar and 2.5 ppm OPUS™. The leaf disks were sprayed with 2.5 μl of the test solution and 5 to 8 adult aphids were placed into the microtiterplates which were then closed and kept at 22-24° C. and 35-45% under fluorescent light for 6 days. Mortality was assessed on the basis of vital, reproduced aphids. Tests were replicated 2 times.

In this test, compounds 1, 2, 3, 5, 6, 7 and 8 at 2500 ppm showed at least 75% mortality compared to untreated controls.

The invention claimed is:
1. Substituted amino-thiourea compounds of formula I

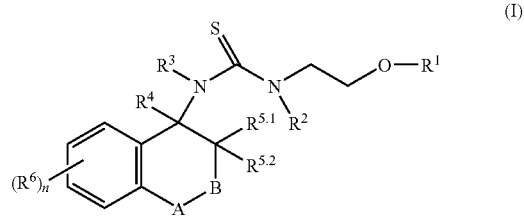

wherein
n is 0, 1, 2, 3 or 4;
A is $CR^{A.1}R^{A.2}$, oxygen, $NR^{A.3}$, sulfur, S(O) or $S(O)_2$,
  wherein
  $R^{A.1}$, $R^{A.2}$ are independently of each other selected from the group consisting of hydrogen, halogen, cyano, nitro, hydroxy, mercapto, amino, $C_1$-$C_6$-alkyl, $C_1$-$C_6$-haloalkyl, $C_1$-$C_6$-alkoxy, $C_1$-$C_6$-alkylamino, di-($C_1$-$C_6$-alkyl)amino, wherein the carbon atoms in the last 5 mentioned radicals may be unsubstituted or may carry any combination of 1, 2 or 3 radicals $R^a$;
  $C_3$-$C_8$-cycloalkyl, phenyl and benzyl, wherein each of the last three mentioned radicals may be unsubstituted or may carry any combination of 1, 2, 3, 4 or 5 radicals $R^b$; or
  $R^{A.1}$ together with $R^{A.2}$ may also be =O, =$NR^c$ or =$CR^d R^e$;
  $R^{A.3}$ is selected from the group consisting of hydrogen, formyl, CN, $C_1$-$C_6$-alkyl, $C_2$-$C_6$-alkenyl, $C_2$-$C_6$-alkynyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, ($C_1$-$C_6$-alkyl)thiocarbonyl, ($C_1$-$C_6$-alkoxy)thiocarbonyl, wherein the carbon atoms in the aliphatic radicals of the aforementioned groups may carry any combination of 1, 2 or 3 radicals $R^a$;
  $C(O)NR^f R^g$, $C(S)NR^f R^g$, $(SO_2)NR^f R^g$,
  phenyl, benzyl, phenoxycarbonyl, 5 or 6 membered hetarylmethyl, 5 or 6 membered hetarylcarbonyl and benzoyl, wherein each of the last six mentioned radicals may be unsubstituted or may carry any combination of 1, 2, 3, 4 or 5 radicals $R^b$, and wherein the 5 or 6 membered heteroaromatic ring in hetarylmethyl and hetarylcarbonyl contains 1, 2, 3 or 4 heteroatoms selected from the group consisting of oxygen, sulfur and nitrogen as ring members;

B is a chemical bond or $CH_2$;

$R^1$ is hydrogen, $C(=O)R^h$ or $C(=S)R^h$;

$R^2$, $R^3$ are selected independently from each other from the group consisting of hydrogen, cyano, nitro, formyl, $C(=O)R^i$, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkoxy)methylen, $C_1$-$C_6$-alkylsulfinyl, $C_1$-$C_6$-alkylsulfenyl and $C_1$-$C_6$-alkylsulfonyl, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, $C(O)NR^fR^g$, $(SO_2)NR^fR^g$, phenyl, phenyloxy and benzyl, each of the last three mentioned radicals may be unsubstituted or substituted with 1, 2, 3, 4 or 5 radicals $R^b$; or $R^2$ together with $R^1$ may be $C_1$-$C_3$-alkandiyl, $C_1$-$C_2$-alkandiylcarbonyl, $C_1$-$C_2$-alkandiylthiocarbonyl or a bridging $C=O$ or $C=S$ group;

$R^4$ is selected from the group consisting of hydrogen, formyl, cyano, $C_1$-$C_6$-alkyl, $C_2$-$C_6$-alkenyl, $C_2$-$C_6$-alkynyl, $C_1$-$C_6$-alkoxycarbonyl, $C_1$-$C_6$-alkylcarbonyl, $C_2$-$C_6$-alkenylcarbonyl, $C_2$-$C_6$-alkynylcarbonyl, wherein the carbon atoms in the last 5 mentioned radicals may be unsubstituted or may carry any combination of 1, 2 or 3 radicals $R^a$;

$C(O)NR^fR^g$, $C(S)NR^fR^g$, $C_3$-$C_8$-cycloalkyl, $C_3$-$C_8$-cycloalkenyl, aryl, arylmethyl, aryloxycarbonyl, arylcarbonyl, 5 or 6 membered hetaryl, 5 or 6 membered hetarylmethyl and 5 or 6 membered hetarylcarbonyl, wherein each of the six last mentioned radicals may be unsubstituted or may carry any combination of 1, 2, 3, 4 or 5 radicals $R^b$;

$R^{5.1}$, $R^{5.2}$ are independently from each other selected from the group consisting of hydrogen, halogen, hydroxy, nitro, cyano, carboxy, formyl, formyloxy, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_2$-$C_6$-alkenoxy, $C_2$-$C_6$-alkynoxy, $C_1$-$C_6$-haloalkoxy, $C_1$-$C_6$-alkylthio, $C_2$-$C_6$-alkenylthio, $C_2$-$C_6$-alkynylthio, $C_1$-$C_6$-haloalkylthio, wherein the carbon atoms in these groups may carry any combination of 1, 2 or 3 radicals $R^a$;

$C_3$-$C_8$-cycloalkyl, $C_3$-$C_8$-cycloalkenyl, phenyl, benzyl, 5 or 6 membered hetaryl and 5 or 6 membered hetarylmethyl, wherein each of the last mentioned cyclic radicals may be unsubstituted or may carry any combination of 1, 2, 3, 4 or 5 radicals $R^b$, and wherein the 5 or 6 membered heteroaromatic ring in hetarylmethyl and hetaryl contains 1, 2, 3 or 4 heteroatoms selected from the group consisting of oxygen, sulfur and nitrogen as ring members; or $R^{5.1}$ together with $R^{5.2}$ may also be $=O$, $=S$, $=NR^c$ or $=CR^dR^e$;

$R^6$ is selected from the group consisting of halogen, OH, SH, $NH_2$, $SO_3H$, COOH, cyano, azido, nitro, formyl, formyloxy, $CONH_2$, $CSNH_2$, $CH=N-OH$, $CH=N-O-(C_1-C_6)$-alkyl, $C(=O)R^j$, $C(=S)R^j$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, $C_1$-$C_6$-alkylamino, di($C_1$-$C_6$-alkyl)amino, $C_1$-$C_6$-alkylthio, $C_2$-$C_6$-alkenyloxy, $C_2$-$C_6$-alkenylamino, di($C_2$-$C_6$-alkenyl)amino, $C_2$-$C_6$-alkenylthio, $C_2$-$C_6$-alkynyl, $C_2$-$C_6$-alkynyloxy, $C_2$-$C_6$-alkynylamino, di($C_2$-$C_6$-alkynyl)amino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkenylsulfoxyl, $C_2$-$C_6$-alkynylsulfonyl, $C_2$-$C_6$-alkynylsulfoxyl, ($C_1$-$C_6$-alkoxy)carbonyl, ($C_2$-$C_6$-alkenyloxy)carbonyl, ($C_2$-$C_6$-alkynyloxy)carbonyl, ($C_1$-$C_6$-alkyl)carbonyloxy, ($C_2$-$C_6$-alkenyl-)carbonyl-oxy, ($C_2$-$C_6$-alkynyl)carbonyloxy, ($C_1$-$C_6$-alkyl)carbonyl-amino, ($C_2$-$C_6$-alkenyl)carbonyl-amino, ($C_2$-$C_6$-alkynyl)carbonyl-amino, wherein the carbon atoms in the aliphatic radicals of the aforementioned groups may carry any combination of 1, 2 or 3 radicals $R^a$;

$C(O)NR^fR^g$, $(SO_2)NR^fR^g$, a radical Y-Ar, a radical Y-Hc and a radical Y-Cy, wherein Y is a single bond, oxygen, sulfur, nitrogen, NH, $NR^f$, $C_1$-$C_6$-alkandiyl, $C_1$-$C_6$-alkandiyloxy, carbonyl or carbonyloxy group;

Ar is phenyl or naphthyl, wherein Ar is unsubstituted or may carry any combination of 1 to 5 radicals $R^b$;

Hc is a mono- or bicyclic 5- to 10-membered heteroaromatic ring, which contains 1, 2, 3 or 4 heteroatoms selected from 2 oxygen, 2 sulfur and 3 nitrogen atoms as ring members, wherein Hc is unsubstituted or may carry any combination of 1 to 5 radicals $R^b$;

Cy is $C_3$-$C_{12}$-cycloalkyl, which is unsubstituted or substituted with 1 to 5 radicals $R^b$;

and wherein the radical(s) $R^6$ that is/are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals $R^b$;

$R^a$ is selected from the group consisting of halogen, cyano, nitro, hydroxy, mercapto, amino, carboxyl, $C_3$-$C_6$-cycloalkyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylcarbonyl, $C_1$-$C_6$-alkoxycarbonyl, $C_1$-$C_6$-alkylthio, $C_1$-$C_6$-haloalkylthio, $C_1$-$C_6$-alkylsulfonyl and $C_1$-$C_6$-haloalkylsulfonyl;

$R^b$ is selected from the group consisting of halogen, cyano, nitro, hydroxy, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy, and $C_1$-$C_6$-alkylcarbonyloxy;

$R^c$ is selected from the group consisting of hydrogen, OH, $NH_2$, $C_1$-$C_6$-alkyl, $C_2$-$C_6$-alkenyl, $C_2$-$C_6$-alkynyl, $C_1$-$C_6$-alkoxy, $C_1$-$C_6$-alkylamino, di($C_1$-$C_6$-alkyl)amino, wherein the carbon atoms in these radicals may carry any combination of 1, 2 or 3 radicals $R^a$;

phenyl, benzyl, 5 or 6 membered hetaryl, phenylamino, N—($C_1$-$C_6$-alkyl)-N-phenyl-amino and diphenylamino, wherein aromatic group may be unsubstituted or may carry 1, 2 or 3 substituents $R^b$;

$R^d$, $R^e$ are independently of each other selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, di($C_1$-$C_6$-alkyl)amino, wherein the carbon atoms in these groups may carry any combination of 1, 2 or 3 radicals $R^a$;

phenyl, benzyl, and 5 or 6 membered hetaryl, wherein the aromatic group may be unsubstituted or may carry 1, 2 or 3 substituents $R^b$;

$R^f$, $R^g$ are independently of each other selected from the group consisting of hydrogen, hydroxy, amino, $C_1$-$C_6$- alkyl, $C_1$-$C_6$-haloalkyl, $C_2$-$C_6$-alkenyl, $C_2$-$C_6$-alkynyl, wherein the carbon atoms in these groups may carry any combination of 1, 2 or 3 radicals $R^a$;

phenyl, benzyl, and 5 or 6 membered hetaryl, wherein aromatic group may be unsubstituted or may carry 1, 2 or 3 substituents $R^b$;

$R^h$ is selected from the group consisting of hydrogen, $C_1$-$C_6$-alkyl, $C_2$-$C_6$-alkenyl, $C_2$-$C_6$-alkynyl, $C_1$-$C_6$-alkylamino, di($C_1$-$C_6$-alkyl)amino, $C_2$-$C_6$-alkandiylamino, $C_2$-$C_6$-alkenylamino, di($C_2$-$C_6$-alkenyl)amino, $C_2$-$C_6$-alkynylamino, di($C_2$-$C_6$-alkynyl)amino, $C_1$-$C_6$-alkoxy, $C_2$-$C_6$-alkenyloxy, $C_2$-$C_6$-alkynyloxy, $C_1$-$C_6$-alkylthio, $C_3$-$C_{12}$-cycloalkylthio, $C_2$-$C_6$-alkenylthio, $C_2$-$C_6$-alkynylthio, wherein the carbon atoms in these groups may be substituted with 1, 2, 3, 4 or 5 radicals $R^a$; a radical Y-Ar, a radical Y-Cy and a radical Y-Hc, and wherein Y is a single bond, oxygen, sulfur, nitrogen, NH, $NR^f$, $C_1$-$C_6$-alkandiyloxy, carbonyl or carbonyloxy, wherein the aliphatic carbon atoms in these groups may be unsubstituted or substituted with $R^a$;

Ar is phenyl or naphthyl, wherein Ar is unsubstituted or may carry any combination of 1 to 5 radicals $R^b$ Cy is $C_3$-$C_{12}$-cycloalkyl, which is unsubstituted or substituted with 1 to 5 radicals $R^b$;

Hc is saturated or partially unsaturated 3 to 8 membered heterocycle, which contains 1, 2, 3 or 4 heteroatoms selected from the group consisting of oxygen, sulfur and nitrogen atoms and/or 1 or 2 heteroaromatic groups selected from the group consisting of S(O) and $S(O)_2$ as ring members, and wherein the ring is unsubstituted or may carry 1, 2, 3 or 4 radicals $R^b$;

$R^i$ are each independently selected from the group consisting of hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from the group consisting of O, S and N;

$R^j$ is selected from the group consisting of hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, hydrazino, ($C_1$-$C_6$-alkyl)hydrazino, di($C_1$-$C_6$-alkyl)hydrazino, phenyl and heteroaryl, which can be a mono- or bicyclic 5 to 10 membered heteroaromatic ring, which contains 1, 2, 3 or 4 heteroatoms selected from the group consisting of O, S and N;

or the enantiomers, diastereomers or salts thereof;
with the provisos that i) if B is $CH_2$ and A is $CH_2$, then $R^1$ is different from hydrogen, and ii) if B is $CH_2$ and A is $C(R^{4.1})(R^{4.2})$ and $R^1$ is hydrogen, then at least one of $R^{4.1}$ and $R^{4.2}$ is different than hydrogen, and iii) if A is $C(R^{4.1})(R^{4.2})$, then at least one of $R^4$, $R^{5.1}$, $R^{5.2}$, $R^{4.1}$ or $R^{4.2}$ is different than hydrogen.

2. Substituted amino-thiourea compounds of formula (I) as claimed in claim 1 wherein $R^1$ is hydrogen or $C(=O)R^h$.

3. Substituted amino-thiourea compounds of formula (I) as claimed in claim 2, wherein $R^1$ is hydrogen.

4. Substituted amino-thiourea compounds of formula (I) as claimed in claim 2, wherein $R^1$ is $C(=O)R^h$.

5. Substituted amino-thiourea compounds of formula (I) as claimed in claim 1, wherein $R^1$ is $C(=S)R^h$.

6. Substituted amino-thiourea compounds of formula (I) as claimed in claim 1, wherein $R^1$ is $C(=O)R^h$ and $R^h$ is $C_1$-$C_6$-alkyl, and wherein the $C_1$-$C_6$-alkyl may be unsubstituted or substituted with 1, 2, 3, 4 or 5 radicals $R^a$.

7. Substituted amino-thiourea compounds of formula (I) as claimed in claim 1, wherein $R^1$ is $C(=O)R^h$ and $R^h$ is a radical Y-Ar or Y-Hc, and wherein Y is a single bond, oxygen or nitrogen, NH or $NR^f$, and Ar is phenyl or naphthyl;

Hc is pyrimidyl, pyridyl, thienyl, furyl, pyrazolyl, imidazolyl, triazolyl, thiazolyl, oxazolyl, isothiazolyl, isoxazolyl, quinolinyl, isoquinolinyl, indolyl, benzofuryl, benzthienyl, benzoxazolyl, benzthiazolyl or benzimidazolyl, and wherein the Ar or the Hc may be unsubstituted or may carry any combination of 1 to 5 radicals $R^b$.

8. Substituted amino-thiourea compounds of formula (I) as claimed in claim 1, wherein $R^1$ is $C(=O)R^h$ and $R^h$ is a radical Y-Hc, and wherein Y is a single bond, oxygen or nitrogen, NH or $NR^f$, and Hc is selected from the group consisting of pyridyl, thienyl, furyl, pyrazolyl, imidazolyl, thiazolyl, oxazolyl, quinolinyl, benzofuryl, benzthienyl, benzoxazolyl and benzthiazolyl, and wherein the heterocyclic radicals may be unsubstituted or may carry any combination of 1, 2, 3, 4 or 5 radicals $R^b$.

9. Substituted amino-thiourea compounds of formula (I) as claimed in claim 1, wherein A is oxygen, $NR^{4.3}$, sulfur, S(O) or $S(O)_2$.

10. Substituted amino-thiourea compounds of formula (I) as claimed in claim 1, wherein A is $CR^{4.1}R^{4.2}$ and $R^{4.1}$ and $R^{4.2}$ are independently from one another hydrogen or $C_1$-$C_6$-alkyl.

11. Substituted amino-thiourea compounds of formula (I) as claimed in claim 1, wherein A is $CH_2$.

12. Substituted amino-thiourea compounds of formula (I) as claimed in claim 1, wherein A is $NR^{4.3}$ and $R^{4.3}$ is hydrogen, $C_1$-$C_6$-alkyl or $C_1$-$C_6$-alkylcarbonyl.

13. Substituted amino-thiourea compounds of formula (I) as claimed in claim 1, wherein the phenyl ring carries 1 or 2 radicals $R^6$, which are independently of each other selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio and $C_1$-$C_6$-haloalkylthio.

14. Substituted amino-thiourea compounds of formula (I) as claimed in claim 1, wherein the phenyl ring carries 1 or 2 radicals $R^6$, which are independently of each other selected from the group consisting of halogen, $C_1$-$C_6$-alkyl and $C_1$-$C_6$-haloalkyl.

15. Substituted amino-thiourea compounds of formula (I) as claimed in claim 1, wherein $R^{5.1}$ and $R^{5.2}$ are selected independently from one another from the group consisting of hydrogen, $C_1$-$C_6$-alkyl, $C_1$-$C_6$-alkenyl, $C_1$-$C_6$-alkynyl, $C_1$-$C_6$-haloalkyl, $C_1$-$C_6$-haloalkenyl, $C_1$-$C_6$-haloalkynyl, wherein the aliphatic carbon radicals may be unsubstituted or substituted with 1, 2, 3, 4 or 5 radicals $R^a$;

phenyl, benzyl, pyrimidyl, pyridyl, thienyl, furyl, pyrazolyl, imidazolyl, triazolyl, thiazolyl, oxazolyl, isothiazolyl, isoxazolyl, quinolinyl, isoquinolinyl, indolyl, benzofuryl, benzthienyl, benzoxazolyl, benzthiazolyl and benzimidazolyl, and wherein the cyclic radicals may be unsubstituted or may carry any combination of 1, 2, 3, 4 or 5 radicals $R^b$.

16. Substituted amino-thiourea compounds of formula (I) as claimed in claim 1, wherein $R^{5.1}$ or $R^{5.2}$ are independently from one another hydrogen or $C_1$-$C_6$-alkyl, and wherein the $C_1$-$C_6$-alkyl may be unsubstituted or substituted with 1, 2, 3, 4 or 5 radicals $R^a$.

17. Substituted amino-thiourea compounds of formula (I) as claimed in claim 1, wherein $R^{5.1}$ and/or $R^{5.2}$ is phenyl, and wherein the phenyl may be unsubstituted or may carry any combination of 1, 2, 3, 4 or 5 radicals $R^b$.

18. Substituted amino-thiourea compounds of formula (I) as claimed in claim 1, wherein $R^{5.1}$ and/or $R^{5.2}$ is selected from the group consisting of pyridyl, thienyl, furyl, pyrazolyl, imidazolyl, thiazolyl, oxazolyl, quinolinyl, benzofuryl, benzthienyl, benzoxazolyl and benzthiazolyl, wherein the heterocyclic radicals may be unsubstituted or may carry any combination of 1, 2, 3, 4 or 5 radicals $R^b$.

19. Substituted amino-thiourea compounds of formula (I) as claimed in claim 1, wherein $R^2$ and $R^3$ are selected independently from one another from the group consisting of hydrogen, $C(=O)R^i$ and $C_1$-$C_6$-alkyl.

20. Substituted amino-thiourea compounds of formula (I) as claimed in claim 1, wherein $R^2$ and $R^3$ are both hydrogen.

21. Substituted amino-thiourea compounds of formula (I) as claimed in claim 1, wherein $R^4$ is selected from the group consisting of hydrogen, $C_1$-$C_6$-alkyl, $C_2$-$C_6$-alkenyl, optionally substituted phenyl and optionally substituted benzyl.

22. Substituted amino-thiourea compounds of formula (I) as claimed in claim 1, wherein $R^4$ is hydrogen.

23. Substituted amino-thiourea compounds of formula (I) as claimed in claim 1, wherein B is a single bond.

24. Substituted amino-thiourea compounds of formula (I) as claimed in claim 1, wherein B is $CH_2$.

25. Substituted amino-thiourea compounds of formula (I) as claimed in claim 1, wherein n is 0.

26. Substituted amino-thiourea compounds of formula (I) as claimed in claim 1, wherein n is 1 or 2.

27. Substituted amino-thiourea compounds of formula (I) as claimed in claim 1, wherein
n is 1 or 2
A is oxygen or sulfur
B is a chemical bond
$R^1$ is hydrogen or $C(=O)R^h$
$R^2$, $R^3$ are both hydrogen and
$R^6$ is halogen or $C_1$-$C_6$-alkyl.

28. A composition comprising at least one amino-thiourea compound of the formula I according to claim 1, or the enantiomer, diastereomer or salt thereof and at least one inert liquid and/or solid carrier.

29. An agricultural composition comprising a pesticidally effective amount of at least one amino-thiourea compound of the formula I according to claim 1 or the enantiomer, diastereomer or agriculturally useful salt thereof, and at least one inert liquid and/or solid agriculturally acceptable carrier and, if desired, at least one surfactant.

30. A method for combating or controlling insects, arachnids or nematodes or for protecting growing plants from attack or infestation by insects, arachnids or nematodes comprising contacting an insect, arachnid or nematode or their food supply, habitat or breeding grounds or contacting a plant, or soil or water in which the plant is growing with a pesticidally effective amount of at least one amino-thiourea compound of the formula I

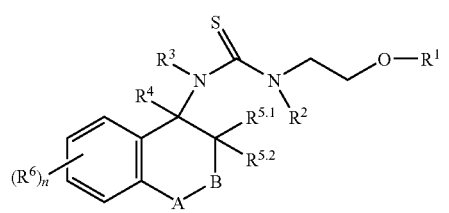

(I)

wherein
n is 0, 1, 2, 3 or 4.
A is $CR^{A.1}R^{A.2}$, oxygen, $NR^{A.3}$, sulfur, $S(O)$ or $S(O)_2$, wherein $R^{A.1}$, $R^{A.2}$ are independently of each other selected from the group consisting of hydrogen, halogen, cyano, nitro, hydroxy, mercapto, amino, $C_1$-$C_6$-alkyl, $C_1$-$C_6$-haloalkyl, $C_1$-$C_6$-alkoxy, $C_1$-$C_6$-alkylamino, di-($C_1$-$C_6$-alkyl)amino, wherein the carbon atoms in the last 5 mentioned radicals may be unsubstituted or may carry any combination of 1, 2 or 3 radicals $R^a$,
$C_3$-$C_8$-cycloalkyl, phenyl and benzyl, wherein each of the last three mentioned radicals may be unsubstituted or may carry any combination of 1, 2, 3, 4 or 5 radicals $R^b$; or
$R^{A.1}$ together with $R^{A.2}$ may also be $=O$, $=NR^c$ or $=CR^dR^e$;
$R^{A.3}$ is selected from the group consisting of hydrogen, formyl, CN, $C_1$-$C_6$-alkyl, $C_2$-$C_6$-alkenyl, $C_2$-$C_6$-alkynyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, ($C_1$-$C_6$-alkyl)thiocarbonyl, ($C_1$-$C_6$-alkoxy)thiocarbonyl, wherein the carbon atoms in the aliphatic radicals of the aforementioned groups may carry any combination of 1, 2 or 3 radicals $R^a$;
$C(O)NR^fR^g$, $C(S)NR^fR^g$, $(SO_2)NR^fR^g$,
phenyl, benzyl, phenoxycarbonyl, 5 or 6 membered hetarylcarbonyl, 5 or 6 membered hetarylmethyl and benzoyl, wherein each of the last six mentioned radicals may be unsubstituted or may carry any combination of 1, 2, 3, 4 or 5 radicals $R^b$, and wherein the 5 or 6 membered heteroaromatic ring in hetarylmethyl and hetarylcarbonyl contains 1, 2, 3 or 4 heteroatoms selected from the group consisting of oxygen, sulfur and nitrogen as ring members;
B is a chemical bond or $CH_2$;
$R^1$ is hydrogen, $C(=O)R^h$ or $C(=S)R^h$;
$R^2$, $R^3$ are selected independently from each other from the group consisting of hydrogen, cyano, nitro, formyl, $C(=O)R^i$, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkoxy)methylen, $C_1$-$C_6$-alkylsulfinyl, $C_1$-$C_6$-alkylsulfenyl and $C_1$-$C_6$-alkylsulfonyl, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C(O)NR^fR^g$, $(SO_2)NR^fR^g$, phenyl, phenyloxy and benzyl, each of the last three mentioned radicals may be unsubstituted or substituted with 1, 2, 3, 4 or 5 radicals $R^b$; or
$R^2$ together with $R^1$ may be $C_1$-$C_3$-alkandiyl, $C_1$-$C_2$-alkandiylcarbonyl, $C_1$-$C_2$-alkandiylthiocarbonyl or a bridging $C=O$ or $C=S$ group;
$R^4$ is selected from the group consisting of hydrogen, formyl, cyano, $C_1$-$C_6$-alkyl, $C_1$-$C_6$-haloalkyl, $C_2$-$C_6$-alkenyl, $C_2$-$C_6$-alkynyl, $C_1$-$C_6$-alkoxycarbonyl, $C_1$-$C_6$-alkylcarbonyl, $C_2$-$C_6$-alkenylcarbonyl, $C_2$-$C_6$-alkynylcarbonyl, wherein the carbon atoms in the last 5 mentioned radicals may be unsubstituted or may carry any combination of 1, 2 or 3 radicals $R^a$;
$C(O)NR^fR^g$, $C(S)NR^fR^g$,
$C_3$-$C_8$-cycloalkyl, $C_3$-$C_8$-cycloalkenyl, aryl, arylmethyl, aryloxycarbonyl, arylcarbonyl, 5 or 6 membered hetaryl, 5 or 6 membered hetarylmethyl and 5 or 6 membered hetarylcarbonyl, wherein each of the six last mentioned radicals may be unsubstituted or may carry any combination of 1, 2, 3, 4 or 5 radicals $R^b$;

$R^{5.1}$, $R^{5.2}$ are independently from each other selected from the group consisting of hydrogen, halogen, hydroxy, nitro, cyano, carboxy, formyl, formyloxy, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_2$-$C_6$-alkenoxy, $C_2$-$C_6$-alkynoxy, $C_1$-$C_6$-haloalkoxy, $C_1$-$C_6$-alkylthio, $C_2$-$C_6$-alkenylthio, $C_2$-$C_6$-alkynylthio, $C_1$-$C_6$-haloalkylthio, wherein the carbon atoms in these groups may carry any combination of 1, 2 or 3 radicals $R^a$;

$C_3$-$C_8$-cycloalkyl, $C_3$-$C_8$-cycloalkenyl, phenyl, benzyl, 5 or 6 membered hetaryl and 5 or 6 membered hetarylmethyl, wherein each of the last mentioned cyclic radicals may be unsubstituted or may carry any combination of 1, 2, 3, 4 or 5 radicals $R^b$, and wherein the 5 or 6 membered heteroaromatic ring in hetarylmethyl and hetaryl contains 1, 2, 3 or 4 heteroatoms selected from the group consisting of oxygen, sulfur and nitrogen as ring members; or $R^{5.1}$ together with $R^{5.2}$ may also be =O, =S, =$NR^c$ or =$CR^dR^e$;

$R^6$ is selected from the group consisting of halogen, OH, SH, $NH_2$, $SO_3H$, COOH, cyano, azido, nitro, formyl, formyloxy, $CONH_2$, $CSNH_2$, CH=N—OH, CH=N—O—($C_1$-$C_6$)-alkyl, C(=O)$R^j$, C(=S)$R^j$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, $C_1$-$C_6$-alkylamino, di($C_1$-$C_6$-alkyl)amino, $C_1$-$C_6$-alkylthio, $C_2$-$C_6$-alkenyloxy, $C_2$-$C_6$-alkenylamino, di($C_1$-$C_6$-alkenyl)amino, $C_2$-$C_6$-alkenylthio, $C_2$-$C_6$-alkynyl, $C_2$-$C_6$-alkynyloxy, $C_2$-$C_6$-alkynylamino, di($C_1$-$C_6$-alkynyl)amino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkenylsulfoxyl, $C_2$-$C_6$-alkynylsulfonyl, $C_2$-$C_6$-alkynylsulfoxyl, ($C_1$-$C_6$-alkoxy)carbonyl, ($C_2$-$C_6$-alkenyloxy)carbonyl, ($C_2$-$C_6$-alkynyloxy)carbonyl, ($C_1$-$C_6$-alkyl)carbonyloxy, ($C_2$-$C_6$-alkenyl-)carbonyl-oxy, ($C_2$-$C_6$-alkynyl)carbonyloxy, ($C_1$-$C_6$-alkyl)carbonyl-amino, ($C_2$-$C_6$-alkenyl)carbonyl-amino, ($C_2$-$C_6$-alkynyl)carbonyl-amino, wherein the carbon atoms in the aliphatic radicals of the aforementioned groups may carry any combination of 1, 2 or 3 radicals $R^a$;

C(O)$NR^fR^g$, ($SO_2$)$NR^fR^g$, a radical Y-Ar, a radical Y-Hc and a radical Y-Cy, wherein Y is a single bond, oxygen, sulfur, nitrogen, NH, $NR^f$, $C_1$-$C_6$-alkandiyl, $C_1$-$C_6$-alkandiyloxy, carbonyl or carbonyloxy group;

Ar is phenyl or naphthyl, wherein Ar is unsubstituted or may carry any combination of 1 to 5 radicals $R^b$;

Hc is a mono- or bicyclic 5- to 10-membered heteroaromatic ring, which contains 1, 2, 3 or 4 heteroatoms selected from 2 oxygen, 2 sulfur and 3 nitrogen atoms as ring members, wherein Hc is unsubstituted or may carry any combination of 1 to 5 radicals $R^b$;

Cy is $C_3$-$C_{12}$-cycloalkyl, which is unsubstituted or substituted with 1 to 5 radicals $R^b$;

and wherein the radical(s) $R^6$ that is/are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals $R^b$;

$R^a$ is selected from the group consisting of halogen, cyano, nitro, hydroxy, mercapto, amino, carboxyl, $C_3$-$C_6$-cycloalkyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylcarbonyl, $C_1$-$C_6$-alkoxycarbonyl, $C_1$-$C_6$-alkylthio, $C_1$-$C_6$-haloalkylthio, $C_1$-$C_6$-alkylsulfonyl and $C_1$-$C_6$-haloalkylsulfonyl;

$R^b$ is selected from the group consisting of halogen, cyano, nitro, hydroxy, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy, and $C_1$-$C_6$-alkylcarbonyloxy;

$R^c$ is selected from the group consisting of hydrogen, OH, $NH_2$, $C_1$-$C_6$-alkyl, $C_2$-$C_6$-alkenyl, $C_2$-$C_6$-alkynyl, $C_1$-$C_6$-alkoxy, $C_1$-$C_6$-alkylamino, di($C_1$-$C_6$-alkyl)amino, wherein the carbon atoms in these radicals may carry any combination of 1, 2 or 3 radicals $R^a$;

phenyl, benzyl, 5 or 6 membered hetaryl, phenylamino, N—($C_1$-$C_6$-alkyl)-N-phenyl-amino and diphenylamino, wherein aromatic group may be unsubstituted or may carry 1, 2 or 3 substituents $R^b$;

$R^d$, $R^e$ are independently of each other selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, di($C_1$-$C_6$-alkyl)amino, wherein the carbon atoms in these groups may carry any combination of 1, 2 or 3 radicals $R^a$;

phenyl, benzyl, and 5 or 6 membered hetaryl, wherein the aromatic group may be unsubstituted or may carry 1, 2 or 3 substituents $R^b$;

$R^f$, $R^g$ are independently of each other selected from the group consisting of hydrogen, hydroxy, amino, $C_1$-$C_6$-alkyl, $C_1$-$C_6$-haloalkyl, $C_2$-$C_6$-alkenyl, $C_2$-$C_6$-alkynyl, wherein the carbon atoms in these groups may carry any combination of 1, 2 or 3 radicals $R^a$;

phenyl, benzyl, and 5 or 6 membered hetaryl, wherein aromatic group may be unsubstituted or may carry 1, 2 or 3 substituents $R^b$;

$R^h$ is selected from the group consisting of hydrogen, $C_1$-$C_6$-alkyl, $C_2$-$C_6$-alkenyl, $C_2$-$C_6$-alkynyl, $C_1$-$C_6$-alkylamino, di($C_1$-$C_6$-alkyl)amino, $C_2$-$C_6$-alkandiylamino, $C_2$-$C_6$-alkenylamino, di($C_2$-$C_6$-alkenyl)amino, $C_2$-$C_6$-alkynylamino, di($C_2$-$C_6$-alkynyl)amino, $C_1$-$C_6$-alkoxy, $C_2$-$C_6$-alkenyloxy, $C_2$-$C_6$-alkynyloxy, $C_1$-$C_6$-alkylthio, $C_3$-$C_{12}$-cycloalkylthio, $C_2$-$C_6$-alkenylthio, $C_2$-$C_6$-alkynylthio, wherein the carbon atoms in these groups may be substituted with 1, 2, 3, 4 or 5 radicals $R^a$;

a radical Y-Ar, a radical Y-Cy and a radical Y-Hc, and wherein

Y is a single bond, oxygen, sulfur, nitrogen, NH, $NR^f$, $C_1$-$C_6$-alkandiyl, $C_1$-$C_6$-alkandiyloxy, carbonyl or carbonyloxy, wherein the aliphatic carbon atoms in these groups may be unsubstituted or substituted with $R^a$;

Ar is phenyl or naphthyl, wherein Ar is unsubstituted or may carry any combination of 1 to 5 radicals $R^h$ Cy is $C_3$-$C_{12}$-cycloalkyl, which is unsubstituted or substituted with 1 to 5 radicals $R^b$;

Hc is saturated or partially unsaturated 3 to 8 membered heterocycle, which contains 1, 2, 3 or 4 heteroatoms selected from the group consisting of oxygen, sulfur and nitrogen atoms and/or 1 or 2 heteroaromatic groups selected from the group consisting of S(O) and $S(O)_2$ as ring members, and wherein the ring is unsubstituted or may carry 1, 2, 3 or 4 radicals $R^b$;

R$^i$ are each independently selected from the group consisting of hydrogen, C$_1$-C$_6$-alkyl, C$_2$-C$_6$-alkenyl, C$_2$-C$_6$-alkinyl, C$_3$-C$_8$-cycloalkyl, C$_1$-C$_6$-alkylthio, C$_1$-C$_6$-alkoxy, (C$_1$-C$_6$-alkyl)amino, di(C$_1$-C$_6$-alkyl)amino, phenyl and heteroaryl, which can be a mono- or bicyclic 5 to 10 membered heteroaromatic ring, which contains 1, 2, 3 or 4 heteroatoms selected from the group consisting of O, S and N;

R$^j$ is selected from the group consisting of hydrogen, C$_1$-C$_6$-alkyl, C$_2$-C$_6$-alkenyl, C$_2$-C$_6$-alkinyl, C$_3$-C$_8$-cycloalkyl, C$_1$-C$_6$-alkoxy, (C$_1$-C$_6$-alkyl)amino, di(C$_1$-C$_6$-alkyl)amino, hydrazino, (C$_1$-C$_6$-alkyl)hydrazino, di(C$_1$-C$_6$-alkyl)hydrazino, phenyl and heteroaryl, which can be a mono- or bicyclic 5 to 10 membered heteroaromatic ring, which contains 1, 2, 3 or 4 heteroatoms selected from the group consisting of O, S and N;

or the enantiomers, diastereomers or salts thereof;

with the provisos that if A is C(R$^{A.1}$)(R$^{A.2}$), then at least one of R$^4$, R$^{5.1}$, R$^{5.2}$, R$^{A.1}$ or R$^{A.2}$ is different than hydrogen.

31. The method as defined in claim 30, wherein the animal pest is from the order Hemiptera or Thysanoptera.

32. A method for the protection of seeds from soil insects and of the seedlings' roots and shoots from soil and foliar insects comprising contacting the seeds before sowing and/or after pregermination with at least one amino-thiourea compound of the formula I

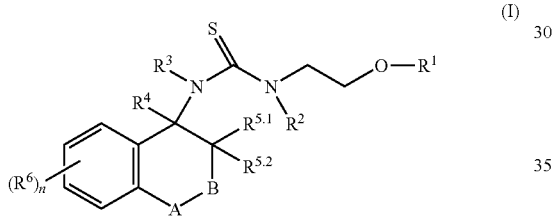

(I)

wherein n is 0, 1, 2, 3 or 4;

A is CR$^{A.1}$R$^{A.2}$, oxygen, NR$^{A.3}$, sulfur, S(O) or S(O)$_2$, wherein

R$^{A.1}$, R$^{A.2}$ are independently of each other selected from the group consisting of hydrogen, halogen, cyano, nitro, hydroxy, mercapto, amino, C$_1$-C$_6$-alkyl, C$_1$-C$_6$-haloalkyl, C$_1$-C$_6$-alkoxy, C$_1$-C$_6$-alkylamino, di-(C$_1$-C$_6$-alkyl)amino, wherein the carbon atoms in the last 5 mentioned radicals may be unsubstituted or may carry any combination of 1, 2 or 3 radicals R$^a$, C$_3$-C$_8$-cycloalkyl, phenyl and benzyl, wherein each of the last three mentioned radicals may be unsubstituted or may carry any combination of 1, 2, 3, 4 or 5 radicals R$^b$; or R$^{A.1}$ together with R$^{A.2}$ may also be =O, =NR$^c$ or =CR$^d$R$^e$;

R$^{A.3}$ is selected from the group consisting of hydrogen, formyl, CN, C$_1$-C$_6$-alkyl, C$_2$-C$_6$-alkenyl, C$_2$-C$_6$-alkynyl, C$_1$-C$_6$-alkylcarbonyl, C$_2$-C$_6$-alkenylcarbonyl, C$_2$-C$_6$-alkynylcarbonyl, C$_1$-C$_6$-alkoxycarbonyl, (C$_1$-C$_6$-alkyl)thiocarbonyl, (C$_1$-C$_6$-alkoxy)thiocarbonyl, wherein the carbon atoms in the aliphatic radicals of the aforementioned groups may carry any combination of 1, 2 or 3 radicals R$^a$;

C(O)NR$^f$R$^g$, C(S)NR$^f$R$^g$, (SO$_2$)NR$^f$R$^g$, phenyl, benzyl, phenoxycarbonyl, 5 or 6 membered hetarylmethyl, 5 or 6 membered hetarylcarbonyl and benzoyl, wherein each of the last six mentioned radicals may be unsubstituted or may carry any combination of 1, 2, 3, 4 or 5 radicals R$^b$, and wherein the 5 or 6 membered heteroaromatic ring in hetarylmethyl and hetarylcarbonyl contains 1, 2, 3 or 4 heteroatoms selected from the group consisting of oxygen, sulfur and nitrogen as ring members;

B is a chemical bond or CH$_2$;

R$^1$ is hydrogen, C(=O)R$^h$ or C(=S)R$^h$;

R$^2$, R$^3$ are selected independently from each other from the group consisting of hydrogen, cyano, nitro, formyl, C(=O)R$^1$, C$_1$-C$_6$-alkyl, C$_2$-C$_6$-alkenyl, C$_2$-C$_6$-alkynyl, C$_3$-C$_8$-cycloalkyl, C$_1$-C$_6$-alkoxy, (C$_1$-C$_6$-alkoxy)methylen, C$_1$-C$_6$-alkylsulfinyl, C$_1$-C$_6$-alkylsulfenyl and C$_1$-C$_6$-alkylsulfonyl, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, C$_1$-C$_6$-alkyl, C$_1$-C$_6$-alkoxy, C$_2$-C$_6$-alkenyloxy, C$_2$-C$_6$-alkynyloxy, C$_1$-C$_6$-haloalkoxy, C$_1$-C$_6$-alkylthio, C(O)NR$^f$R$^g$, (SO$_2$)NR$^f$R$^g$, phenyl, phenyloxy and benzyl, each of the last three mentioned radicals may be unsubstituted or substituted with 1, 2, 3, 4 or 5 radicals R$^b$; or R$^2$ together with R$^1$ may be C$_1$-C$_3$-alkandiyl, C$_1$-C$_2$-alkandiylcarbonyl, C$_1$-C$_2$-alkandiylthiocarbonyl or a bridging C=O or C=S group;

R$^4$ is selected from the group consisting of hydrogen, formyl, cyano, C$_1$-C$_6$-alkyl, C$_1$-C$_6$-haloalkyl, C$_2$-C$_6$-alkenyl, C$_2$-C$_6$-alkynyl, C$_1$-C$_6$-alkoxycarbonyl, C$_1$-C$_6$-alkylcarbonyl, C$_2$-C$_6$-alkenylcarbonyl, C$_2$-C$_6$-alkynylcarbonyl, wherein the carbon atoms in the last 5 mentioned radicals may be unsubstituted or may carry any combination of 1, 2 or 3 radicals R$^a$;

C(O)NR$^f$R$^g$, C(S)NR$^f$R$^g$,

C$_3$-C$_8$-cycloalkyl, C$_3$-C$_8$-cycloalkenyl, aryl, arylmethyl, aryloxycarbonyl, arylcarbonyl, 5 or 6 membered hetaryl, 5 or 6 membered hetarylmethyl and 5 or 6 membered hetarylcarbonyl, wherein each of the six last mentioned radicals may be unsubstituted or may carry any combination of 1, 2, 3, 4 or 5 radicals R$^b$;

R$^{5.1}$, R$^{5.2}$ are independently from each other selected from the group consisting of hydrogen, halogen, hydroxy, nitro, cyano, carboxy, formyl, formyloxy, C$_1$-C$_6$-alkyl, C$_2$-C$_6$-alkenyl, C$_2$-C$_6$-alkynyl, C$_1$-C$_6$-haloalkyl, C$_1$-C$_6$-alkoxy, C$_2$-C$_6$-alkenoxy, C$_2$-C$_6$-alkynoxy, C$_1$-C$_6$-haloalkoxy, C$_1$-C$_6$-alkylthio, C$_2$-C$_6$-alkenylthio, C$_2$-C$_6$-alkynylthio, C$_1$-C$_6$-haloalkylthio, wherein the carbon atoms in these groups may carry any combination of 1, 2 or 3 radicals R$^a$;

C$_3$-C$_8$-cycloalkyl, C$_3$-C$_8$-cycloalkenyl, phenyl, benzyl, 5 or 6 membered hetaryl and 5 or 6 membered hetarylmethyl, wherein each of the last mentioned cyclic radicals may be unsubstituted or may carry any combination of 1, 2, 3, 4 or 5 radicals R$^b$, and wherein the 5 or 6 membered heteroaromatic ring in hetarylmethyl and hetaryl contains 1, 2, 3 or 4 heteroatoms selected from the group consisting of oxygen, sulfur and nitrogen as ring members; or R$^{5.1}$ together with R$^{5.2}$ may also be =O, =S, =NR$^c$ or =CR$^d$R$^e$;

R$^6$ is selected from the group consisting of halogen, OH, SH, NH$_2$, SO$_3$H, COOH, cyano, azido, nitro, formyl, formyloxy, CONH$_2$, CSNH$_2$, CH=N—OH, CH=N—O—(C$_1$-C$_6$)-alkyl, C(=O)R$^j$, C(=S)R$^j$, C$_1$-C$_6$-alkyl, C$_2$-C$_6$-alkenyl, C$_2$-C$_6$-alkinyl, C$_3$-C$_8$-cycloalkyl, C$_1$-C$_6$-alkoxy, C$_1$-C$_6$-alkylamino, di(C$_1$-C$_6$-alkyl)

amino, $C_1$-$C_6$-alkylthio, $C_2$-$C_6$-alkenyloxy, $C_2$-$C_6$-alkenylamino, di($C_1$-$C_6$-alkenyl)amino, $C_2$-$C_6$-alkenylthio, $C_2$-$C_6$-alkynyl, $C_2$-$C_6$-alkynyloxy, $C_2$-$C_6$-alkynylamino, di($C_1$-$C_6$-alkynyl)amino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkenylsulfoxyl, $C_2$-$C_6$-alkynylsulfonyl, $C_2$-$C_6$-alkynylsulfoxyl, ($C_1$-$C_6$-alkoxy)carbonyl, ($C_2$-$C_6$-alkenyloxy)carbonyl, ($C_2$-$C_6$-alkynyloxy)carbonyl, ($C_1$-$C_6$-alkyl)carbonyloxy, ($C_2$-$C_6$-alkenyl-)carbonyl-oxy, ($C_2$-$C_6$-alkynyl)carbonyloxy, ($C_1$-$C_6$-alkyl)carbonyl-amino, ($C_2$-$C_6$-alkenyl)carbonyl-amino, ($C_2$-$C_6$-alkynyl)carbonyl-amino, wherein the carbon atoms in the aliphatic radicals of the aforementioned groups may carry any combination of 1, 2 or 3 radicals $R^a$;

$C(O)NR^fR^g$, $(SO_2)NR^fR^g$, a radical Y-Ar, a radical Y-Hc and a radical Y-Cy, wherein Y is a single bond, oxygen, sulfur, nitrogen, NH, $NR^f$, $C_1$-$C_6$-alkandiyl, $C_1$-$C_6$-alkandiyloxy, carbonyl or carbonyloxy group;

Ar is phenyl or naphthyl, wherein Ar is unsubstituted or may carry any combination of 1 to 5 radicals $R^b$;

Hc is a mono- or bicyclic 5- to 10-membered heteroaromatic ring, which contains 1, 2, 3 or 4 heteroatoms selected from 2 oxygen, 2 sulfur and 3 nitrogen atoms as ring members, wherein Hc is unsubstituted or may carry any combination of 1 to 5 radicals $R^b$;

Cy is $C_3$-$C_{12}$-cycloalkyl, which is unsubstituted or substituted with 1 to 5 radicals $R^b$;

and wherein the radical(s) $R^6$ that is/are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals $R^b$;

$R^a$ is selected from the group consisting of halogen, cyano, nitro, hydroxy, mercapto, amino, carboxyl, $C_3$-$C_6$-cycloalkyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylcarbonyl, $C_1$-$C_6$-alkoxycarbonyl, $C_1$-$C_6$-alkylthio, $C_1$-$C_6$-haloalkylthio, $C_1$-$C_6$-alkyl sulfonyl and $C_1$-$C_6$-haloalkylsulfonyl;

$R^b$ is selected from the group consisting of halogen, cyano, nitro, hydroxy, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy, and $C_1$-$C_6$-alkylcarbonyloxy;

$R^c$ is selected from the group consisting of hydrogen, OH, $NH_2$, $C_1$-$C_6$-alkyl, $C_2$-$C_6$-alkenyl, $C_2$-$C_6$-alkynyl, $C_1$-$C_6$-alkoxy, $C_1$-$C_6$-alkylamino, di($C_1$-$C_6$-alkyl)amino, wherein the carbon atoms in these radicals may carry any combination of 1, 2 or 3 radicals $R^a$;

phenyl, benzyl, 5 or 6 membered hetaryl, phenylamino, N—($C_1$-$C_6$-alkyl)-N-phenyl-amino and diphenylamino, wherein aromatic group may be unsubstituted or may carry 1, 2 or 3 substituents $R^b$;

$R^d$, $R^e$ are independently of each other selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, di($C_1$-$C_6$-alkyl)amino, wherein the carbon atoms in these groups may carry any combination of 1, 2 or 3 radicals $R^a$;

phenyl, benzyl, and 5 or 6 membered hetaryl, wherein the aromatic group may be unsubstituted or may carry 1, 2 or 3 substituents $R^b$;

$R^f$, $R^g$ are independently of each other selected from the group consisting of hydrogen, hydroxy, amino, $C_1$-$C_6$-alkyl, $C_1$-$C_6$-haloalkyl, $C_2$-$C_6$-alkenyl, $C_2$-$C_6$-alkynyl, wherein the carbon atoms in these groups may carry any combination of 1, 2 or 3 radicals $R^a$;

phenyl, benzyl, and 5 or 6 membered hetaryl, wherein aromatic group may be unsubstituted or may carry 1, 2 or 3 substituents $R^b$;

$R^h$ is selected from the group consisting of hydrogen, $C_1$-$C_6$-alkyl, $C_2$-$C_6$-alkenyl, $C_2$-$C_6$-alkynyl, $C_1$-$C_6$-alkylamino, di($C_1$-$C_6$-alkyl)amino, $C_2$-$C_6$-alkandiylamino, $C_2$-$C_6$-alkenylamino, di($C_2$-$C_6$-alkenyl)amino, $C_2$-$C_6$-alkynylamino, di($C_2$-$C_6$-alkynyl)amino, $C_1$-$C_6$-alkoxy, $C_2$-$C_6$-alkenyloxy, $C_2$-$C_6$-alkynyloxy, $C_1$-$C_6$-alkylthio, $C_3$-$C_{12}$-cycloalkylthio, $C_2$-$C_6$-alkenylthio, $C_2$-$C_6$-alkynylthio, wherein the carbon atoms in these groups may be substituted with 1, 2, 3, 4 or 5 radicals $R^a$;

a radical Y-Ar, a radical Y-Cy and a radical Y-Hc, and wherein

Y is a single bond, oxygen, sulfur, nitrogen, NH, $NR^f$, $C_1$-$C_6$-alkandiyl, $C_1$-$C_6$-alkandiyloxy, carbonyl or carbonyloxy, wherein the aliphatic carbon atoms in these groups may be unsubstituted or substituted with $R^a$;

Ar is phenyl or naphthyl, wherein Ar is unsubstituted or may carry any combination of 1 to 5 radicals $R^b$ Cy is $C_3$-$C_{12}$-cycloalkyl, which is unsubstituted or substituted with 1 to 5 radicals $R^b$;

Hc is saturated or partially unsaturated 3 to 8 membered heterocycle, which contains 1, 2, 3 or 4 heteroatoms selected from the group consisting of oxygen, sulfur and nitrogen atoms and/or 1 or 2 heteroaromatic groups selected from the group consisting of S(O) and $S(O)_2$ as ring members, and wherein the ring is unsubstituted or may carry 1, 2, 3 or 4 radicals $R^b$;

$R^i$ are each independently selected from the group consisting of hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from the group consisting of O, S and N;

$R^j$ is selected from the group consisting of hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, hydrazino, ($C_1$-$C_6$-alkyl)hydrazino, di($C_1$-$C_6$-alkyl)hydrazino, phenyl and heteroaryl, which can be a mono- or bicyclic 5 to 10 membered heteroaromatic ring, which contains 1, 2, 3 or 4 heteroatoms selected from the group consisting of O, S and N;

or the enantiomers, diastereomers or salts thereof;

with the provisos that if A is $C(R^{A.1})(R^{A.2})$, then at least one of $R^4$, $R^{5.1}$, $R^{5.2}$, $R^{A.1}$ or $R^{A.2}$ is different than hydrogen.

33. The method as defined in claim 32, wherein the amino-thiourea compound of the formula I is applied in an amount of from 100 mg to 10 kg per 100 kg of seeds.

34. The method as defined in claim 32, wherein of the resulting plant's roots and shoots are protected.

35. A seed treated with an amino-thiourea compound of the formula I

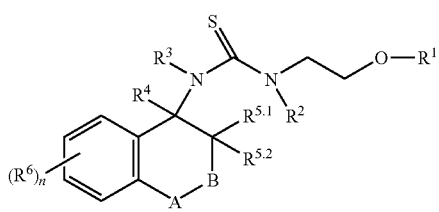

(I)

wherein
n is 0, 1, 2, 3 or 4;
A is $CR^{A.1}R^{A.2}$, oxygen, $NR^{A.3}$, sulfur, S(O) or $S(O)_2$,
  wherein
  $R^{A.1}$, $R^{A.2}$ are independently of each other selected from the group consisting of hydrogen, halogen, cyano, nitro, hydroxy, mercapto, amino, $C_1$-$C_6$-alkyl, $C_1$-$C_6$-haloalkyl, $C_1$-$C_6$-alkoxy, $C_1$-$C_6$-alkylamino, di-($C_1$-$C_6$-alkyl)amino, wherein the carbon atoms in the last 5 mentioned radicals may be unsubstituted or may carry any combination of 1, 2 or 3 radicals $R^a$,
  $C_3$-$C_8$-cycloalkyl, phenyl and benzyl, wherein each of the last three mentioned radicals may be unsubstituted or may carry any combination of 1, 2, 3, 4 or 5 radicals $R^b$; or
  $R^{A.1}$ together with $R^{A.2}$ may also be =O, =$NR^c$ or =$CR^dR^e$;
  $R^{A.3}$ is selected from the group consisting of hydrogen, formyl, CN, $C_1$-$C_6$-alkyl, $C_2$-$C_6$-alkenyl, $C_2$-$C_6$-alkynyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, ($C_1$-$C_6$-alkyl)thiocarbonyl, ($C_1$-$C_6$-alkoxy)thiocarbonyl, wherein the carbon atoms in the aliphatic radicals of the aforementioned groups may carry any combination of 1, 2 or 3 radicals $R^a$;
  $C(O)NR^fR^g$, $C(S)NR^fR^g$, $(SO_2)NR^fR^g$,
    phenyl, benzyl, phenoxycarbonyl, 5 or 6 membered hetarylmethyl, 5 or 6 membered hetarylcarbonyl and benzoyl, wherein each of the last six mentioned radicals may be unsubstituted or may carry any combination of 1, 2, 3, 4 or 5 radicals $R^b$, and wherein the 5 or 6 membered heteroaromatic ring in hetarylmethyl and hetarylcarbonyl contains 1, 2, 3 or 4 heteroatoms selected from the group consisting of oxygen, sulfur and nitrogen as ring members;
B is a chemical bond or $CH_2$;
$R^1$ is hydrogen, C(=O)$R^h$ or C(=S)$R^h$;
$R^2$, $R^3$ are selected independently from each other from the group consisting of hydrogen, cyano, nitro, formyl, C(=O)$R^i$, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkoxy)methylen, $C_1$-$C_6$-alkylsulfinyl, $C_1$-$C_6$-alkylsulfenyl and $C_1$-$C_6$-alkylsulfonyl, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C(O)NR^fR^g$, $(SO_2)NR^fR^g$, phenyl, phenyloxy and benzyl, each of the last three mentioned radicals may be unsubstituted or substituted with 1, 2, 3, 4 or 5 radicals $R^b$; or
$R^2$ together with $R^1$ may be $C_1$-$C_3$-alkandiyl, $C_1$-$C_2$-alkandiylcarbonyl, $C_1$-$C_2$-alkandiylthiocarbonyl or a bridging C=O or C=S group;
$R^4$ is selected from the group consisting of hydrogen, formyl, cyano, $C_1$-$C_6$-alkyl, $C_1$-$C_6$-haloalkyl, $C_2$-$C_6$-alkenyl, $C_2$-$C_6$-alkynyl, $C_1$-$C_6$-alkoxycarbonyl, $C_1$-$C_6$-alkylcarbonyl, $C_2$-$C_6$-alkenylcarbonyl, $C_2$-$C_6$-alkynylcarbonyl, wherein the carbon atoms in the last 5 mentioned radicals may be unsubstituted or may carry any combination of 1, 2 or 3 radicals $R^a$;
$C(O)NR^fR^g$, $C(S)NR^fR^g$,
$C_3$-$C_8$-cycloalkyl, $C_3$-$C_8$-cycloalkenyl, aryl, arylmethyl, aryloxycarbonyl, arylcarbonyl, 5 or 6 membered hetaryl, 5 or 6 membered hetarylmethyl and 5 or 6 membered hetarylcarbonyl, wherein each of the six last mentioned radicals may be unsubstituted or may carry any combination of 1, 2, 3, 4 or 5 radicals $R^b$;
$R^{5.1}$, $R^{5.2}$ are independently from each other selected from the group consisting of hydrogen, halogen, hydroxy, nitro, cyano, carboxy, formyl, formyloxy, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_2$-$C_6$-alkenoxy, $C_2$-$C_6$-alkynoxy, $C_1$-$C_6$-haloalkoxy, $C_1$-$C_6$-alkylthio, $C_2$-$C_6$-alkenylthio, $C_2$-$C_6$-alkynylthio, $C_1$-$C_6$-haloalkylthio, wherein the carbon atoms in these groups may carry any combination of 1, 2 or 3 radicals $R^a$;
$C_3$-$C_8$-cycloalkyl, $C_3$-$C_8$-cycloalkenyl, phenyl, benzyl, 5 or 6 membered hetaryl and 5 or 6 membered hetarylmethyl, wherein each of the last mentioned cyclic radicals may be unsubstituted or may carry any combination of 1, 2, 3, 4 or 5 radicals $R^b$, and wherein the 5 or 6 membered heteroaromatic ring in hetarylmethyl and hetaryl contains 1, 2, 3 or 4 heteroatoms selected from the group consisting of oxygen, sulfur and nitrogen as ring members; or
$R^{5.1}$ together with $R^{5.2}$ may also be =O, =$NR^c$ or =$CR^dR^e$;
$R^6$ is selected from the group consisting of halogen, OH, SH, $NH_2$, $SO_3H$, COOH, cyano, azido, nitro, formyl, formyloxy, $CONH_2$, $CSNH_2$, CH=N—OH, CH=N—O—($C_1$-$C_6$)-alkyl, C(=O)$R^j$, C(=S)$R^j$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, $C_1$-$C_6$-alkylamino, di($C_1$-$C_6$-alkyl)amino, $C_1$-$C_6$-alkylthio, $C_2$-$C_6$-alkenyloxy, $C_2$-$C_6$-alkenylamino, di($C_1$-$C_6$-alkenyl)amino, $C_2$-$C_6$-alkenylthio, $C_2$-$C_6$-alkynyl, $C_2$-$C_6$-alkynyloxy, $C_2$-$C_6$-alkynylamino, di($C_1$-$C_6$-alkynyl)amino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkenylsulfoxyl, $C_2$-$C_6$-alkynylsulfonyl, $C_2$-$C_6$-alkynylsulfoxyl, ($C_1$-$C_6$-alkoxy)carbonyl, ($C_2$-$C_6$-alkenyloxy)carbonyl, ($C_2$-$C_6$-alkynyloxy)carbonyl, ($C_1$-$C_6$-alkyl)carbonyloxy, ($C_2$-$C_6$-alkenyl-)carbonyl-oxy, ($C_2$-$C_6$-alkynyl)carbonyloxy, ($C_1$-$C_6$-alkyl)carbonyl-amino, ($C_2$-$C_6$-alkenyl)carbonyl-amino, ($C_2$-$C_6$-alkynyl)carbonyl-amino, wherein the carbon atoms in the aliphatic radicals of the aforementioned groups may carry any combination of 1, 2 or 3 radicals $R^a$;
$C(O)NR^fR^g$, $(SO_2)NR^fR^g$,
a radical Y-Ar, a radical Y-Hc and a radical Y-Cy, wherein Y is a single bond, oxygen, sulfur, nitrogen, NH, $NR^f$, $C_1$-$C_6$-alkandiyl, $C_1$-$C_6$-alkandiyloxy, carbonyl or carbonyloxy group;
Ar is phenyl or naphthyl, wherein Ar is unsubstituted or may carry any combination of 1 to 5 radicals $R^b$;
Hc is a mono- or bicyclic 5- to 10-membered heteroaromatic ring, which contains 1, 2, 3 or 4 heteroatoms selected from 2 oxygen, 2 sulfur and 3 nitrogen atoms as ring members, wherein He is unsubstituted or may carry any combination of 1 to 5 radicals $R^b$ Cy is $C_3$-$C_{12}$-cycloalkyl, which is unsubstituted or substituted with 1 to 5 radicals $R^b$ and wherein the radical(s) $R^6$ that is/are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals $R^b$;

$R^a$ is selected from the group consisting of halogen, cyano, nitro, hydroxy, mercapto, amino, carboxyl, $C_3$-$C_6$-cycloalkyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylcarbonyl, $C_1$-$C_6$-alkoxycarbonyl, $C_1$-$C_6$-alkylthio, $C_1$-$C_6$-haloalkylthio, $C_1$-$C_6$-alkylsulfonyl and $C_1$-$C_6$-haloalkylsulfonyl;

$R^b$ is selected from the group consisting of halogen, cyano, nitro, hydroxy, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy, and $C_1$-$C_6$-alkylcarbonyloxy;

$R^c$ is selected from the group consisting of hydrogen, OH, $NH_2$, $C_1$-$C_6$-alkyl, $C_2$-$C_6$-alkenyl, $C_2$-$C_6$-alkynyl, $C_1$-$C_6$-alkoxy, $C_1$-$C_6$-alkylamino, di($C_1$-$C_6$-alkyl)amino, wherein the carbon atoms in these radicals may carry any combination of 1, 2 or 3 radicals $R^a$;

phenyl, benzyl, 5 or 6 membered hetaryl, phenylamino, N—($C_1$-$C_6$-alkyl)-N-phenyl-amino and diphenylamino, wherein aromatic group may be unsubstituted or may carry 1, 2 or 3 substituents $R^b$;

$R^d$, $R^e$ are independently of each other selected from the group consisting of hydrogen, $C_1$-$C_6$-haloalkyl, $C_2$-$C_6$-alkenyl, $C_2$-$C_6$-alkynyl, $C_1$-$C_6$-alkoxy, di($C_1$-$C_6$-alkyl)amino, wherein the carbon atoms in these groups may carry any combination of 1, 2 or 3 radicals $R^a$;

phenyl, benzyl, and 5 or 6 membered hetaryl, wherein the aromatic group may be unsubstituted or may carry 1, 2 or 3 substituents $R^b$;

$R^f$, $R^g$ are independently of each other selected from the group consisting of hydrogen, hydroxy, amino, $C_1$-$C_6$-alkyl, $C_1$-$C_6$-haloalkyl, $C_2$-$C_6$-alkenyl, $C_2$-$C_6$-alkynyl, wherein the carbon atoms in these groups may carry any combination of 1, 2 or 3 radicals $R^a$;

phenyl, benzyl, and 5 or 6 membered hetaryl, wherein aromatic group may be unsubstituted or may carry 1, 2 or 3 substituents $R^b$;

$R^h$ is selected from the group consisting of hydrogen, $C_1$-$C_6$-alkyl, $C_2$-$C_6$-alkenyl, $C_2$-$C_6$-alkynyl, $C_1$-$C_6$-alkylamino, di(($C_1$-$C_6$-alkyl)amino, $C_2$-$C_6$-alkandiylamino, $C_2$-$C_6$-alkenylamino, di($C_2$-$C_6$-alkenyl)amino, $C_2$-$C_6$-alkynylamino, di($C_2$-$C_6$-alkynyl)amino, $C_1$-$C_6$-alkoxy, $C_2$-$C_6$-alkenyloxy, $C_2$-$C_6$-alkynyloxy, $C_1$-$C_6$-alkylthio, $C_3$-$C_{12}$-cycloalkylthio, $C_2$-$C_6$-alkenylthio, $C_2$-$C_6$-alkynylthio, wherein the carbon atoms in these groups may be substituted with 1, 2, 3, 4 or 5 radicals $R^a$;

a radical Y-Ar, a radical Y-Cy and a radical Y-Hc, and wherein

Y is a single bond, oxygen, sulfur, nitrogen, NH, $NR^f$, $C_1$-$C_6$-alkandiyl, $C_1$-$C_6$-alkandiyloxy, carbonyl or carbonyloxy, wherein the aliphatic carbon atoms in these groups may be unsubstituted or substituted with $R^a$;

Ar is phenyl or naphthyl, wherein Ar is unsubstituted or may carry any combination of 1 to 5 radicals $R^b$ Cy is $C_3$-$C_{12}$-cycloalkyl, which is unsubstituted or substituted with 1 to 5 radicals $R^b$;

Hc is saturated or partially unsaturated 3 to 8 membered heterocycle, which contains 1, 2, 3 or 4 heteroatoms selected from the group consisting of oxygen, sulfur and nitrogen atoms and/or 1 or 2 heteroaromatic groups selected from the group consisting of S(O) and $S(O)_2$ as ring members, and wherein the ring is unsubstituted or may carry 1, 2, 3 or 4 radicals $R^b$;

$R^i$ are each independently selected from the group consisting of hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from the group consisting of O, S and N;

$R^j$ is selected from the group consisting of hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, hydrazino, ($C_1$-$C_6$-alkyl)hydrazino, di($C_1$-$C_6$-alkyl)hydrazino, phenyl and heteroaryl, which can be a mono- or bicyclic 5 to 10 membered heteroaromatic ring, which contains 1, 2, 3 or 4 heteroatoms selected from the group consisting of O, S and N;

or the enantiomers, diastereomers or salts thereof;

with the provisos that if A is $C(R^{A.1})(R^{A.2})$, then at least one of $R^4$, $R^{5.1}$, $R^{5.2}$, $R^{A.1}$ or $R^{A.2}$ is different than hydrogen, or the enantiomers, diastereomers or salts thereof, in an amount of from 0.1 g to 10 kg per 100 kg of seed.

36. A method of protecting animals against infestation which comprises applying to the animals an effective amount of an amino-thiourea compound of formula I

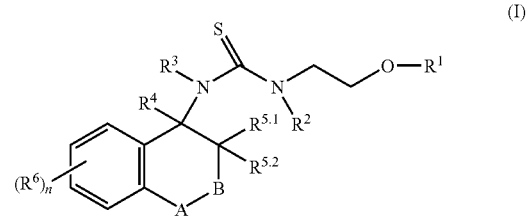

(I)

wherein n is 0, 1, 2, 3 or 4;

A is $CR^{A.1}R^{A.2}$, oxygen, $NR^{A.3}$, sulfur, S(O) or $S(O)_2$, wherein $R^{A.1}$, $R^{A.2}$ are independently of each other selected from the group consisting of hydrogen, halogen, cyano, nitro, hydroxy, mercapto, amino, $C_1$-$C_6$-alkyl, $C_1$-$C_6$-haloalkyl, $C_1$-$C_6$-alkoxy, $C_1$-$C_6$-alkylamino, and di-($C_1$-$C_6$-alkyl)amino, wherein the carbon atoms in the last 5 mentioned radicals may be unsubstituted or may carry any combination of 1, 2 or 3 radicals $R^a$, $C_3$-$C_8$-cycloalkyl, phenyl and benzyl, wherein each of the last three mentioned radicals may be unsubstituted or may carry any combination of 1, 2, 3, 4 or 5 radicals $R^b$; or $R^{A.1}$ together with $R^{A.2}$ may also be =O, =$NR^c$ or =$CR^dR^e$;

$R^{A.3}$ is selected from the group consisting of hydrogen, formyl, CN, $C_1$-$C_6$-alkyl, $C_2$-$C_6$-alkenyl, $C_2$-$C_6$-alkynyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, ($C_1$-$C_6$-alkyl)thiocarbonyl, ($C_1$-$C_6$-alkoxy)thiocarbonyl, wherein the carbon atoms in the aliphatic radicals of the aforementioned groups may carry any combination of 1, 2 or 3 radicals $R^a$;

C(O)$NR^fR^g$, C(S)$NR^fR^g$, (SO$_2$)$NR^fR^g$, phenyl, benzyl, phenoxycarbonyl, 5 or 6 membered hetarylmethyl, 5 or 6 membered hetarylcarbonyl and benzoyl, wherein each of the last six mentioned radicals may be unsubstituted or may carry any combination of 1, 2, 3, 4 or 5 radicals $R^b$, and wherein the 5 or 6 membered heteroaromatic ring in hetarylmethyl and hetarylcarbonyl contains 1, 2, 3 or 4 heteroatoms selected from the group consisting of oxygen, sulfur and nitrogen as ring members;

B is a chemical bond or CH$_2$;

$R^1$ is hydrogen, C(=O)$R^h$ or C(=S)$R^h$;

$R^2$, $R^3$ are selected independently from each other from the group consisting of hydrogen, cyano, nitro, formyl, C(=O)$R^i$, $C_1$-$C_6$-alkyl, $C_2$-$C_6$-alkenyl, $C_2$-$C_6$-alkynyl, $C_3$-$C_8$-cycloalkyl, $C_1$-$C_6$-alkoxy, ($C_1$-$C_6$-alkoxy)methylen, $C_1$-$C_6$-alkylsulfinyl, $C_1$-$C_6$-alkylsulfenyl and $C_1$-$C_6$-alkylsulfonyl wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, C(O)$NR^fR^g$, (SO$_2$)$NR^fR^g$, phenyl, phenyloxy and benzyl, each of the last three mentioned radicals may be unsubstituted or substituted with 1, 2, 3, 4 or 5 radicals $R^b$; or $R^2$ together with $R^1$ may be $C_1$-$C_3$-alkandiyl, $C_1$-$C_2$-alkandiylcarbonyl, $C_1$-$C_2$-alkandiylthiocarbonyl or a bridging C=O or C=S group;

$R^4$ is selected from the group consisting of hydrogen, formyl, cyano, $C_1$-$C_6$-alkyl, $C_1$-$C_6$-haloalkyl, $C_2$-$C_6$-alkenyl, $C_2$-$C_6$-alkynyl, $C_1$-$C_6$-alkoxycarbonyl, $C_1$-$C_6$-alkylcarbonyl, $C_2$-$C_6$-alkenylcarbonyl, $C_2$-$C_6$-alkynylcarbonyl, wherein the carbon atoms in the last 5 mentioned radicals may be unsubstituted or may carry any combination of 1, 2 or 3 radicals $R^a$;

C(O)$NR^fR^g$, C(S)$NR^fR^g$, $C_3$-$C_8$-cycloalkyl, $C_3$-$C_8$-cycloalkenyl, aryl, arylmethyl, aryloxycarbonyl, arylcarbonyl, 5 or 6 membered hetaryl, 5 or 6 membered hetarylmethyl and 5 or 6 membered hetarylcarbonyl, wherein each of the six last mentioned radicals may be unsubstituted or may carry any combination of 1, 2, 3, 4 or 5 radicals $R^b$;

$R^{5.1}$, $R^{5.2}$ are independently from each other selected from the group consisting of hydrogen, halogen, hydroxy, nitro, cyano, carboxy, formyl, formyloxy, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_2$-$C_6$-alkenoxy, $C_2$-$C_6$-alkynoxy, $C_1$-$C_6$-haloalkoxy, $C_1$-$C_6$-alkylthio, $C_2$-$C_6$-alkenylthio, $C_2$-$C_6$-alkynylthio, and $C_1$-$C_6$-haloalkylthio, wherein the carbon atoms in these groups may carry any combination of 1, 2 or 3 radicals $R^a$;

$C_3$-$C_8$-cycloalkyl, $C_3$-$C_8$-cycloalkenyl, phenyl, benzyl, 5 or 6 membered hetaryl and 5 or 6 membered hetarylmethyl, wherein each of the last mentioned cyclic radicals may be unsubstituted or may carry any combination of 1, 2, 3, 4 or 5 radicals $R^b$, and wherein the 5 or 6 membered heteroaromatic ring in hetarylmethyl and hetaryl contains 1, 2, 3 or 4 heteroatoms selected from the group consisting of oxygen, sulfur and nitrogen as ring members; or $R^{5.1}$ together with $R^{5.2}$ may also be =O, =S, =$NR^c$ or =$CR^dR^e$;

$R^6$ is selected from the group consisting of halogen, OH, SH, NH$_2$, SO$_3$H, COOH, cyano, azido, nitro, formyl, formyloxy, CONH$_2$, CSNH$_2$, CH=N—OH, CH=N—O—($C_1$-$C_6$)-alkyl, C(=O)$R^j$, C(=S)$R^j$, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, $C_1$-$C_6$-alkylamino, di($C_1$-$C_6$-alkyl)amino, $C_1$-$C_6$-alkylthio, $C_2$-$C_6$-alkenyloxy, $C_2$-$C_6$-alkenylamino, di($C_1$-$C_6$-alkenyl)amino, $C_2$-$C_6$-alkenylthio, $C_2$-$C_6$-alkynyl, $C_2$-$C_6$-alkynyloxy, $C_2$-$C_6$-alkynylamino, di($C_1$-$C_6$-alkynyl)amino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkenylsulfoxyl, $C_2$-$C_6$-alkynylsulfonyl, $C_2$-$C_6$-alkynylsulfoxyl, ($C_1$-$C_6$-alkoxy)carbonyl, ($C_2$-$C_6$-alkenyloxy)carbonyl, ($C_2$-$C_6$-alkynyloxy)carbonyl, ($C_1$-$C_6$-alkyl)carbonyloxy, ($C_2$-$C_6$-alkenyl-)carbonyl-oxy, ($C_2$-$C_6$-alkynyl)carbonyloxy, ($C_1$-$C_6$-alkyl)carbonyl-amino, ($C_2$-$C_6$-alkenyl)carbonyl-amino, ($C_2$-$C_6$-alkynyl)carbonyl-amino, wherein the carbon atoms in the aliphatic radicals of the aforementioned groups may carry any combination of 1, 2 or 3 radicals $R^a$;

C(O)$NR^fR^g$, (SO$_2$)$NR^fR^g$, a radical Y-Ar, a radical Y-Hc and a radical Y-Cy, wherein Y is a single bond, oxygen, sulfur, nitrogen, NH, $NR^f$, $C_1$-$C_6$-alkandiyl, $C_1$-$C_6$-alkandiyloxy, carbonyl or carbonyloxy group;

Ar is phenyl or naphthyl, wherein Ar is unsubstituted or may carry any combination of 1 to 5 radicals $R^b$;

Hc is a mono- or bicyclic 5- to 10-membered heteroaromatic ring, which contains 1, 2, 3 or 4 heteroatoms selected from 2 oxygen, 2 sulfur and 3 nitrogen atoms as ring members, wherein Hc is unsubstituted or may carry any combination of 1 to 5 radicals $R^b$ Cy is $C_3$-$C_{12}$-cycloalkyl, which is unsubstituted or substituted with 1 to 5 radicals $R^b$ and wherein the radical(s) $R^6$ that is/are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals $R^b$;

$R^a$ is selected from the group consisting of halogen, cyano, nitro, hydroxy, mercapto, amino, carboxyl, $C_3$-$C_6$-cycloalkyl, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylcarbonyl, $C_1$-$C_6$-alkoxycarbonyl, $C_1$-$C_6$-alkylthio, $C_1$-$C_6$-haloalkylthio, $C_1$-$C_6$-alkyl sulfonyl and $C_1$-$C_6$-haloalkyl sulfonyl;

$R^b$ is selected from the group consisting of halogen, cyano, nitro, hydroxy, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy, and $C_1$-$C_6$-alkylcarbonyloxy;

$R^c$ is selected from the group consisting of hydrogen, OH, $NH_2$, $C_1$-$C_6$-alkyl, $C_2$-$C_6$-alkenyl, $C_2$-$C_6$-alkynyl, $C_1$-$C_6$-alkoxy, $C_1$-$C_6$-alkylamino, di($C_1$-$C_6$-alkyl)amino, wherein the carbon atoms in these radicals may carry any combination of 1, 2 or 3 radicals $R^a$;

phenyl, benzyl, 5 or 6 membered hetaryl, phenylamino, N—($C_1$-$C_6$-alkyl)-N-phenyl-amino and diphenylamino, wherein aromatic group may be unsubstituted or may carry 1, 2 or 3 substituents $R^b$;

$R^d$, $R^e$ are independently of each other selected from the group consisting of hydrogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, di($C_1$-$C_6$-alkyl)amino, wherein the carbon atoms in these groups may carry any combination of 1, 2 or 3 radicals $R^a$;

phenyl, benzyl, and 5 or 6 membered hetaryl, wherein the aromatic group may be unsubstituted or may carry 1, 2 or 3 substituents $R^b$;

$R^f$, $R^g$ are independently of each other selected from the group consisting of hydrogen, hydroxy, amino, $C_1$-$C_6$-alkyl, $C_1$-$C_6$-haloalkyl, $C_2$-$C_6$-alkenyl, $C_2$-$C_6$-alkynyl, wherein the carbon atoms in these groups may carry any combination of 1, 2 or 3 radicals $R^a$;

phenyl, benzyl, and 5 or 6 membered hetaryl, wherein aromatic group may be unsubstituted or may carry 1, 2 or 3 substituents $R^b$;

$R^h$ is selected from the group consisting of hydrogen, $C_1$-$C_6$-alkyl, $C_2$-$C_6$-alkenyl, $C_2$-$C_6$-alkynyl, $C_1$-$C_6$-alkylamino, di($C_1$-$C_6$-alkyl)amino, $C_2$-$C_6$-alkandiylamino, $C_2$-$C_6$-alkenylamino, di($C_2$-$C_6$-alkenyl)amino, $C_2$-$C_6$-alkynylamino, di($C_2$-$C_6$-alkynyl)amino, $C_1$-$C_6$-alkoxy, $C_2$-$C_6$-alkenyloxy, $C_2$-$C_6$-alkynyloxy, $C_1$-$C_6$-alkylthio, $C_3$-$C_{12}$-cycloalkylthio, $C_2$-$C_6$-alkenylthio, $C_2$-$C_6$-alkynylthio, wherein the carbon atoms in these groups may be substituted with 1, 2, 3, 4 or 5 radicals $R^a$;

a radical Y-Ar, a radical Y-Cy and a radical Y-Hc, and wherein

Y is a single bond, oxygen, sulfur, nitrogen, NH, $NR^f$, $C_1$-$C_6$-alkandiyl, $C_1$-$C_6$-alkandiyloxy, carbonyl or carbonyloxy, wherein the aliphatic carbon atoms in these groups may be unsubstituted or substituted with $R^a$;

Ar is phenyl or naphthyl, wherein Ar is unsubstituted or may carry any combination of 1 to 5 radicals $R^b$ Cy is $C_3$-$C_{12}$-cycloalkyl, which is unsubstituted or substituted with 1 to 5 radicals $R^b$ Hc is saturated or partially unsaturated 3 to 8 membered heterocycle, which contains 1, 2, 3 or 4 heteroatoms selected from the group consisting of oxygen, sulfur and nitrogen atoms and/or 1 or 2 heteroaromatic groups selected from the group consisting of S(O) and $S(O)_2$ as ring members, and wherein the ring is unsubstituted or may carry 1, 2, 3 or 4 radicals $R^b$;

$R^i$ are each independently selected from the group consisting of hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkylthio, $C_1$-$C_6$-alkoxy, ($C_1$-$C_6$-alkyl)amino, di($C_1$-$C_6$-alkyl)amino, phenyl and heteroaryl, which can be a mono- or bicyclic 5 to 10 membered heteroaromatic ring, which contains 1, 2, 3 or 4 heteroatoms selected from the group consisting of O, S and N;

$R^j$ is selected from the group consisting of hydrogen, $C_1$-$C_6$-alkyl, $C_2$-$C_6$-alkenyl, $C_2$-$C_6$-alkinyl, $C_3$-$C_8$-cycloalkyl, $C_1$-$C_6$-alkoxy, ($C_1$-$C_6$-alkyl)amino, di($C_1$-$C_6$-alkyl)amino, hydrazino, ($C_1$-$C_6$-alkyl)hydrazino, di($C_1$-$C_6$-alkyl)hydrazino, phenyl and heteroaryl, which can be a mono- or bicyclic 5 to 10 membered heteroaromatic ring, which contains 1, 2, 3 or 4 heteroatoms selected from the group consisting of O, S and N;

or the enantiomers, diastereomers or salts thereof;

with the provisos that if A is $C(R^{A.1})(R^{A.2})$, then at least one of $R^4$, $R^{5.1}$, $R^{5.2}$, $R^{A.1}$ or $R^{A.2}$ is different than hydrogen, or the enantiomers, diastereomers and/or veterinary acceptable salt thereof.

37. The method of claim 36, wherein the infestation is infection by parasites.

* * * * *

UNITED STATES PATENT AND TRADEMARK OFFICE
CERTIFICATE OF CORRECTION

PATENT NO. : 8,173,675 B2
APPLICATION NO. : 12/601017
DATED : May 8, 2012
INVENTOR(S) : Christopher Koradin et al.

It is certified that error appears in the above-identified patent and that said Letters Patent is hereby corrected as shown below:

IN THE CLAIMS:

In col. 117, claim 1, line 5, after "C(=O)R$^i$," insert --$C_1$-$C_6$-alkyl,--;
In col. 117, claim 1, line 14, after "$C_1$-$C_6$-haloalkoxy," insert --$C_1$-$C_6$-alkylthio,--;
In col. 117, claim 1, line 22, after "$C_1$-$C_6$-alkyl," insert --$C_1$-$C_6$-haloalkyl,--;
In col. 119, claim 1, line 19, before "$C_1$-$C_6$-alkandiyloxy," insert --$C_1$-$C_6$-alkandiyl,--; and
In col. 119, claim 1, line 35, before "$C_1$-$C_6$-alkoxy" insert --$C_1$-$C_6$-alkylthio,--.

In col. 120, claim 7, line 7, delete "He" and insert therefore --Hc--; and
In col. 120, claim 7, line 12, delete "He" and insert therefore --Hc--.

In col. 120, claim 8, line 18, delete "He" and insert therefore --Hc--.

In col. 124, claim 30, line 58, delete "R$^h$" and insert therefore --R$^b$--.

In col. 126, claim 32, line 11, delete "R$^1$" and insert therefore --R$^i$--; and
In col. 127, claim 32, line 46, delete "$C_1$-$C_6$-alkyl sulfonyl" and insert therefore
          --$C_1$-$C_6$-alkylsulfonyl--.

In col. 130, claim 35, line 33, after "=O" insert -- =S--;
In col. 130, claim 35, line 66, delete "He" and insert therefore --Hc--; and
In col. 131, claim 35, line 39, after "hydrogen" insert --$C_1$-$C_6$-alkyl,--.

In col. 134, claim 36, line 58, delete "$C_1$ -$C_6$-alkyl sulfonyl and $C_1$-$C_6$-haloalkyl sulfonyl" and
          insert therefore --$C_1$ -$C_6$-alkylsulfonyl and $C_1$-$C_6$-haloalkysulfonyl--;
In col. 136, claim 36, line 16, delete "$C_3$-$C_g$-cycloalkyl" and insert therefore
          --$C_3$-$C_8$-cycloalkyl--.

Signed and Sealed this
Second Day of October, 2012

David J. Kappos
*Director of the United States Patent and Trademark Office*